United States Patent
Reilly et al.

(10) Patent No.: US 10,098,968 B2
(45) Date of Patent: Oct. 16, 2018

(54) ANTI-EGFR ANTIBODIES AND ANTIBODY DRUG CONJUGATES

(71) Applicant: AbbVie Inc., North Chicago, IL (US)

(72) Inventors: Edward B. Reilly, Libertyville, IL (US); Andrew C. Phillips, Libertyville, IL (US); Lorenzo Benatuil, Northborough, MA (US); Chung-Ming Hsieh, Newton, MA (US); Jennifer Perez, Granville, NY (US)

(73) Assignee: Abbvie Inc., North Chicago, IL (US)

( * ) Notice: Subject to any disclaimer, the term of this patent is extended or adjusted under 35 U.S.C. 154(b) by 0 days.

(21) Appl. No.: 15/808,419

(22) Filed: Nov. 9, 2017

(65) Prior Publication Data

US 2018/0125999 A1 May 10, 2018

Related U.S. Application Data

(62) Division of application No. 15/349,692, filed on Nov. 11, 2016, now Pat. No. 9,827,330, which is a division of application No. 14/664,453, filed on Mar. 20, 2015, now Pat. No. 9,493,568.

(60) Provisional application No. 61/968,819, filed on Mar. 21, 2014.

(51) Int. Cl.
| | |
|---|---|
| *C07K 16/28* | (2006.01) |
| *C07K 14/00* | (2006.01) |
| *C07K 16/30* | (2006.01) |
| *A61K 39/00* | (2006.01) |
| *A61K 47/68* | (2017.01) |

(52) U.S. Cl.
CPC ...... *A61K 47/6811* (2017.08); *A61K 47/6803* (2017.08); *A61K 47/6847* (2017.08); *A61K 47/6849* (2017.08); *A61K 47/6851* (2017.08); *A61K 47/6857* (2017.08); *A61K 47/6863* (2017.08); *A61K 47/6865* (2017.08); *C07K 14/00* (2013.01); *C07K 16/2863* (2013.01); *C07K 16/30* (2013.01); *C07K 16/3023* (2013.01); *C07K 16/3046* (2013.01); *C07K 16/3053* (2013.01); *A61K 2039/505* (2013.01); *C07K 2317/21* (2013.01); *C07K 2317/24* (2013.01); *C07K 2317/34* (2013.01); *C07K 2317/56* (2013.01); *C07K 2317/565* (2013.01); *C07K 2317/622* (2013.01); *C07K 2317/73* (2013.01); *C07K 2317/76* (2013.01); *C07K 2317/92* (2013.01)

(58) Field of Classification Search
CPC ............ C07K 16/2863; C07K 2317/21; C07K 2317/565; C07K 2317/56; C07K 2317/24; A61K 47/6849; A61K 47/6803; A61K 47/6851; A61K 2039/505
See application file for complete search history.

(56) References Cited

U.S. PATENT DOCUMENTS

| | | | |
|---|---|---|---|
| 4,943,533 | A | 7/1990 | Mendelsohn et al. |
| 5,212,290 | A | 5/1993 | Vogelstein et al. |
| 5,401,828 | A | 3/1995 | Vogelstein et al. |
| 5,795,965 | A | 8/1998 | Tsuchiya et al. |
| 7,263,946 | B2 | 9/2007 | Worthy et al. |
| 7,447,597 | B2 | 11/2008 | Wang et al. |
| 7,589,180 | B2 | 9/2009 | Old et al. |
| 7,767,792 | B2 | 8/2010 | Johns et al. |
| 8,301,397 | B2 | 10/2012 | Bertoncini et al. |
| 9,493,568 | B2 | 11/2016 | Reilly et al. |
| 9,827,330 | B2 | 11/2017 | Reilly et al. |
| 2003/0054497 | A1 | 3/2003 | Co et al. |
| 2009/0220510 | A1 | 9/2009 | Old et al. |
| 2010/0056762 | A1 | 3/2010 | Old |
| 2010/0092475 | A1 | 4/2010 | Johns et al. |
| 2010/0166744 | A1 | 7/2010 | Wong |
| 2010/0322937 | A1 | 12/2010 | Johns et al. |
| 2011/0150759 | A1 | 6/2011 | Johns et al. |
| 2011/0313230 | A1 | 12/2011 | Johns et al. |
| 2012/0183471 | A1 | 7/2012 | Ritter et al. |
| 2013/0266573 | A1 | 10/2013 | Old et al. |
| 2014/0286968 | A1 | 9/2014 | Leanna et al. |
| 2014/0286969 | A1 | 9/2014 | Tschoepe et al. |
| 2014/0322130 | A1 | 10/2014 | Scott et al. |

FOREIGN PATENT DOCUMENTS

| | | |
|---|---|---|
| WO | WO-1991/03489 A1 | 3/1991 |
| WO | WO-1991/16350 A1 | 10/1991 |
| WO | WO-1996/16988 A1 | 6/1996 |
| WO | WO-2002/092771 A2 | 11/2002 |
| WO | WO-2005/081854 A2 | 9/2005 |
| WO | WO-2007/080392 A2 | 7/2007 |
| WO | WO-2008/033495 A2 | 3/2008 |
| WO | WO-2008/091701 A2 | 7/2008 |
| WO | WO-2008/115404 A1 | 9/2008 |
| WO | WO-2009/023265 A1 | 2/2009 |
| WO | WO-2010/096434 A2 | 8/2010 |
| WO | WO-2012/135360 A1 | 10/2012 |

(Continued)

OTHER PUBLICATIONS

Baselga et al., "Phase I studies of anti-epidermal growth factor receptor chimeric antibody C225 alone and in combination with cisplatin." J. Clin. Oncol. (2000) 904-914, 18(4).

(Continued)

*Primary Examiner* — Ruixiang Li

(74) *Attorney, Agent, or Firm* — Womble Bond Dickinson (US) LLP; Cristin H. Cowles; Kevin A. Fiala

(57) ABSTRACT

The invention relates to anti-epidermal growth factor (EGFR) antibodies and antibody drug conjugates (ADCs), including compositions and methods of using said antibodies and ADCs.

13 Claims, 24 Drawing Sheets

Specification includes a Sequence Listing.

(56) References Cited

FOREIGN PATENT DOCUMENTS

| WO | WO-2014/143765 A1 | 9/2014 |
|---|---|---|
| WO | WO-2014/152199 A1 | 9/2014 |
| WO | WO-2014/153002 A1 | 9/2014 |
| WO | WO-2015/057852 A1 | 4/2015 |

OTHER PUBLICATIONS

Baselga et al., "Phase II study of weekly intravenous recombinant humanized anti-p185HER2 monoclonal antibody in patients with HER2/neu-overexpressing metastatic breast cancer." J. Clin. Oncol. (1996) 737-744, 14(3).

Baselga, "The EGFR as a target for anticancer therapy—focus on cetuximab." Eur. J. Cancer (2001) S16-22, 37 Suppl 4.

Benatuil et al., "An improved yeast transformation method for the generation of very large human antibody libraries." Protein Engineering Design & Selection (2010) pp. 1-5.

Boyer et al., "Relative cytotoxic activity of immunotoxins reactive with different epitopes on the extracellular domain of the c-erbB-2 (HER-2/neu) gene product p185." Int. J. Cancer (1999) 525-531, 82(4).

Buss et al., "Altered epidermal growth factor (EGF)-stimulated protein kinase activity in variant A431 cells with altered growth responses to EGF." Proceedings of the National Academy of Sciences of the United States of America (1982) 2574-2578, 79(8).

Caldas et al., "Humanization of the anti-CD18 antibody 6.7: an unexpected effect of a framework residue in binding to antigen." Mol. Immunol. (2003) 941-952, 39(15).

Casset et al., "A peptide mimetic of an anti-CD4 monoclonal antibody by rational design." Biochem. Biophys. Res. Commun. (2003) 198-205, 307(1).

Chao et al., "Fine epitope mapping of anti-epidermal growth factor receptor antibodies through random mutagenesis and yeast surface display." J. Mol. Biol. (2004) 539-550, 342(2).

Chao, "Characterizing and engineering antibodies against the epidermal growth factor receptor (PhD Thesis)" Submission to the Department of Chemical Engineering in partial fulfillment of the requirements for the degree of Doctor of Philosophy in Chemical Engineering at the Massachusetts Institute of Technology (2008) 53, 54 and 78.

Chien et al., "Significant structural and functional change of an antigen-binding site by a distant amino acid substitution: proposal of a structural mechanism." Proceedings of the National Academy of Sciences of the United States of America (1989) 5532-5536, 86(14).

Cochran et al., "Domain-level antibody epitope mapping through yeast surface display of epidermal growth factor receptor fragments." J. Immunol. Methods (2004) 147-158, 287(1-2).

De Pascalis et al., "Grafting of 'abbreviated' complementarity-determining regions containing specificity-determining residues essential for ligand contact to engineer a less immunogenic humanized monoclonal antibody." Journal of Immunology (Baltimore, MD : 1950) (2002) 3076-3084, 169(6).

Elleman et al., "Identification of a determinant of epidermal growth factor receptor ligand-binding specificity using a truncated, high-affinity form of the ectodomain." Biochemistry (2001) 8930-8939, 40(30).

Fernandes et al., "Glycosylation-induced conformational modification positively regulates receptor-receptor association: a study with an aberrant epidermal growth factor receptor (EGFRvIII/DeltaEGFR) expressed in cancer cells." JBC (2001) 5375-5383, 276(7).

Friedman et al., "Temozolomide and treatment of malignant glioma." Clin. Cancer Res. (2000) 2585-2597, 6(7).

George et al., "Differential effects of anti-beta2-glycoprotein I antibodies on endothelial cells and on the manifestations of experimental antiphospholipid syndrome." Circulation (1998) 900-906, 97(9).

Gill et al., "Relationship between production of epidermal growth factor receptors, gene amplification, and chromosome 7 translocation in variant A431 cells." Somatic Cell and Molecular Genetics (1985) 309-318, 11(4).

Giusti et al., "Somatic diversification of S107 from an antiphosphocholine to an anti-DNA autoantibody is due to a single base change in its heavy chain variable region." Proceedings of the National Academy of Sciences of the United States of America (1987) 2926-2930, 84(9).

Greenspan et al., "Defining epitopes: It's not as easy as it seems." Nat. Biotechnol. (1999) 936-937, 17(10).

Güssow et al. Humanization of monoclonal antibodies. Methods in Enzymology (1991); 203: 99-121.

Henry et al., "A prostate-specific membrane antigen-targeted monoclonal antibody-chemotherapeutic conjugate designed for the treatment of prostate cancer." Cancer Res. (2004) 7995-8001, 64(21).

Hermanson G.T., "Bioconjugate Techniques", 2nd edition, 1996, p. 456.

Hills et al., "Specific targeting of a mutant, activated FGF receptor found in glioblastoma using a monoclonal antibody." Int. J. Cancer (1995) 537-543, 63(4).

Hoang T et al: "PD-144 Tumor response augmentation with combination cetuximab(Erbitux(R)) and bevacizumab (Avastin(R))", Lung Cancer, Elsevier, Amsterdam, NL, vol. 49, Jul. 1, 2005; (Jul. 1, 2005), pp. S108-S109.

Holm et al., "Functional mapping and single chain construction of the anti-cytokeratin 8 monoclonal antibody TS1." Mol. Immunol. (2007) 1075-1084, 44(6).

Jiang et al., "A novel peptide isolated from a phage display peptide library with trastuzumab can mimic antigen epitope of HER-2." JBC (2005) 4656-4662, 280(6).

Johns et al., "Identification of the epitope for the epidermal growth factor receptor-specific monoclonal antibody 806 reveals that it preferentially recognizes an untethered form of the receptor." JBC (2004) 30375-30384, 279(29).

Johns et al., "Novel monoclonal antibody specific for the del-7 epidermal growth factor receptor (EGFR) that also recognizes the EGFR expressed in cells containing amplification of the EGFR gene." Int. J. Cancer (2002) 398-408, 98(3).

Johns et al., "The antitumor monoclonal antibody 806 recognizes a high-mannose form of the EGF receptor that reaches the cell surface when cells over-express the receptor" FASEB J. (2005) 1-18, 19(3).

Johns, "Annual Branch Report 1998 ("Preclinical evaluation of antibodies directed to the de2-7 epidermal growth factor receptors")" Ludwig Institute for Cancer Research (2000) 118-119.

Jung Y D et al: "Effects of combination anti-vascular endothelial growth factor receptor and anti-epidermal growth factor receptor therapies on the growth of gastric cancer in a nude mouse model", European Journal of Cancer, Pergamon Press, Oxford, GB, vol. 38, No. 8, May 1, 2002, pp. 1133-1140.

Jungbluth et al., "A monoclonal antibody recognizing human cancers with amplification/overexpression of the human epidermal growth factor receptor." Proceedings of the National Academy of Sciences of the United States of America (2003) 639-644, 100(2).

Kuan et al., "$^{125}$I-labeled anti-epidermal growth factor receptor-vIII single-chain Fv exhibits specific and high-level targeting of glioma xenografts." Clin. Cancer Res. (1999) 1539-1549, 5(6).

Kuan et al., "Increased binding affinity enhances targeting of glioma xenografts by EGFRvIII-specific scFv." Int. J. Cancer (2000) 962-969, 88(6).

Lax et al., "Noncontiguous regions in the extracellular domain of EGF receptor define ligand-binding specificity." Cell regulation (1991) 337-345, 2(5).

Liu et al., "Engineering therapeutic monoclonal antibodies." Immunological Reviews (2008) 9-27, 222.

Luwor et al., "Monoclonal antibody 806 inhibits the growth of tumor xenografts expressing either the de2-7 or amplified epidermal growth factor receptor (EGFR) but not wild-type EGFR." Cancer Res. (2001) 5355-5361, 61(14).

MacCallum et al., "Antibody-antigen interactions: contact analysis and binding site topography." J. Mol. Biol. (1996) 732-745, 262(5).

(56) References Cited

OTHER PUBLICATIONS

Mariuzza et al., "The structural basis of antigen-antibody recognition." Annual Review of Biophysics and Biophysical Chemistry (1987) 139-159, 16.
Marks et al., "By-passing immunization: building high affinity human antibodies by chain shuffling." Bio/technology (Nature Publishing Company) (1992) 779-783, 10(7).
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor." Cancer Res. (2001) 5349-5354, 61(14).
Modjtahedi et al., "Antitumor activity of combinations of antibodies directed against different epitopes on the extracellular domain of the human EGF receptor." Cell Biophysics (1993) 129-146, 22(1-3).
Naumov George N et al: "Combined vascular endothelial growth factor receptor and epidermal growth factor receptor (EGFR) blockade inhibits tumor growth in xenograft models of EGFR inhibitor resistance." Clinical Cancer Research: An Official Journal of the American Association for Cancer Research May 15, 2009 LNKD PUBMED:19447865, vol. 15, No. 10, May 15, 2009 (May 15, 2009), pp. 3484-3494.
Panousis et al., "Engineering and characterisation of chimeric monoclonal antibody 806 (ch806) for targeted immunotherapy of tumours expressing de2-7 EGFR or amplified EGFR." British Journal of Cancer (2005) 1069-1077, 92(6).
Perera et al., "Internalization, intracellular trafficking, and biodistribution of monoclonal antibody 806: a novel anti-epidermal growth factor receptor antibody." Neoplasia (2007) 1099-1110, 9(12).
Press et al., "Ricin A-chain containing immunotoxins directed against different epitopes on the CD2 molecule differ in their ability to kill normal and malignant T cells." Journal of Immunology (Baltimore, MD : 1950) (1988) 4410-4417, 141(12).
Presta, "Engineering of therapeutic antibodies to minimize immunogenicity and optimize function." Advanced Drug Delivery Reviews (2006) 640-656, 58(5-6).
Presta, "Molecular engineering and design of therapeutic antibodies." Curr. Opin. Immunol. (2008) 460-470, 20(4).
Reck M et al: "Advances in anti- VEGF and anti- EGFR therapy for advanced non-small cell lung cancer", Lung Cancer, Elsevier, Amsterdam, NL, vol. 63, No. 1, Jan. 1, 2009 (Jan. 1, 2009), pp. 1-9.
Reist et al., "Tumor-specific anti-epidermal growth factor receptor variant III monoclonal antibodies: use of the tyramine-cellobiose radioiodination method enhances cellular retention and uptake in tumor xenografts." Cancer Res. (1995) 4375-4382, 55(19).
Reiter et al., "Comparative genomic sequence analysis and isolation of human and mouse alternative EGFR transcripts encoding truncated receptor isoforms." *Genomics* (2001) 1-20, 71(1).
Riemer et al., "Matching of trastuzumab (Herceptin) epitope mimics onto the surface of Her-2/neu—a new method of epitope definition." Mol. Immunol. (2005) 1121-1124, 42(9).
Rudikoff, S. et al., "Single amino acid substitution altering antigen-binding specificity" Proc. Natl. Acad. Sci. USA (1982) 79 (6) 1979-83.
Sakahara et al., "Effect of DTPA conjugation on the antigen binding activity and biodisruption of monoclonal antibodies against α-fetoprotein", Nucl. Med., 1985, 26, 750-755.
Sampson et al., "Unarmed, tumor-specific monoclonal antibody effectively treats brain tumors." Proceedings of the National Academy of Sciences of the United States of America (2000) 7503-7508, 97(13).
Schwechheimer et al., "EGFR gene amplification—rearrangement in human glioblastomas." Int. J. Cancer (1995) 145-148, 62(2).
Scott et al., "A phase I clinical trial with monoclonal antibody ch806 targeting transitional state and mutant epidermal growth factor receptors." Proceedings of the National Academy of Sciences of the United States of America (2007) 4071-4076, 104(10).
Sivasubramanian et al., "Structural model of the mAb 806-EGFR complex using computational docking followed by computational and experimental mutagenesis." *Structure* (2006) 401-414, 14(3).
Stancovski et al., "Mechanistic aspects of the opposing effects of monoclonal antibodies to the ERBB2 receptor on tumor growth." Proceedings of the National Academy of Sciences of the United States of America (1991) 8691-8695, 88(19).
Sugimura, K., Human antibody engineering, Bio-ventures, Jul. 1, 2002, vol. 2,; No. 4, pp. 30-33.
Sutherland et al., "SGN-CD33A: a novel CD33-targeting antibody-drug conjugate using a pyrrolobenzodiazepine dimer is active in models of drug-resistant AML." *Blood*, vol. 122 (2013) pp. 1455-1463.
Wikstrand et al., "Monoclonal antibodies against EGFRvIII are tumor specific and react with breast and lung carcinomas and malignant gliomas." Cancer Res. (1995) 3140-3148, 55(14).
Wu et al., "Humanization of a murine monoclonal antibody by simultaneous optimization of framework and CDR residues." J. Mol. Biol. (1999) 151-162, 294(1).
Xu et al., "Antibody-induced growth inhibition is mediated through immunochemically and functionally distinct epitopes on the extracellular domain of the c-erbB-2 (HER-2/neu) gene product p185." Int. J. Cancer (1993) 401-408, 53(3).
A Study Evaluating Safety and Pharmacokinetics of ABBV-221 in Subjects With Advanced Solid Tumor Types Likely to Exhibit Elevated Levels of Epidermal Growth Factor Receptor, (see https://clinicaltrials.gov/ct2/show/NCT02365662?term=ABBV-221&rank=1, accessed Mar. 18, 2014) 4 pages.
Boland, William and Gwyn Bebb, The emerging role of nimotuzumab in the treatment of non-small cell lung cancer. Biologics: Targets and Therapy, (2010) 4: 291-298.
Garrett, Thomas et al., Antibodies specifically targeting a locally misfolded region of tumor associated EGFR. Proc. Natl. Acad. Sci., USA (Mar. 31, 2009) 106(13): 5082-5087.
International Search Report and Written Opinion issued in International Application No. PCT/US2015/021849, dated Jul. 13, 2015.
U.S. Pat. No. 9,493,568, Pub. No. 2015-0337042 A1, dated Nov. 26, 2015.
U.S. Pat. No. 9,827,330, Pub. No. 2017-0072065 A1, dated Mar. 16, 2017.

VH domains:
Ab1  QVQLQESGPGLVKPSQTLSLTCTVSGYSISSDFAWNWIRQPPGKGLEWMGVISYSGNTRYQPSLKSRITISRDTSKNQFFLKLNSVTAADTATYYCVTAGRGFPYNGQGTLVTVSS
AbA  EVQLQESGPGLVKPSQTLSLTCTVSGYSISRDFAWNWIRQPPGKGLEWMGVISYNGNTRYQPSLKSRITISRDTSKNQFFLKLNSVTAADTATYYCVTASRGFPYNGQGTLVTVSS
          CDR1                               CDR2                                                    CDR3

VL domains: (Ab1 and AbA have the same VL sequence)

Ab1  DIQMTQSPSSMSVSVGDRVTITCHSSQDINSNIGWLQQKPGKSFKGLIYHGTNLDDGVPSRFSGSGSGTDYTLTISSLQPEDFATYYCVQYAQFPWTFGGGTKLEIK
AbA  DIQMTQSPSSMSVSVGDRVTITCHSSQDINSNIGWLQQKPGKSFKGLIYHGTNLDDGVPSRFSGSGSGTDYTLTISSLQPEDFATYYCVQYAQFPWTFGGGTKLEIK
          CDR1                         CDR2                                              CDR3

Figure 1

LC:
the same

```
        DIQMTQSPSSMSVSVGDRVTITCHSSQDINSNIGWLQQKPGKSFKGLIYHGTNLDDGVPSRFSGSGSGT
        DYTLTISSLQPEDFATYYCVQYAQFPWTFGGGTKLEIKRTVAAPSVFIFPPSDEQLKSGTASVVCLLNNFY
        PREAKVQWKVDNALQSGNSQESVTEQDSKDSTYSLSSTLTLSKADYEKHKVYACEVTHQGLSSPVTKSF
        NRGEC    SEQ ID NO: 13
```

HC:
6 AA change

```
Ab1    QVQLQESGPGLIVKPSQTLSLTCTVSGYSISSDFAWNWIRQPPGKGLEWMGYISYSGNTRYQPSLKSRITI
AbA    EVQLQESGPGLVKPSQTLSLTCTVSGYSISISRDFAWNWIRQPPGKGLEWMGYISYNGNTRYQPSLKSRITI

Ab1    SRDTSKNQFFLKLNSVTAADTATYYCVTAGRGFPYWGQGTLVTVSSASTKGPSVFPLAPSSKSTSGGTA
AbA    SRDTSKNQFFLKLNSVTAADTATYYCVTASRGFPYWGQGTLVTVSSASTKGPSVFPLAPSSKSTSGGTA

Ab1    ALGCLVKDYFPEPVTVSWNSGALTSGVHTFPAVLQSSGLYSLSSVVTVPSSSLGTQTYICNVNHKPSNTK
AbA    ALGCLVKDYFPEPVTVSWNSGALTSGVHTFPAVLQSSGLYSLSSVVTVPSSSLGTQTYICNVNHKPSNTK

Ab1    VDKKVEPKSCDKTHTCPPCPAPELLGGPSVFLFPPKPKDTLMISRTPEVTCVVVDVSHEDPEVKFNWYVD
AbA    VDKKVEPKSCDKTHTCPPCPAPELLGGPSVFLFPPKPKDTLMISRTPEVTCVVVDVSHEDPEVKFNWYVD

Ab1    GVEVHNAKTKPREEQYNSTYRVVSVLTVLHQDWLNGKEYKCKVSNKALPAPIEKTISKAKGQPREPQVYT
AbA    GVEVHNAKTKPREEQYNSTYRVVSVLTVLHQDWLNGKEYKCKVSNKALPAPIEKTISKAKGQPREPQVYT

Ab1    LPPSRDELTKNQVSLTCLVKGFYPSDIAVEWESNGQPENNYKTTPPVLDSDGSFFLYSKLTVDKSRWQQ
AbA    LPPSREEMTKNQVSLTCLVKGFYPSDIAVEWESNGQPENNYKTTPPVLDSDGSFFLYSKLTVDKSRWQQ

Ab1    GNVFSCSVMHEALHNHYTQKSLSLSPG    SEQ ID NO: 14
AbA    GNVFSCSVMHEALHNHYTQKSLSLSPG    SEQ ID NO: 15
```

Figure 2

| mAb / DVD | EGFR (1-525) | | | | EGFRvIII | | | |
| --- | --- | --- | --- | --- | --- | --- | --- | --- |
| | $k_a$ (M$^{-1}$ s$^{-1}$) | $k_d$ (s$^{-1}$) | $K_D$ (M) | $K_D$ ratio (Ab1/variant Ab) | $k_a$ (M$^{-1}$ s$^{-1}$) | $k_d$ (s$^{-1}$) | $K_D$ (M) | $K_D$ ratio (Ab1/variant Ab) |
| Ab1 | 3.53E+03 | 8.02E-03 | 2.3E-06 | | 8.43E+04 | 7.93E-04 | 9.4E-09 | |
| Ab2 | 4.26E+05 | 1.71E-03 | 4.0E-09 | | 3.46E+06 | 1.32E-03 | 3.8E-10 | |
| AbK | 4.78E+03 | 7.92E-06 | 1.7E-09 | 1372.6 | 1.30E+05 | 7.75E-05 | 6.0E-10 | 15.8 |
| AbL | 5.65E+03 | 1.78E-05 | 3.1E-09 | 722.5 | 2.00E+05 | 6.95E-05 | 3.5E-10 | 27.1 |
| AbN | 4.84E+03 | 1.71E-05 | 3.5E-09 | 641.7 | 1.37E+05 | 1.03E-04 | 7.5E-10 | 12.5 |
| AbO | 5.25E+03 | 2.05E-05 | 3.9E-09 | 582.4 | 1.96E+05 | 5.22E-05 | 2.7E-10 | 35.2 |
| AbH | 7.90E+03 | 4.07E-05 | 5.2E-09 | 441.0 | 3.27E+05 | 4.89E-05 | 1.5E-10 | 63.1 |
| AbM | 3.84E+03 | 2.26E-05 | 5.9E-09 | 386.6 | 1.87E+05 | 1.18E-04 | 6.3E-10 | 14.9 |
| AbG | 6.80E+03 | 5.88E-05 | 8.6E-09 | 263.0 | 3.74E+05 | 7.44E-05 | 2.0E-10 | 47.2 |
| AbP | 3.58E+03 | 7.67E-05 | 2.1E-08 | 106.0 | 1.17E+05 | 1.35E-04 | 1.2E-09 | 8.2 |
| AbJ | 2.20E+03 | 8.27E-05 | 3.8E-08 | 60.5 | 3.18E+05 | 9.40E-05 | 3.0E-10 | 31.8 |
| AbB | 5.46E+03 | 1.19E-03 | 2.2E-07 | 10.5 | 7.83E+04 | 1.73E-04 | 2.2E-09 | 4.2 |
| AbA | 3.26E+03 | 7.31E-04 | 2.2E-07 | 10.1 | 7.61E+04 | 1.73E-04 | 2.3E-09 | 4.1 |
| AbF | 1.98E+03 | 8.31E-04 | 4.2E-07 | 5.4 | 8.36E+04 | 3.24E-04 | 3.9E-09 | 2.4 |
| AbD | | | 5.5E-07 | 4.1 | 1.41E+05 | 8.66E-04 | 6.1E-09 | 1.5 |
| AbE | 5.82E+03 | 3.22E-03 | 5.5E-07 | 4.1 | 1.93E+05 | 1.58E-03 | 8.2E-09 | 1.2 |
| AbC | 6.17E+03 | 3.67E-03 | 5.9E-07 | 3.8 | 2.20E+05 | 7.90E-04 | 3.6E-09 | 2.6 | poor fit, no kinetic info

Figure 3

SCC-15 (Ab1 Sensitive)

H292 (Ab1 Resistant)

A. Ab1 variant (Ab1v) VH library design

```
              1         2          3          4          5          6          7          8           9         10        1
      1234567890123456789012345a67890123456a78901234567890123456789012345678901234567890abc34567890123456890123456789012 31
VH4-4 QVQLQESGPGLVKPSGTLSLTCAVSGGSISSSNWWSWVRQPPGKGLEWIGEIYHSGSTNYNPSLKSRITISVDKSKNQFFLKLSSVTAADTAVYYCAR
Ab1vVH QVQLQESGPGLVKPSQTLSLTCTVSGYSISSDFAWNWIRQPPGKGLEWMGISYSGNTRYQPSLKSRITISRDTSKNQFFLKLNSVTAADTATYYCVTAGRGFPYNGQGTLVTVSS
Lib.                                  XXX                              XXX                                    XXXXXXX
                                      CDR1                             CDR2                                     CDR3
```

Figure 16A

B. Ab1 variant (Ab1v) VL library design

```
              1         2          3          4          5          6          7          8          9         10
      123456789012345678901234567890123456789012345678901234567890123456789012345678901234567890123456a
IGKV1-12 DIQMTQSPSSMSASVGDRVTITCRASQGISSWLAWYQQKPGKAPKLLIYAASSLQSGVPSRFSGSGSGTDFTLTISSLQPEDFATYYCQQANSFP
Ab1vVL   DIQMTQSPSSMSVSVGDRVTITCHSSQDINSNIGWLQQKPGKSFKGLIYHGTNLDDGVPSRFSGSGSGTDYTLTISSLQPEDFATYYCVQYAQFPWTFGGGTKLEIK
Lib.                           X XXXI                        X 2X XX                                    XXX
                               CDR1                          CDR2                                       CDR3
```

Figure 16B

ANTI-EGFR ANTIBODIES AND ANTIBODY DRUG CONJUGATES

RELATED APPLICATIONS

The present application is a divisional of U.S. patent application Ser. No. 15/349,692, filed on Nov. 11, 2016, which is a divisional of U.S. patent application Ser. No. 14/664,453, filed on Mar. 20, 2015, now U.S. Pat. No. 9,493,568, issued Nov. 15, 2016, which in turn claims priority to U.S. Provisional Patent Application Ser. No. 61/968,819, filed on Mar. 21, 2014, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Nov. 9, 2017, is named A103017_1020USD2_SL.txt and is 110,592 bytes in size.

BACKGROUND OF THE INVENTION

The human epidermal growth factor receptor (also known as HER-1 or Erb-B1, and referred to herein as "EGFR") is a 170 kDa transmembrane receptor encoded by the c-erbB protooncogene, and exhibits intrinsic tyrosine kinase activity (Modjtahedi et al., Br. J. Cancer 73:228-235 (1996); Herbst and Shin, Cancer 94:1593-1611 (2002)). SwissProt database entry P00533 provides the sequence of human EGFR. EGFR regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay et al., Ann. Oncology 14:1346-1363 (2003); Tsao and Herbst, Signal 4:4-9 (2003); Herbst and Shin, Cancer 94:1593-1611 (2002); Modjtahedi et al., Br. J. Cancer 73:228-235 (1996)).

Known ligands of EGFR include EGF, TGFA/TGF-alpha, amphiregulin, epigen/EPGN, BTC/betacellulin, epiregulin/EREG and HBEGF/heparin-binding EGF. Ligand binding by EGFR triggers receptor homo- and/or heterodimerization and autophosphorylation of key cytoplasmic residues. The phosphorylated EGFR recruits adapter proteins like GRB2 which in turn activate complex downstream signaling cascades, including at least the following major downstream signaling cascades: the RAS-RAF-MEK-ERK, PI3 kinase-AKT, PLCgamma-PKC, and STATs modules. This autophosphorylation also elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to cell proliferation. Ligand binding by EGFR may also activate the NF-kappa-B signaling cascade. Ligand binding also directly phosphorylates other proteins like RGS16, activating its GTPase activity and potentially coupling the EGF receptor signaling to G protein-coupled receptor signaling. Ligand binding also phosphorylates MUC1 and increases its interaction with SRC and CTNNB1/beta-catenin.

Overexpression of EGFR has been reported in numerous human malignant conditions, including cancers of the bladder, brain, head and neck, pancreas, lung, breast, ovary, colon, prostate, and kidney. (Atalay et al., Ann. Oncology 14:1346-1363 (2003); Herbst and Shin, Cancer 94:1593-1611 (2002); and Modjtahedi et al., Br. J. Cancer 73:228-235 (1996)). In many of these conditions, the overexpression of EGFR correlates or is associated with poor prognosis of the patients. (Herbst and Shin, Cancer 94:1593-1611 (2002); and Modjtahedi et al., Br. J. Cancer 73:228-235 (1996)). EGFR is also expressed in the cells of normal tissues, particularly the epithelial tissues of the skin, liver, and gastrointestinal tract, although at generally lower levels than in malignant cells (Herbst and Shin, Cancer 94:1593-1611 (2002)).

A significant proportion of tumors containing amplifications of the EGFR gene (i.e., multiple copies of the EGFR gene) also co-express a truncated version of the receptor (Wikstrand et al. (1998) J. Neurovirol. 4, 148-158) known as de2-7 EGFR, ΔEGFR, EGFRvIII, or Δ2-7 (terms used interchangeably herein) (Olapade-Olaopa et al. (2000) Br. J. Cancer. 82, 186-94). The rearrangement seen in the de2-7 EGFR results in an in-frame mature mRNA lacking 801 nucleotides spanning exons 2-7 (Wong et al. (1992) Proc. Natl. Acad. Sci. U.S.A. 89, 2965-9; Yamazaki et al. (1990) Jpn. J. Cancer Res. 81, 773-9; Yamazaki et al. (1988) Mol. Cell. Biol. 8, 1816-20; and Sugawa et al. (1990) Proc. Natl. Acad. Sci. U.S.A. 87, 8602-6). The corresponding EGFR protein has a 267 amino acid deletion comprising residues 6-273 of the extracellular domain and a novel glycine residue at the fusion junction (Sugawa et al., 1990). This deletion, together with the insertion of a glycine residue, produces a unique junctional peptide at the deletion interface (Sugawa et al., 1990).

EGFRvIII has been reported in a number of tumor types including glioma, breast, lung, ovarian and prostate (Wikstrand et al. (1997) Cancer Res. 57, 4130-40; Olapade-Olaopa et al. (2000) Br. J. Cancer. 82, 186-94; Wikstrand, et al. (1995) Cancer Res. 55, 3140-8; Garcia de Palazzo et al. (1993) Cancer Res. 53, 3217-20). While this truncated receptor does not bind ligand, it possesses low constitutive activity and imparts a significant growth advantage to glioma cells grown as tumor xenografts in nude mice (Nishikawa et al. (1994) Proc. Natl. Acad. Sci. U.S.A. 91, 7727-31) and is able to transform NIH3T3 cells (Batra et al. (1995) Cell Growth Differ. 6, 1251-9) and MCF-7 cells. The cellular mechanisms utilized by the de2-7 EGFR in glioma cells are not fully defined but are reported to include a decrease in apoptosis (Nagane et al. (1996) Cancer Res. 56, 5079-86) and a small enhancement of proliferation (Nagane et al., 1996). As expression of this truncated receptor is restricted to tumor cells it represents a highly specific target for antibody therapy.

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-EGFR antibodies and ADCs that can be used for therapeutic purposes in the treatment of cancer.

SUMMARY OF THE INVENTION

In certain aspects, the present invention provides for anti-EGFR antibodies and antibody drug conjugates (ADCs) that specifically bind to EGFRvIII.

In one embodiment, the invention features anti-human epidermal growth factor receptor (anti-hEGFR) antibodies, or antigen binding portions thereof, that bind to an epitope within the amino acid sequence CGADSYEMEEDGVRKC (SEQ ID NO: 45) or competes with a second anti-hEGFR antibody for binding to epidermal growth factor receptor variant III (EGFRvIII) (SEQ ID NO: 33) in a competitive binding assay, wherein the second anti-EGFR antibody comprises a heavy chain variable domain comprising the amino acid sequence set forth in SEQ ID NO: 1 and a light chain variable domain comprising the amino acid sequence set forth in SEQ ID NO: 5; binds to EGFR(1-525) (SEQ ID NO: 47) with a dissociation constant ($K_d$) of about $1 \times 10^{-6}$ M or less, as determined by surface plasmon resonance; and inhibits tumor growth in an in vivo human non-small-cell lung carcinoma (NSCLC) xenograft assay with a tumor growth inhibition % (TGI %) of at least about 50% relative to a human IgG antibody which is not specific for EGFR, wherein the human IgG antibody is administered in the NSCLC xenograft assay at the same dose and frequency as the anti-hEGFR antibody, or antigen binding portion thereof.

In certain embodiments of the invention, the antibodies, or antigen binding portions thereof, bind to EGFR (1-525) (SEQ ID NO: 47) with a $K_d$ of between about $1 \times 10^{-6}$ M and about $1 \times 10^{-10}$ M, as determined by surface plasmon resonance.

In other embodiments of the invention, the antibodies, or antigen binding portions thereof, bind to EGFR (1-525) (SEQ ID NO: 47) with a $K_d$ of between about $1 \times 10^{-6}$ M and about $1 \times 10^{-7}$ M, as determined by surface plasmon resonance.

In certain embodiments, the antibodies, or antigen binding portions thereof, of the invention bind to EGFRvIII (SEQ ID NO: 33) with a $K_d$ of about $8.2 \times 10^{-9}$ M or less, as determined by surface plasmon resonance. In further embodiments, the antibody, or antigen binding portion thereof, binds to EGFRvIII (SEQ ID NO: 33) with a $K_d$ of between about $8.2 \times 10^{-9}$ M and about $6.3 \times 10^{-10}$ M, as determined by surface plasmon resonance. In some embodiments, the antibody, or antigen binding portion thereof, binds to EGFRvIII (SEQ ID NO: 33) with a $K_d$ of between about $8.2 \times 10^{-9}$ M and about $2.0 \times 10^{-9}$ M, as determined by surface plasmon resonance.

In yet other embodiments of the invention, the antibodies, or antigen binding portions thereof, inhibit tumor growth by at least about 60% in an in vivo human non-small-cell lung carcinoma (NSCLC) xenograft assay relative to a human IgG antibody which is not specific for EGFR.

In certain embodiments, the invention features antibodies, or antigen binding portions thereof, that inhibits tumor growth by at least about 70% in an in vivo human non-small-cell lung carcinoma (NSCLC) xenograft assay relative to a human IgG antibody which is not specific for EGFR. In certain embodiments, the antibodies, or antigen binding portions thereof, inhibit tumor growth by at least about 80% in an in vivo human non-small-cell lung carcinoma (NSCLC) xenograft assay relative to a human IgG antibody which is not specific for EGFR.

In some embodiments, the antibodies, or antigen binding portions thereof, comprise a heavy chain CDR3 domain comprising the amino acid sequence set forth in SEQ ID NO: 12, a heavy chain CDR2 domain comprising the amino acid sequence set forth in SEQ ID NO: 11, and a heavy chain CDR1 domain comprising the amino acid sequence set forth in SEQ ID NO: 10; and a light chain CDR3 domain comprising the amino acid sequence set forth in SEQ ID NO: 8, a light chain CDR2 domain comprising the amino acid sequence set forth in SEQ ID NO: 7, and a light chain CDR1 domain comprising the amino acid sequence set forth in SEQ ID NO: 6. In yet another embodiment, the antibodies, or antigen binding portions thereof, comprise a heavy chain variable region comprising the amino acid sequence set forth in SEQ ID NO: 9, and a light chain variable region comprising the amino acid sequence set forth in SEQ ID NO: 5. In other embodiments, the antibodies, or antigen binding portions thereof, comprise a heavy chain constant region comprising the amino acid sequence set forth in SEQ ID NO: 41 and/or a light chain constant region comprising the amino acid sequence set forth in SEQ ID NO: 43. In a further embodiment, the antibodies, or antigen binding portions thereof, comprise a heavy chain comprising the amino acid sequence set forth in SEQ ID NO: 15, and a light chain comprising the amino acid sequence set forth in SEQ ID NO: 13. In another embodiment, the the antibodies, or antigen binding portions thereof, are conjugated to an auristatin.

The invention also provides, in certain embodiments, isolated nucleic acids encoding an antibodies, or antigen binding portions thereof, like that described herein.

The invention also includes, in certain embodiments, anti-hEGFR antibodies, or antigen binding portions thereof, comprising a light chain CDR3 domain comprising the amino acid sequence set forth in SEQ ID NO: 40, a light chain CDR2 domain comprising the amino acid sequence set forth in SEQ ID NO: 39, and a light chain CDR1 domain comprising the amino acid sequence set forth in SEQ ID NO: 38; and a heavy chain CDR3 domain comprising the amino acid sequence set forth in SEQ ID NO: 37, a heavy chain CDR2 domain comprising the amino acid sequence set forth in SEQ ID NO: 36, and a heavy chain CDR1 domain comprising the amino acid sequence set forth in SEQ ID NO: 35.

In certain embodiments, the invention features anti-hEGFR antibodies, or antigen binding portions thereof, comprising a heavy chain variable region comprising an amino acid sequence selected from the group consisting of 50, 52, 54, 56, 58, 60, 62, 64, 66, 68, 70, 72, 74, 76, and 78; and a light chain variable region comprising an amino acid sequence selected from the group consisting of 51, 53, 55, 57, 59, 61, 63, 65, 67, 69, 71, 73, 75, 77, and 79.

In other embodiments, the invention includes anti-hEGFR antibodies, or antigen binding portions thereof, comprising a heavy chain CDR set (CDR1, CDR2, and CDR3) selected from the group consisting of SEQ ID NOs: 10, 11, and 12; SEQ ID NOs: 16, 17, and 18; SEQ ID NOs: 10, 11, and 19; SEQ ID NOs: 20, 11, and 12; SEQ ID NOs: 21, 3, and 22; SEQ ID NOs: 16, 17, and 19; SEQ ID NOs: 2, 3, and 4; SEQ ID NOs: 10, 3, and 12; SEQ ID NOs: 80, 11, and 18; SEQ ID NOs: 80, 3, and 18; SEQ ID NOs: 20, 3, and 12; SEQ ID NOs: 80, 11, and 12; and SEQ ID NOs: 81, 11, and 22; and a light chain CDR set (CDR1, CDR2, and CDR3) selected from the group consisting of SEQ ID NOs: 6, 7, and 8; SEQ ID NOs: 23, 24, and 25; SEQ ID NOs: 26, 27, and 28; SEQ ID NOs: 29, 30, and 31; SEQ ID NOs: 6, 7, and 84; SEQ ID NOs: 82, 83, and 31; and SEQ ID NOs: 82, 27, and 85, wherein the antibodies, or antigen binding portions thereof, does not comprise both the heavy chain CDR set of SEQ ID NOs: 2, 3, and 4, and the light chain CDR set of SEQ ID NOs: 6, 7, and 8. In some embodiments, the antibodies, or antigen binding portions thereof, comprises a heavy chain constant region comprising the amino acid sequence set forth in SEQ ID NO: 41 and/or a light chain constant region comprising the amino acid sequence set forth in SEQ ID NO: 43.

In some embodiments of the invention, the antibodies, or antigen binding portions thereof, comprise a heavy chain immunoglobulin constant domain selected from the group consisting of a human IgG constant domain, a human IgM constant domain, a human IgE constant domain, and a human IgA constant domain. In some embodiments, the IgG constant domain is selected from the group consisting of an IgG1 constant domain, an IgG2 constant domain, an IgG3 constant domain, and an IgG4 constant domain. In other embodiments, the antibody is a multispecific antibody.

In other embodiments of the invention, the antibodies, or antigen binding portions thereof, comprise a Fab, a Fab', a F(ab')2, a Fv, a disulfide linked Fv, an scFv, a single domain antibody, and a diabody.

In yet other embodiments of the invention, the antibodies, or antigen binding portions thereof, are conjugated to an imaging agent. In certain embodiments of the invention, the imaging agent is selected from the group consisting of a radiolabel, an enzyme, a fluorescent label, a luminescent label, a bioluminescent label, a magnetic label, and biotin. In other embodiments of the invention, the radiolabel is indium. In yet other embodiments, the invention includes a pharmaceutical composition comprising the antibody, or antigen binding portion thereof, and a pharmaceutically acceptable carrier.

The invention also includes, in some embodiments, an antibody drug conjugate (ADC) comprising the antibody, or antigen binding portion thereof, described herein, conjugated to at least one drug. In certain embodiments, the antibody is an anti-human epidermal growth factor receptor (anti-hEGFR) antibody, or antigen binding portion thereof, that binds to an epitope within the amino acid sequence CGADSYEMEEDGVRKC (SEQ ID NO: 45) or competes with a second anti-hEGFR antibody for binding to epidermal growth factor receptor variant III (EGFRvIII) (SEQ ID NO: 33) in a competitive binding assay, wherein the second anti-EGFR antibody comprises a heavy chain variable domain comprising the amino acid sequence set forth in SEQ ID NO: 1 and a light chain variable domain comprising the amino acid sequence set forth in SEQ ID NO: 5; binds to EGFR(1-525) (SEQ ID NO: 47) with a dissociation constant ($K_d$) of about $1 \times 10^{-6}$ M or less, as determined by surface plasmon resonance; and inhibits tumor growth in an in vivo human non-small-cell lung carcinoma (NSCLC) xenograft assay with a tumor growth inhibition % (TGI %) of at least about 50% relative to a human IgG antibody which is not specific for EGFR, wherein the human IgG antibody is administered in the NSCLC xenograft assay at the same dose and frequency as the anti-hEGFR antibody, or antigen binding portion thereof. In one embodiment of the invention, the at least one drug is selected from the group consisting of an anti-apoptotic agent, a mitotic inhibitor, an anti-tumor antibiotic, an immunomodulating agent, a nucleic acid for gene therapy, an alkylating agent, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In certain embodiments, the mitotic inhibitor is a dolastatin, an auristatin, a maytansinoid, and a plant alkaloid. In certain embodiments, the drug is a dolastatin, an auristatin, a maytansinoid, and a plant alkaloid. An example of an auristatin is monomethylaurisatin F (MMAF) or monomethyauristatin E (MMAE). Examples of maytansinoids include, but are not limited to, DM1, DM2, DM3, and DM4. In certain embodiments, the anti-tumor antibiotic is selected from the group consisting of an actinomycine, an anthracycline, a calicheamicin, and a duocarmycin. In certain embodiments, the actinomycine is a pyrrolobenzodiazepine (PBD).

The invention also includes, in some embodiments, an ADC comprising an anti-EGFR antibody conjugated to an auristatin, wherein the antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10; and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In one embodiment, the antibody comprises a heavy chain variable region comprising the amino acid sequence set forth in SEQ ID NO: 9, and a light chain variable region comprising the amino acid sequence of SEQ ID NO: 5. In yet another embodiment, the invention includes antibodies, or antigen binding portions thereof comprising a heavy chain comprising the amino acid sequence set forth in SEQ ID NO: 15, and a light chain comprising the amino acid sequence of SEQ ID NO: 13.

The invention also includes, in some embodiments, an ADC comprising an anti-EGFR antibody conjugated to at least one drug (including, but not limited to, MMAE), wherein between 1 to 8 molecules of the drug are conjugated to the antibody. In one embodiment, 1 to 4 molecules of the drug are conjugated to the antibody of the ADC. In one embodiment, 2 to 4 molecules of the drug are conjugated to the antibody of the ADC.

The invention also includes, in some embodiments, an ADC comprising an anti-EGFR antibody conjugated to at least one drug, wherein the drug is conjugated via a maleimidocaproyl, valine-citrulline linker. In a further embodiment, the drug is conjugated to the antibody via a maleimidocaproyl, valine-citrulline, p-aminobenzyloxycarbamyl (PABA) linker.

The invention also includes, in some embodiments, an ADC comprising an anti-EGFR IgG1 antibody covalently linked to monomethylauristatin E (MMAE) via a linker (e.g., maleimidocaproyl, valine-citrulline). In certain embodiments, the antibody comprises a heavy chain variable region comprising the amino acid sequence set forth in SEQ ID NO: 9, and comprises a light chain variable region comprising the amino acid sequence set forth in SEQ ID NO: 5. In certain embodiments, 1 to 4 molecules of MMAE are linked to the antibody.

The invention also includes, in some embodiments, an ADC comprising an anti-EGFR IgG1 antibody covalently linked to maleimidocaproyl, valine-citrulline, p-aminobenzyloxycarbamyl-monomethylauristatin E (mc-vc-PABA-MMAE), wherein the antibody comprises a heavy chain variable region comprising the amino acid sequence set forth in SEQ ID NO: 9, and comprises a light chain variable region comprising the amino acid sequence set forth in SEQ ID NO: 5, and wherein 1 to 4 molecules of MMAE are linked to the antibody. In certain embodiments, the antibody comprises a heavy chain comprising the amino acid sequence set forth in SEQ ID NO: 15, and comprises a light chain comprising the amino acid sequence set forth in SEQ ID NO: 13. In certain embodiments, 2 to 4 molecules of MMAE are linked to the antibody. In certain embodiments, the EGFR antibody is linked to mc-vc-PABA-MMAE as depicted in FIG. 11.

The invention also includes, in some embodiments, an EGFR-directed ADC comprising an IgG1 antibody specific for human EGFR, MMAE, and a linker that covalently attaches MMAE to the antibody. In certain embodiments, the antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10; and comprises a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In one embodiment, the antibody comprises a heavy chain variable region comprising the amino acid sequence set forth in SEQ ID NO: 9, and a light chain variable region comprising the amino acid sequence of SEQ ID NO: 5. In yet another embodiment, the invention includes antibodies, or antigen binding portions thereof comprising a heavy chain comprising the amino acid sequence set forth in SEQ ID NO: 15, and a light chain comprising the amino acid sequence of SEQ ID NO: 13.

In yet other embodiments, the invention includes a pharmaceutical composition comprising an ADC mixture comprising a plurality of the ADC described herein, and a pharmaceutically acceptable carrier. In certain embodiments, the ADC mixture has an average drug to antibody ratio (DAR) of 2 to 4. In other embodiments the ADC mixture comprises ADCs each having a DAR of 2 to 8. In certain embodiments, the ADC mixture has an average drug to antibody (DAR) of about 2.4 to about 3.6.

In certain embodiments, the invention includes methods for treating a subject having cancer, comprising administering the pharmaceutical composition described herein to the subject, such that the subject having cancer is treated. In one embodiment, the cancer is selected from the group consisting of breast cancer, lung cancer, a glioblastoma, prostate cancer, pancreatic cancer, colon cancer, head and neck cancer, and kidney cancer. In one embodiment, the cancer is selected from the group consisting of breast cancer, lung cancer, a glioblastoma, prostate cancer, pancreatic cancer, colon cancer, colorectal cancer, head and neck cancer, mesothelioma, kidney cancer, squamous cell carcinoma, triple negative breast cancer, and non-small cell lung cancer. In one embodiment, the cancer is breast cancer. In one embodiment, the cancer is lung cancer. In one embodiment, the cancer is prostate cancer. In one embodiment, the cancer is pancreatic cancer. In one embodiment, the cancer is colon cancer. In one embodiment, the cancer is head and neck cancer. In one embodiment, the cancer is kidney cancer. In one embodiment, the cancer is colorectal cancer. In one embodiment, the cancer is mesothelioma. In one embodiment, the cancer is squamous cell carcinoma. In one embodiment, the cancer is triple negative breast cancer. In one embodiment, the cancer is non-small cell lung cancer. In certain embodiments, the squamous cell carcinoma is squamous lung cancer or squamous head and neck cancer.

In yet another embodiment, the cancer contains amplifications of EGFR or overexpresses EGFR. In certain embodiments, the cancer is characterized as having EGFR overexpression. In certain embodiments, the cancer is characterized as having EGFR amplification.

The invention further includes, in certain embodiments, methods for inhibiting or decreasing solid tumor growth in a subject having a solid tumor, comprising administering the pharmaceutical composition described herein to the subject having the solid tumor, such that the solid tumor growth is inhibited or decreased. In certain embodiments, the solid tumor is characterized as having EGFR overexpression. In certain embodiments, the solid tumor is characterized as having EGFR amplification.

In one embodiment of the invention, the invention provides for methods for inhibiting or decreasing solid tumor growth in a subject having a solid tumor, comprising administering to the subject having the solid tumor an effective amount of the antibody or ADC described herein, such that the solid tumor growth is inhibited or decreased.

In certain embodiments, the solid tumor is an EGFR expressing solid tumor or an EGFRvIII positive solid tumor. In other embodiments, the solid tumor is a non-small cell lung carcinoma or a glioblastoma. In other embodiments, the solid tumor is a squamous cell carcinoma.

In one embodiment of the invention, the invention provides for a method for treating a subject having cancer, comprising administering an effective amount of an ADC comprising an anti-EGFR antibody, or antigen binding portion thereof, conjugated to at least one auristatin, wherein the anti-EGFR antibody, or antigen binding portion thereof, is an IgG isotype; comprises a heavy chain variable region comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10; and comprises a light chain variable region comprising a CDR3 domain comprising the amino acid sequence set forth in SEQ ID NO: 8, a CDR2 domain comprising the amino acid sequence set forth in SEQ ID NO: 7, and a CDR1 domain comprising the amino acid sequence set forth in SEQ ID NO: 6. In certain embodiments, the antibody, or antigen binding portion thereof, is linked to mc-vc-PABA-MMAE.

In certain embodiments, the invention includes methods for treating a subject having cancer, comprising administering the pharmaceutical composition described herein to the subject in combination with an additional agent or additional therapy. In certain embodiments, the additional agent is selected from the group consisting of an anti-PD1 antibody (e.g., pembrolizumab (Keytruda®) or nivolumab), an anti-CTLA-4 antibody (e.g., ipilimumab), ibrutinib, duvelisib, idelalisib, venetoclax, and temozolomide. In certain embodiments, the additional therapy is radiation. In certain embodiments, the additional agent is an anti-PD1 antibody (e.g., pembrolizumab (Keytruda®) or nivolumab). In certain embodiments, the additional agent is an anti-CTLA-4 antibody (e.g., ipilimumab). In certain embodiments, the additional agent is ibrutinib. In certain embodiments, the additional agent is duvelisib. In certain embodiments, the additional agent is idelalisib. In certain embodiments, the additional agent is venetoclax. In certain embodiments, the additional agent is temozolomide.

The invention also provides, in certain embodiments, isolated nucleic acids encoding an antibodies, or antigen binding portions thereof, like that described herein. Further, the invention includes a vector comprising the nucleic acid, and a host cell, e.g., a prokaryotic or a eukaryotic cell (e.g., animal cell, a protest cell, a plant cell, and a fungal cell) comprising the vector. In embodiment of the invention, the animal cell is selected from the group consisting of a mammalian cell, an insect cell, and an avian cell. In one embodiment, the mammalian cell is selected from the group consisting of a CHO cell, a COS cell, and an Sp2/0 cell.

In certain embodiments, the invention features anti-hEGFR Antibody Drug Conjugates (ADC) comprising an anti-hEGFR antibody conjugated to an auristatin, wherein the antibody comprises a heavy chain CDR3 domain comprising the amino acid sequence of SEQ ID NO: 12, a heavy chain CDR2 domain comprising the amino acid sequence of SEQ ID NO: 11, and a heavy chain CDR1 domain comprising the amino acid sequence of SEQ ID NO: 10; and a light chain CDR3 domain comprising the amino acid sequence of SEQ ID NO: 8, a light chain CDR2 domain comprising the amino acid sequence of SEQ ID NO: 7, and a light chain CDR1 domain comprising the amino acid sequence of SEQ ID NO: 6. In one embodiment, the antibody comprises a heavy chain variable region comprising the amino acid sequence set forth in SEQ ID NO: 9, and a light chain variable region comprising the amino acid sequence of SEQ ID NO: 5. In yet another embodiment, the antibody comprises an IgG heavy chain immunoglobulin constant domain. In still another embodiment, the IgG is an IgG1 or an IgG4 heavy chain immunoglobulin constant domain.

In one embodiment, the invention includes an ADC, wherein the auristatin is monomethylaurisatin F (MMAF) or monomethyauristatin E (MMAE). In one embodiment, the invention includes an ADC, wherein the auristatin is monomethylaurisatin F (MMAF). In one embodiment, the invention includes an ADC, wherein the auristatin is monomethyauristatin E (MMAE).

In a further embodiment, the invention includes a heavy chain comprising the amino acid sequence of SEQ ID NO: 15, and comprises a light chain comprising the amino acid sequence of SEQ ID NO: 13.

In still another embodiment of the invention, the anti-EGFR antibody is covalently linked to the auristatin by a linker comprising maleimidocaproyl, valine-citrulline, p-aminobenzylalcohol (mc-vc-PABA).

In one embodiment, the invention includes an ADC comprising an anti-EGFR and a radiolabel, e.g. indium.

In one embodiment, an anti-EGFR antibody described herein is covalently linked to at least one pyrrolobenzodiazepine (PBD). In certain embodiments, the anti-EGFR antibody disclosed herein is linked to a PBD as described in FIG. 21 (i.e., SGD-1882).

In some embodiments, the invention features pharmaceutical compositions comprising the ADC described herein, and a pharmaceutically acceptable carrier In certain embodiments, the invention features pharmaceuticals composition comprising an ADC mixture comprising the ADC described herein, wherein the average drug to antibody ratio (DAR) range in the ADC mixture is 2 to 4. In certain embodiments, the average drug to antibody ratio (DAR) range in the ADC mixture is 2.4 to 3.6.

In one embodiment, the invention features pharmaceutical compositions comprising an ADC mixture comprising anti-hEGFR Antibody Drug Conjugates (ADCs), and a pharmaceutically acceptable carrier, wherein the ADC mixture has an average Drug to Antibody Ratio (DAR) of 2 to 4, and wherein said ADC comprises monomethyauristatin E (MMAE) conjugated to an anti-hEGFR antibody comprising a heavy chain CDR3 domain comprising the amino acid sequence of SEQ ID NO: 12, a heavy chain CDR2 domain comprising the amino acid sequence of SEQ ID NO: 11, and a heavy chain CDR1 domain comprising the amino acid sequence of SEQ ID NO: 10; and a light chain CDR3 domain comprising the amino acid sequence of SEQ ID NO: 8, a light chain CDR2 domain comprising the amino acid sequence of SEQ ID NO: 7, and a light chain CDR1 domain comprising the amino acid sequence of SEQ ID NO: 6 In one embodiment, the heavy chain variable region of the antibody comprises the amino acid sequence set forth in SEQ ID NO: 9, and the light chain variable region of the anti-EGFR antibody comprises the amino acid sequence set forth in SEQ ID NO: 5.

In other embodiments of the invention, the antibody comprises an IgG heavy chain immunoglobulin constant domain. In further embodiments, the invention includes an antibody having an IgG1 or an IgG4 heavy chain immunoglobulin constant domain. In one embodiment, the invention includes an antibody is an IgG1 isotype.

In yet another embodiment, the invention includes antibodies comprising a heavy chain comprising the amino acid sequence set forth in SEQ ID NO: 15, and a light chain comprising the amino acid sequence of SEQ ID NO: 13. In one embodiment, the invention features having an MMAE which is conjugated to the antibody by a maleimidocaproyl, val-cit, PABA linker.

In one embodiment of the invention, the invention provides methods for treating a subject having cancer, comprising administering a pharmaceutical composition comprising an antibody or ADC described herein to the subject, such that the subject having cancer is treated. In one embodiment, the cancer is selected from the group consisting of breast cancer, lung cancer, a glioblastoma, prostate cancer, pancreatic cancer, colon cancer, head and neck cancer, and kidney cancer. In one embodiment, the cancer is selected from the group consisting of breast cancer, lung cancer, a glioblastoma, prostate cancer, pancreatic cancer, colon cancer, colorectal cancer, head and neck cancer, mesothelioma, kidney cancer, squamous cell carcinoma, triple negative breast cancer, and non-small cell lung cancer. In yet another embodiment, the cancer contains amplifications of EGFR or overexpresses EGFR. In one embodiment, the squamous cell carcinoma is squamous lung cancer or squamous head and neck cancer. In one embodiment, the cancer is an EGFR overexpressing cancer. In one embodiment, the cancer is characterized as EGFR amplified. In one embodiment, the cancer is breast cancer. In one embodiment, the cancer is lung cancer. In one embodiment, the cancer is prostate cancer. In one embodiment, the cancer is pancreatic cancer. In one embodiment, the cancer is colon cancer. In one embodiment, the cancer is head and neck cancer. In one embodiment, the cancer is kidney cancer. In one embodiment, the cancer is colorectal cancer. In one embodiment, the cancer is mesothelioma. In one embodiment, the cancer is squamous cell carcinoma. In one embodiment, the cancer is triple negative breast cancer. In one embodiment, the cancer is non-small cell lung cancer. In certain embodiments, the squamous cell carcinoma is squamous lung cancer or squamous head and neck cancer.

In addition, in certain embodiments, the invention provides methods for inhibiting or decreasing solid tumor growth in a subject having a solid tumor, said method comprising administering the pharmaceutical composition described herein to the subject having the solid tumor, such that the solid tumor growth is inhibited or decreased. In one embodiment, the solid tumor is a non-small cell lung carcinoma or a glioblastoma. In yet another embodiment, the solid tumor is an EGFRvIII positive tumor or an EGFR-expressing solid tumor. In yet another embodiment, the solid tumor is an EGFR overexpressing solid tumor. In yet another embodiment, the solid tumor is an EGFR amplified tumor. In one embodiment, the solid tumor is a non-small cell lung carcinoma having amplified EGFR. In one embodiment, the solid tumor is a non-small cell lung carcinoma having EGFR overexpression. In one embodiment, the solid tumor is a glioblastoma having amplified EGFR. In one embodiment, the solid tumor is a glioblastoma having EGFR overexpression.

In certain embodiments, the invention provides combination therapies whereby the pharmaceutical compositions described herein are administered to a subject in need thereof, (e.g., a subject having cancer or a solid tumor). The pharmaceutical compositions described herein may be administered at the same time as, prior to, or following administration of an additional agent or additional therapy. In certain embodiments, the additional agent is selected from the group consisting of an anti-PD1 antibody, an anti-CTLA-4 antibody, temozolomide, a bcl-xl inhibitor, and a nicotinamide phosphoribosyltransferase (NAMPT) inhibitor. In yet other embodiments, the additional agent is a chemotherapeutic agent. In certain embodiments, the additional therapy is radiation. In other embodiments, the additional agent is ibrutinib (Imbruvica®, Pharmacyclics). In other embodiments, the additional agent is duvelisib. In other embodiments, the additional agent is idelalisib (Zydelig®, Gilead Sciences, Inc.). In other embodiments, the additional agent is venetoclax (ABT-199/GDC-0199, AbbVie, Inc.). In certain embodiments, the additional agent is an anti-PD1 antibody (e.g., pembrolizumab (Keytruda®) or nivolumab). In certain embodiments, the additional agent is an anti-CTLA-4 antibody (e.g., ipilimumab). In certain embodiments, the additional agent is temozolomide.

In certain embodiments, the invention features a chimeric antigen receptor (CAR) comprising antigen binding regions, e.g. CDRs, of the antibodies described herein or an scFv described herein. In certain embodiments, the invention features a CAR comprising a variable heavy light chain comprising a CDR3 domain comprising the amino acid sequence set forth in SEQ ID NO: 40, a CDR2 domain comprising the amino acid sequence set forth in SEQ ID NO: 39, and a CDR1 domain comprising the amino acid sequence set forth in SEQ ID NO: 38; and a heavy chain variable region comprising a CDR3 domain comprising the amino acid sequence set forth in SEQ ID NO: 37, a CDR2 domain comprising the amino acid sequence set forth in SEQ ID NO: 36, and a CDR1 domain comprising the amino acid sequence set forth in SEQ ID NO: 35.

In certain embodiments, the invention features a CAR comprising a variable heavy light chain comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10; and a heavy chain variable region comprising a CDR3 domain comprising the amino acid sequence set forth in SEQ ID NO: 8, a CDR2 domain comprising the amino acid sequence set forth in SEQ ID NO: 7, and a CDR1 domain comprising the amino acid sequence set forth in SEQ ID NO: 6.

BRIEF DESCRIPTION OF THE DRAWINGS

FIG. 1 provides the variable heavy (VH) and variable light (VL) chain region amino acid sequences of Ab1 (SEQ ID NOs: 1 and 5) and AbA (SEQ ID NOs: 9 and 5). CDR sequences within the VH and VL regions are boxed, and differences between the Ab1 VH sequence and the AbA VH sequence are shaded.

FIG. 2 describes the full length light and heavy chains for Ab1 (SEQ ID NOs: 13 and 14) and AbA (SEQ ID NOs: 13 and 15). Differences between the Ab1 sequence and the AbA sequence in the heavy chain are highlighted.

FIG. 3 provides a table summarizing the Biacore binding assay affinity measurements for multiple Ab1 variant antibodies in comparison to Ab1 and Ab2. EGFR (1-525) and EGFRvIII were used in the binding analysis. $k_a$ ($M^{-1}$ $s^{-1}$) as described in FIG. 3 refers to the rate constant for association of an antibody to the antigen to form the antibody/antigen complex, $k_d$ ($s^{-1}$) refers to the off rate constant for dissociation of an antibody from the antibody/antigen complex, and the $K_d$ (M) refers to the equilibrium dissociation constant rate.

FIG. 7A provides results showing the ability of Ab1, Ab2, and the Ab1 variant antibodies to inhibit EGF-mediated tyrosine phosphorylation of EGFR in SCC-15 cells. FIG. 7B provides results showing the ability of Ab1, Ab2, and the Ab1 variant antibodies to inhibit EGF-mediated tyrosine phosphorylation of EGFR in H292 cells.

FIGS. 12-1 and 12-2 provide results from hydrophobic interaction chromatography (HIC) analysis of the purification of AbA-vcMMAE.

FIGS. 13-1 and 13-2 provide results from size exclusion chromatography (SEC) analysis of AbA-vcMMAE.

FIG. 14A depicts results from a mouse xenograft inhibition assay comparing the inhibition of tumor growth in NCI-H1703 cells from a human NSCLC carcinoma xenograft demonstrating enhanced inhibition of AbA-vcMMAE compared to Ab1 and an Ab1-mcMMAF ADC.

FIG. 14B depicts results from a mouse xenograft inhibition assay comparing the inhibition of tumor growth in EBC-1 cells from a human NSCLC carcinoma xenograft demonstrating an enhanced inhibition of AbA-vcMMAE compared to Ab1 and Ab1-mcMMAF ADC. Arrows indicate time points of administration of the antibody.

FIG. 15A shows results of a mouse xenograft inhibition assay comparing the inhibition of tumor growth in NCI-H292 cells demonstrating an enhanced inhibition by purified AbA-vcMMAE (AbA-vcMMAEp) and AbA-vcMMAE compared to Ab1-vcMMAE purified (Ab1-vcMMAEp), Ab1-vcMMAE, Ab1-mcMMAF ADC purified (Ab1-mcMMAFp), and Ab1-mcMMAF (versus three controls). FIG. 15B shows results of a mouse xenograft inhibition assay comparing the inhibition of tumor growth in NCI-H292 cells demonstrating enhanced inhibition activity of AbA-vcMMAE compared to purified AbA-vcMMAE (AbA-vcMMAEp) and AbA-vcMMAE compared to purified Ab1-vcMMAE (Ab1-vcMMAEp), Ab1-vcMMAE, Ab1-mcMMAF, and Ab1-mcMMAFp. Doses of the molecules in FIGS. 15A and B are indicated in parentheses, i.e., 3 mg/kg or 6 mg/kg. Arrows indicate time points of administration of the antibody or ADC. Control 2 in FIG. 15 represents a negative control which is an anti-tetanus toxin antibody which does not bind to EGFR.

FIGS. 16A and 16B provide the amino acid sequences of the Ab1 variant variable heavy (VH) library design (FIG. 16A) and the Ab1 variant variable light (VL) library design (FIG. 16B).

FIGS. 20A and 20B graphically depict results from a single-photon emission computed tomography (SPECT) imaging assay comparing the efficacy of antibody uptake by EGFR expressing tumors in two tumor models (SW48 (FIG. 20A) and EBC1 (FIG. 20B) tumor models, respectively) using AbA, Ab1, or a control antibody labelled with $^{111}$In.

DETAILED DESCRIPTION OF THE INVENTION

Figure 4:
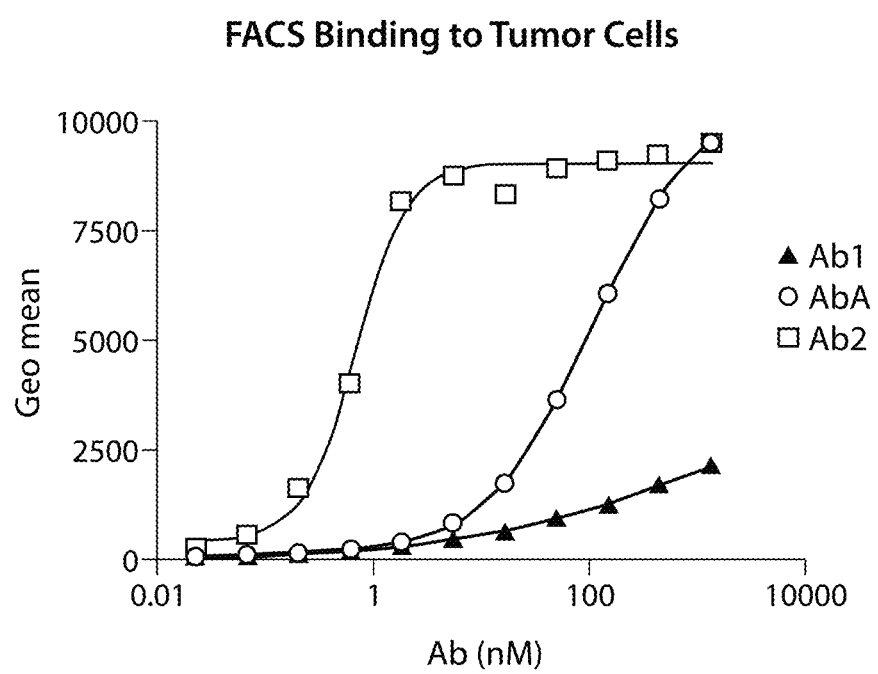
FIG. 4 provides a graphic summary of a FACS analysis showing that AbA had improved binding to A431 tumor cells (human squamous carceinoma cells) over Ab1, but a lower binding affinity in comparison to Ab2.

Various aspects of the invention relate to anti-EGFR antibodies and antibody fragments, anti-EGFR ADCs, and pharmaceutical compositions thereof, as well as nucleic acids, recombinant expression vectors and host cells for making such antibodies and fragments. Methods of using the antibodies and ADCs described herein to detect human EGFR, to inhibit human EGFR activity (in vitro or in vivo), and to treat cancers such as epithelial cancers, breast cancer, colorectal cancer, head and neck cancers (e.g. glioblastomas), lung cancer, kidney cancer, pancreatic cancer, mesothelioma, squamous cell carcinoma (e.g., squamous lung cancer or squamous head and neck cancer), triple negative breast cancer, non-small cell lung cancer, and prostate cancer are also encompassed by the invention.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "anti-Epidermal Growth Factor (EGF) Receptor antibody" or "anti-EGFR antibody", used interchangeably herein, refer to an antibody that specifically binds to EGFR. An antibody "which binds" an antigen of interest, i.e., EGFR, is one capable of binding that antigen with sufficient affinity such that the antibody is useful in targeting a cell expressing the antigen. In a preferred embodiment, the antibody specifically binds to human EGFR (hEGFR). Examples of anti-EGFR antibodies are disclosed in Example 1 below. Unless otherwise indicated, the term "anti-EGFR antibody" is meant to refer to an antibody which binds to wild type EGFR or any variant of EGFR, such as EGFRvIII.

The amino acid sequence of wild type human EGFR is provided below as SEQ ID NO: 32, where the signal peptide (amino acid residues 1-24) are underlined, and the amino acid residues of the extracellular domain (ECD, amino acid residues 25-645) are highlighted in bold. A truncated wild type ECD of the EGFR (also referred to herein as EGFR (1-525)) corresponds to SEQ ID NO: 47 and is equivalent to amino acids 1-525 of SEQ ID NO: 32. The mature form of wild type EGFR corresponds to the protein without the signal peptide, i.e., amino acid residues 25 to 1210 of SEQ ID NO: 32.

```
                                          (SEQ ID NO: 32)
  1 mrpsgtagaa llallaalcp asraleekkv cqgtsnkltq lgtfedhfls lqrmfnncev 61 vlgnleityv qrnydlsflk tiqevagyvl ialntverip lenlqiirgn myyensyala 121 vlsnydankt glkelpmrnl qeilhgavrf snnpalcnve siqwrdivss dflsnmsmdf 181 qnhlgscqkc dpscpngscw gageencqkl tkiicaqqcs grcrgkspsd cchnqcaagc 241 tgpresdclv crkfrdeatc kdtcpplmly npttyqmdvn pegkysfgat cvkkcprnyv 301 vtdhgscvra cgadsyemee dgvrkckkce gpcrkvcngi gigefkdsls inatnikhfk 361 nctsisgdlh ilpvafrgds fthtppldpq eldilktvke itgflliqaw penrtdlhaf 421 enleiirgrt kqhgqfslav vslnitslgl rslkeisdgd viisgnknlc yantinwkkl 481 fgtsgqktki isnrgensck atgqvchalc spegcwgpep rdcvscrnvs rgrecvdkcn
```

```
541  llegeprefv enseciqchp eclpqamnit ctgrgpdnci
     qcahyidgph cvktcpagvm
601  genntlvwky adaghvchlc hpnctygctg pglegcptng
     pkipsiatgm vgallllvv
661  algiglfmrr rhivrkrtlr rllqerelve pltpsgeapn
     qallrilket efkkikvlgs
721  gafgtvykgl wipegekvki pvaikelrea tspkankeil
     deayvmasvd nphvcrllgi
781  cltstvqlit qlmpfgclld yvrehkdnig sqyllnwcvq
     iakgmnyled rrlvhrdlaa
841  rnvlvktpqh vkitdfglak llgaeekeyh aeggkvpikw
     malesilhri ythqsdvwsy
901  gvtvwelmtf gskpydgipa seissilekg erlpqppict
     idvymimvkc wmidadsrpk
961  freliiefsk mardpqrylv iqgdermhlp sptdsnfyra
     lmdeedmddv vdadeylipq
1021 qgffsspsts rtpllsslsa tsnnstvaci drnglqscpi
     kedsflqrys sdptgalted
1081 siddtflpvp eyinqsvpkr pagsvqnpvy hnqplnpaps
     rdphyqdphs tavgnpeyln
1141 tvqptcvnst fdspahwaqk gshqisldnp dyqqdffpke
     akpngifkgs taenaeylrv
1201 apqssefiga
```

The amino acid sequence of the ECD of human EGFR is provided below as SEQ ID NO: 34, and includes the signal sequence (underlined).

```
                                      (SEQ ID NO: 34)
  1  mrpsgtagaa llallaalcp asraleekkv cqgtsnkltq
     lgtfedhfls lqrmfnncev
 61  vlgnleityv qrnydlsflk tiqevagyvl ialntverip
     lenlqiirgn myyensyala
121  vlsnydankt glkelpmrnl qeilhgavrf snnpalcnve
     siqwrdivss dflsnmsmdf
181  qnhlgscqkc dpscpngscw gageencqkl tkiicaqqcs
     grcrgkspsd cchnqcaagc
241  tgpresdclv crkfrdeatc kdtcpplmly npttyqmdvn
     pegkysfgat cvkkcprnyv
301  vtdhgscvra cgadsyemee dgvrkckkce gpcrkvcngi
     gigefkdsls inatnikhfk
361  nctsisgdlh ilpvafrgds fthtppldpq eldilktvke
     itgflliqaw penrtdlhaf
```

```
421  enleiirgrt kqhgqfslav vslnitslgl rslkeisdgd
     viisgnknlc yantinwkkl
481  fgtsgqktki isnrgensck atgqvchalc spegcwgpep
     rdcvscrnvs rgrecvdkcn
541  llegeprefv enseciqchp eclpqamnit ctgrgpdnci
     qcahyidgph cvktcpagvm
601  genntlvwky adaghvchlc hpnctygctg pglegcptng
     pkips
```

Figure 17:
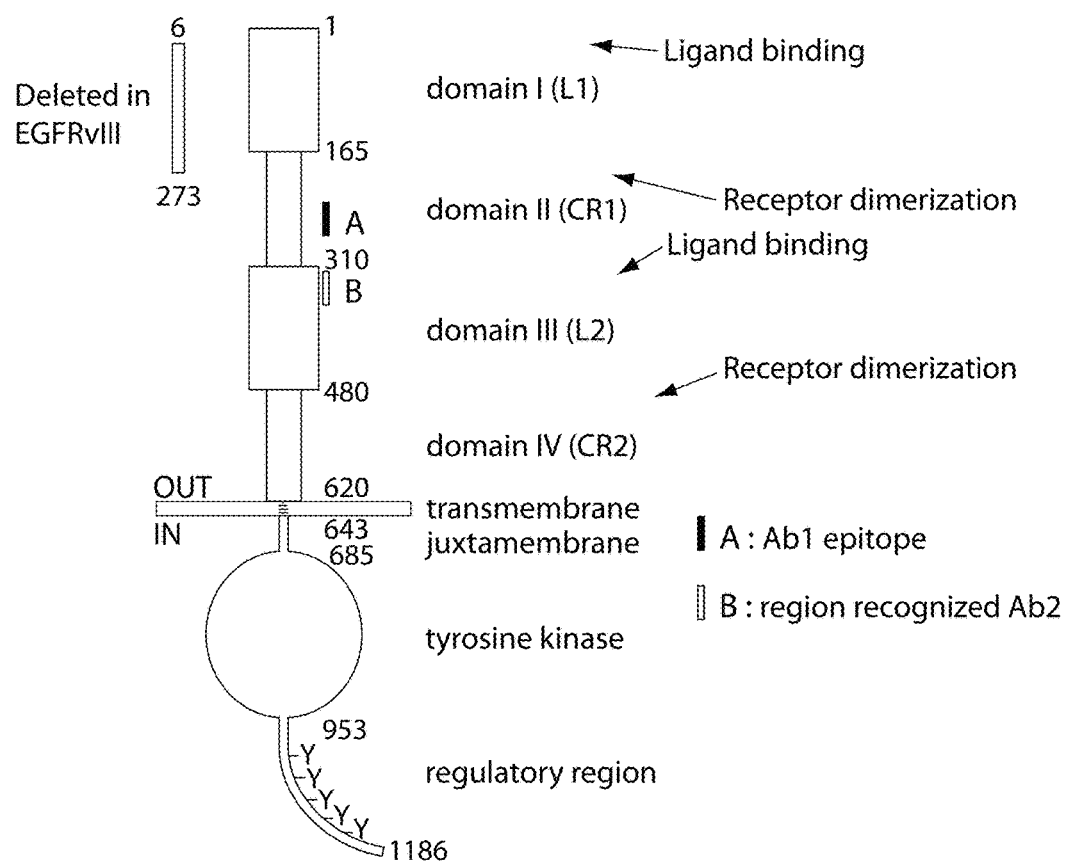
FIG. 17 shows a schematic of EGFR and the regions bound by Ab1 and Ab2.

The overall structure of EGFR is described in FIG. 17. The ECD of EGFR has four domains (Cochran et al. (2004) *J. Immunol. Methods,* 287, 147-158). Domains I and III have been suggested to contribute to the formation of high affinity binding sites for ligands. Domains II and IV are cysteine rich, laminin-like regions that stabilize protein folding and contain a possible EGFR dimerization interface.

EGFR variants may result from gene rearrangement accompanied by EGFR gene amplification. EGFRvIII is the most commonly occurring variant of the EGFR in human cancers (Kuan et al. Endocr Relat Cancer. 8(2):83-96 (2001)). During the process of gene amplification, a 267 amino acid deletion occurs in the extracellular domain of EGFR with a glycine residue inserted at the fusion junction. Thus, EGFRvIII lacks amino acids 6-273 of the extracellular domain of wild type EGFR and includes a glycine residue insertion at the junction. The EGFRvIII variant of EGFR contains a deletion of 267 amino acid residues in the extracellular domain where a glycine is inserted at the deletion junction. The EGFRvIII amino acid sequence is shown below as SEQ ID NO: 33 (the ECD is highlighted in bold and corresponds to SEQ ID NO: 46 the signal sequence is underlined).

```
                                      (SEQ ID NO: 33)
mrpsgtagaallallaalcpasraleekkgnyvvtdhgscvracgadsye
meedgvrkckkcegperkvcngigigefkdslsinatnikhfknctsisg
dlhilpvafrgdsfthtppldpqeldilktvkeitgflliqawpenrtdl
hafenleiirgrtkqhgqfslavvslnitslglrslkeisdgdviisgnk
nlcyantinwkklfgtsgqktkiisnrgensckatgqvchalcspegcwg
peprdcvscrnvsrgrecvdkcnllegeprefvenseciqchpeclpqam
nitctgrgpdnciqcahyidgphcvktcpagvmgenntlvwkyadaghvc
hlchpnctygctgpglegcptngpkipsiatgmvgallllvvalgiglf
mrrrhivrkrtlrrllqerelvepltpsgeapnqallrilketefkkikv
lgsgafgtvykglwipegekvkipvaikelreatspkankeildeayvma
svdnphvcrllgicltstvqlitqlmpfgclldyvrehkdnigsqyllnw
cvqiakgmnyledrrlvhrdlaarnvlvktpqhvkitdfglakllgaeek
eyhaeggkvpikwmalesilhriythqsdvwsygvtvwelmtfgskpydg
ipaseissilekgerlpqppictidvymimvkcwmidadsrpkfreliie
fskmardpqrylviqgdermhlpsptdsnfyralmdeedmddvvdadeyl
ipqqgffsspstsrtpllsslsatsnnstvacidrnglqscpikedsflq
```

-continued

```
ryssdptgaltedsiddtflpvpeyinqsvpkrpagsvgnpvyhnqplnp apsrdphyqdphstavgnpeylntvqptcvnstfdspahwaqkgshqisl dnpdyqqdffpkeakpngifkgstaenaeylrvapqssefiga
```

EGFRvIII contributes to tumor progression through constitutive signaling in a ligand independent manner. EGFRvIII is not known to be expressed in normal tissues (Wikstrand et al. Cancer Research 55(14): 3140-3148 (1995); Olapade-Olaopa et al. Br J Cancer. 82(1):186-94 (2000)), but shows significant expression in tumor cells, including breast cancers, gliomas, NSCL cancers, ovarian cancers, and prostate cancers (Wikstrand et al. Cancer Research 55(14): 3140-3148 (1995); Ge et al. Int J Cancer. 98(3):357-61 (2002); Wikstrand et al. Cancer Research 55(14): 3140-3148 (1995); Moscatello et al. Cancer Res. 55(23):5536-9 (1995); Garcia de Palazzo et al. Cancer Res. 53(14):3217-20 (1993); Moscatello et al. Cancer Res. 55(23):5536-9 (1995); and Olapade-Olaopa et al. 2(1):186-94 (2000)).

"Biological activity of EGFR" as used herein, refers to all inherent biological properties of the EGFR, including, but not limited to, binding to epidermal growth factor (EGF), binding to tumor growth factor α (TGFα), homodimerization, activation of JAK2 kinase activity, activation of MAPK kinase activity, and activation of transmembrane receptor protein tyrosine kinase activity.

The terms "specific binding" or "specifically binding", as used herein, in reference to the interaction of an antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

The phrase "specifically binds to hEGFR" or "specific binding to hEGFR", as used herein, refers to the ability of an anti-EGFR antibody or ADC to interact with hEGFR with an affinity equal to or greater than that of Ab1 or an Ab1 ADC.

The term "specific binding to EGFR(1-525)" or "specifically binds to EGFR(1-525)," as used herein, refers to an antibody or an ADC that binds to EGFR(1-525) and has a dissociation constant ($K_D$) of $2.3 \times 10^{-6}$ M or less, as determined by surface plasmon resonance.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG 3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hIL-13). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion" of an antibody. In certain embodiments of the invention, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Exemplary human IgG heavy chain and light chain constant domain amino acid sequences are known in the art and represented below.

Sequence of Human IgG Heavy Chain Constant Domain and Light Chain Constant Domain

| Protein | Sequence Identifier | Sequence<br>123456789012345678901234567890123456789012 |
|---|---|---|
| Ig gamma-1 constant region | SEQ ID NO: 41 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPELLGGPSVFLFPP<br>KPKDTLMISRTPEVTCVVVDVSHEDPEVKFNW<br>YVDGVEVHNAKTKPREEQYNSTYRVVSVLTVL<br>HQDWLNGKEYKCKVSNKALPAPIEKTISKAKG<br>QPREPQVYTLPPSREEMTKNQVSLTCLVKGFY<br>PSDIAVEWESNGQPENNYKTTPPVLDSDGSFF<br>LYSKLTVDKSRWQQGNVFSCSVMHEALHNHYT<br>QKSLSLSPGK |
| Ig gamma-1 constant region mutant | SEQ ID NO: 42 | ASTKGPSVFPLAPSSKSTSGGTAALGCLVKDY<br>FPEPVTVSWNSGALTSGVHTFPAVLQSSGLYS<br>LSSVVTVPSSSLGTQTYICNVNHKPSNTKVDK<br>KVEPKSCDKTHTCPPCPAPEAAGGPSVFLFPP<br>KPKDTLMISRTPEVTCVVVDVSHEDPEVKFNW<br>YVDGVEVHNAKTKPREEQYNSTYRVVSVLTVL<br>HQDWLNGKEYKCKVSNKALPAPIEKTISKAKG<br>QPREPQVYTLPPSREEMTKNQVSLTCLVKGFY<br>PSDIAVEWESNGQPENNYKTTPPVLDSDGSFF<br>LYSKLTVDKSRWQQGNVFSCSVMHEALHNHYT<br>QKSLSLSPGK |
| Ig Kappa constant region | SEQ ID NO: 43 | RTVAAPSVFIFPPSDEQLKSGTASVVCLLNNF<br>YPREAKVQWKVDNALQSGNSQESVTEQDSKDS<br>TYSLSSTLTLSKADYEKHKVYACEVTHQGLSS<br>PVTKSFNRGEC |
| Ig Lambda constant region | SEQ ID NO:44 | QPKAAPSVTLFPPSSEELQANKATLVCLISDF<br>YPGAVTVAWKADSSPVKAGVETTTPSKQSNNK<br>YAASSYLSLTPEQWKSHRSYSCQVTHEGSTVE<br>KTVAPTECS |

Still further, an antibody or antigen binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds EGFR is substantially free of antibodies that specifically bind antigens other than EGFR). An isolated antibody that specifically binds EGFR may, however, have cross-reactivity to other antigens, such as EGFR molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')₂, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the invention includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 31, 35-40, or 50 to 85.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens. In one embodiment, the multispecific antibody is a bispecific antibody that is capable of binding to two unrelated antigens, e.g., a bispecific antibody, or antigen-binding portion thereof, that binds EGFR (e.g., EGFRvIII) and CD3.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-EGFR DVD.

The term "chimeric antigen receptor" or "CAR" refers to a recombinant protein comprising at least (1) an antigen-binding region, e.g., a variable heavy or light chain of an antibody, (2) a transmembrane domain to anchor the CAR into a T cell, and (3) one or more intracellular signaling domains.

The term "activity" includes activities such as the binding specificity/affinity of an antibody or ADC for an antigen, for example, an anti-hEGFR antibody that binds to an hEGFR antigen and/or the neutralizing potency of an antibody, for example, an anti-hEGFR antibody whose binding to hEGFR inhibits the biological activity of hEGFR, e.g., inhibition of phosphorylation of EGFR in an EGFR expressing cell line, e.g., the human lung carcinoma cell line H292, or inhibition of proliferation of EGFR expressing cell lines, e.g., human H292 lung carcinoma cells, human H1703 lung carcinoma cells, or human EBC1 lung carcinoma cells.

The term "non small-cell lung carcinoma (NSCLC) xenograft assay," as used herein, refers to an in vivo assay used to determine whether an anti-EGFR antibody or ADC, can inhibit tumor growth (e.g., further growth) and/or decrease tumor growth resulting from the transplantation of NSCLC cells into an immunodeficient mouse. An NSCLC xenograft assay includes transplantation of NSCLC cells into an immunodeficient mouse such that a tumor grows to a desired size, e.g., 200-250 mm$^3$, whereupon the antibody or ADC is administered to the mouse to determine whether the antibody or ADC can inhibit and/or decrease tumor growth. In certain embodiments, the activity of the antibody or ADC is determined according to the percent tumor growth inhibition (% TGI) relative to a control antibody, e.g., a human IgG antibody (or collection thereof) which does not specifically bind tumor cells, e.g., is directed to an antigen not associated with cancer or is obtained from a source which is noncancerous (e.g., normal human serum). In such embodiments, the antibody (or ADC) and the control antibody are administered to the mouse at the same dose, with the same frequency, and via the same route. In one embodiment, the mouse used in the NSCLC xenograft assay is a severe combined immunodeficiency (SCID) mouse and/or an athymic CD-1 nude mouse. Examples of NSCLC cells that may be used in the NSCLC xenograft assay include, but are not limited to, H292 cells (e.g., NCIH292 [H292] (ATCC® CRL1848™).

The term "epitope" refers to a region of an antigen that is bound by an antibody or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules. In a particular embodiment, the antibodies of the invention bind to an epitope defined by the amino acid sequence CGADSYEMEEDGVRKC (SEQ ID NO: 45) (which corresponds to amino acid residues 287-302 of the mature form of hEGFR).

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Jöhnsson, B., et al. (1995) *J. Mol. Recognit.* 8:125-131; and Johnnson, B., et al. (1991) *Anal. Biochem.* 198:268-277. In one embodiment, surface plasmon resonance is determined according to the methods described in Example 2

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction (e.g., AbA antibody and EGFR). $K_D$ is calculated by $k_d/k_a$.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence. An example of a competition binding FACS assay is provided in Example 3 where competition FACS assay is described using U87MG cells (which express EGFRvIII).

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "anti-Epidermal Growth Factor antibody drug conjugate," "anti-EGFR antibody drug conjugate," or "anti-EGFR ADC", used interchangeably herein, refer to an ADC comprising an antibody that specifically binds to EGFR, whereby the antibody is conjugated to one or more chemical agent(s). In one embodiment, the anti-EGFR ADC is antibody AbA conjugated to an auristatin, e.g., MMAE or MMAF. Amino acid sequences corresponding to the light and heavy chains of antibody AbA are provided in SEQ ID NO: 13 and SEQ ID NO: 15, respectively.

The term "auristatin", as used herein, refers to a family of antimitotic agents. Auristatin derivatives are also included within the definition of the term "auristatin". Examples of auristatins include, but are not limited to, auristatin E (AE), monomethylauristatin E (MMAE), monomethylauristatin F (MMAF), and synthetic analogs of dolastatin. In one embodiment, an anti-EGFR antibody described herein is conjugated to an auristatin to form an anti-EGFR ADC.

As used herein, the term "AbA-vcMMAE" is used to refer to an ADC comprising the antibody AbA coupled to monomethylauristatin E (MMAE) via a maleimidocaproyl valine citrulline p-aminobenzyloxycarbamyl (PABA) linker. AbA-vcMMAE is described in FIG. 11.

As used herein, the term "mcMMAF" is used to refer to a linker/drug combination of maleimidocaproyl-monomethylauristatin F (MMAF).

The term "drug-to-antibody ratio" or "DAR" refers to the number of drugs, e.g., auristatin, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "undesired ADC species", as used herein, refers to any drug loaded species which is to be separated from an ADC species having a different drug load. In one embodiment, the term undesired ADC species may refer to drug loaded species of 6 or more, i.e., ADCs with a DAR of 6 or more, including DAR6, DAR7, DAR8, and DAR greater than 8 (i.e., drug loaded species of 6, 7, 8, or greater than 8). In a separate embodiment, the term undesired ADC species may refer to drug loaded species of 8 or more, i.e., ADCs with a DAR of 8 or more, including DAR8, and DAR greater than 8 (i.e., drug loaded species of 8, or greater than 8).

The term "ADC mixture", as used herein, refers to a composition containing a heterogeneous DAR distribution of ADCs. In one embodiment, an ADC mixture contains ADCs having a distribution of DARs of 1 to 8, e.g., 2, 4, 6, and 8 (i.e., drug loaded species of 2, 4, 6, and 8). Notably, degradation products may result such that DARs of 1, 3, 5, and 7 may also be included in the mixture. Further, ADCs within the mixture may also have DARs greater than 8. The ADC mixture results from interchain disulfide reduction followed by conjugation. In one embodiment, the ADC mixture comprises both ADCs with a DAR of 4 or less (i.e., a drug loaded species of 4 or less) and ADCs with a DAR of 6 or more (i.e., a drug loaded species of 6 or more).

The term "cancer" is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include glioblastoma, non-small cell lung cancer, lung cancer, colon cancer, colorectal cancer, head and neck cancer, breast cancer (e.g., triple negative breast cancer), pancreatic cancer, squamous cell tumors, squamous cell carcinoma (e.g., squamous cell lung cancer or squamous cell head and neck cancer), anal cancer, skin cancer, and vulvar cancer. In one embodiment, the antibodies or ADCs of the invention are administered to a patient having a tumor(s) containing amplifications of the EGFR gene, whereby the tumor expresses the truncated version of the EGFR, EGFRvIII. In one embodiment, the antibodies or ADCs of the invention are administered to a patient having a solid tumor which is likely to over-express EGFR. In one embodiment, the antibodies or ADCs of the invention are administered to a patient having squamous cell Non-Small Cell Lung Cancer (NSCLC). In one embodiment, the antibodies or ADCs of the invention are administered to a patient having solid tumors, including advanced solid tumors.

The term "EGFR expressing tumor," as used herein, refers to a tumor which expresses EGFR protein. In one embodiment, EGFR expression in a tumor is determined using immunohistochemical staining of tumor cell membranes, where any immunohistochemical staining above background level in a tumor sample indicates that the tumor is an EGFR expressing tumor. Methods for detecting expression of EGFR in a tumor are known in the art, e.g., the EGFR pharmDx™ Kit (Dako). In contrast, an "EGFR negative tumor" is defined as a tumor having an absence of EGFR membrane staining above background in a tumor sample as determined by immunohistochemical techniques.

The term "EGFRvIII positive tumor," as used herein, refers to a tumor which expresses EGFRvIII protein. In one embodiment, EGFRvIII expression in a tumor is determined using immunohistochemical staining of tumor cell membranes, where any immunohistochemical staining above background level in a tumor sample indicates that the tumor is an EGFRvIII expressing tumor. Methods for detecting expression of EGFR in a tumor are known in the art, and include immunohistochemical assays. In contrast, an "EGFRvIII negative tumor" is defined as a tumor having an absence of EGFRvIII membrane staining above background in a tumor sample as determined by immunohistochemical techniques.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 50%, 60%, 70%, 80%, 90% or more in comparison to a normal cell or comparison cell. In certain embodiments, the anti-EGFR antibodies or ADCs of the invention are used to treat solid tumors likely to overexpress EGFR.

The term "administering" as used herein is meant to refer to the delivery of a substance (e.g., an anti-EGFR antibody or ADC) to achieve a therapeutic objective (e.g., the treatment of an EGFR-associated disorder). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-EGFR antibody or ADC and an additional therapeutic agent. The additional therapeutic agent may be administered concomitant with, prior to, or following the administration of the anti-EGFR antibody or ADC.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-EGFR Antibodies

One aspect of the invention provides anti-EGFR antibodies, or antigen binding portions thereof, having improved characteristics, e.g., increased binding affinity for EGFR, over Ab1 and other antibodies known in the art. Another aspect of the invention features antibody drug conjugates (ADCs) comprising an anti-EGFR antibody described herein and at least one drug(s), such as, but not limited to, an auristatin. The antibodies or ADCs of the invention have characteristics including, but not limited to, binding to tumor cells expressing EGFRvIII, binding to wild type EGFR on tumor cells expressing EGFR, recognizing the epitope CGADSYEMEEDGVRKC (SEQ ID NO: 45) on EGFR, binding to EGFR on normal human epithelial keratinocytes, and decreasing or inhibiting xenograft tumor growth in a mouse model.

Ab1 (Antibody 1) is a humanized anti-EGFR antibody. The light and heavy chain sequences of Ab1 are described in SEQ ID NO: 13 and SEQ ID NO: 14, respectively (see also US Patent Application Publication No. 20120183471, incorporated by reference herein). The light chain variable region of Ab1 is described in SEQ ID NO: 5, and comprises a CDR1 amino acid sequence set forth in SEQ ID NO: 6, a CDR2 amino acid sequence set forth in SEQ ID NO: 7, and a CDR3 amino acid sequence set forth in SEQ ID NO: 8. The heavy chain variable region of Ab1 is described in SEQ ID NO: 1, and comprises a CDR1 amino acid sequence set forth in SEQ ID NO: 2, a CDR2 amino acid sequence set forth in SEQ ID NO: 3, and a CDR3 amino acid sequence set forth in SEQ ID NO: 4.

Generally, the Ab1 variant antibodies of the invention retain the epitope specificity of parental antibody Ab1. Thus, in one embodiment, the anti-EGFR antibodies of the invention are capable of binding an epitope in EGFR defined by SEQ ID NO: 45 and/or are able to compete with Ab1 for binding to EGFR. In various embodiments, the binding may be assayed according to the protocol set forth in Example 3 below. In a preferred embodiment of the invention, the anti-EGFR antibodies compete with Ab1 and have an improved binding affinity, e.g., dissociation constant ($K_d$) of between about $1 \times 10^{-6}$ M and about $1 \times 10^{-10}$ M, as determined by surface plasmon resonance, to 1-525 of EGFR (SEQ ID NO: 47).

In one embodiment, the invention features anti-EGFR antibodies which are variants of Ab1 and have improved characteristics, e.g., improved binding affinity and the ability to inhibit NSCLC tumor cell proliferation in vivo, as described in the Examples below. Collectively these novel antibodies are referred to herein as "Ab1 variant antibodies." Generally, the Ab1 variant antibodies retain the same epitope specificity as Ab1. Thus, in one embodiment, anti-EGFR antibodies, or antigen binding portions thereof, of the invention bind to an epitope within the amino acid sequence set forth in SEQ ID NO: 45 and compete with an anti-EGFR antibody comprising a heavy chain variable domain comprising the amino acid sequence set forth in SEQ ID NO: 1 and a light chain variable domain comprising the amino acid sequence set forth in SEQ ID NO: 5 for binding to EGFRvIII in a competitive binding assay. In contrast to Ab1, the anti-EGFR antibodies of the invention are able to inhibit or decrease tumor growth in vivo in an H292 human non-small cell lung carcinoma (NSCLC) xenograft assay in a nude mouse and/or bind to wild type EGFR on normal human epithelial keratinocytes. In various embodiments, anti-EGFR antibodies, or antigen binding fragments thereof, of the invention are capable of modulating a biological function of EGFR. In other embodiments of the foregoing aspects, the anti-EGFR antibody, or antigen binding fragment thereof, binds EGFRvIII, binds EGFR on cells overexpressing EGFR, and recognizes the epitope CGADSYEMEEDGVRKC (SEQ ID NO: 45) on EGFR. In a further embodiment, the anti-EGFR antibody, or antigen binding fragment thereof, binds EGFRvIII at an epitope which is distinct from the EGFRvIII junctional peptide. In additional embodiments of the foregoing aspects, the anti-EGFR antibody, or antigen binding fragment thereof, does not compete with cetuximab for binding of EGFR. The AbA antibody and the Ab1 variants described in the examples below have the foregoing characteristics.

Thus, the invention includes anti-EGFR antibodies, or antigen binding portions thereof, that can compete with Ab1 in a competitive binding assay but are more effective at inhibiting or decreasing tumor growth. In one embodiment, anti-EGFR antibodies, or antigen binding portions thereof, of the invention are capable of binding to an epitope within the amino acid sequence CGADSYEMEEDGVRKC (SEQ ID NO: 45) and competing with Ab1 (or an anti-EGFR antibody comprises a heavy chain variable domain comprising the amino acid sequence set forth in SEQ ID NO: 1 and a light chain variable domain comprising the amino acid sequence set forth in SEQ ID NO: 5) for binding to epidermal growth factor receptor variant III (EGFRvIII) (SEQ ID NO: 33) in a competitive binding assay.

In one embodiment, the anti-EGFR antibodies, or antigen binding portions thereof, of the invention bind to EGFR(1-525) (SEQ ID NO: 47) with a dissociation constant ($K_d$) of about $1 \times 10^{-6}$ M or less, as determined by surface plasmon resonance. Alternatively, the antibodies, or antigen binding portions thereof, bind to EGFR (1-525) (SEQ ID NO: 47) with a $K_d$ of between about $1 \times 10^{-6}$ M and about $1 \times 10^{-10}$ M, as determined by surface plasmon resonance. In a further alternative, antibodies, or antigen binding portions thereof, bind to EGFR (1-525) (SEQ ID NO: 47) with a $K_d$ of between about $1 \times 10^{-6}$ M and about $1 \times 10^{-7}$ M, as determined by surface plasmon resonance. Alternatively, antibodies, or antigen binding portions thereof, of the invention binds to EGFR (1-525) (SEQ ID NO: 47) with a $K_d$ of between about $1 \times 10^{-6}$ M and about $5 \times 10^{-10}$ M; a $K_d$ of between about $1 \times 10^{-6}$ M and about $1 \times 10^{-9}$ M; a $K_d$ of between about $1 \times 10^{-6}$ M and about $5 \times 10^{-9}$ M; a $K_d$ of between about $1 \times 10^{-6}$ M and about $1 \times 10^{-8}$ M; a $K_d$ of between about $1 \times 10^{-6}$ M and about $5 \times 10^{-8}$ M; a $K_d$ of between about $5.9 \times 10^{-7}$ M and about $1.7 \times 10^{-9}$ M; a $K_d$ of between about $5.9 \times 10^{-7}$ M and about $2.2 \times 10^{-7}$ M, as determined by surface plasmon resonance. In certain embodiments, the dissociation constant ($K_d$) of the antibodies and antigen-binding fragments of the invention is, in one embodiment, lower than the dissociation constant for Ab1 but higher than the rate of anti-EGFR antibody cetuximab.

One advantage of the anti-EGFR antibodies, and antigen-binding portions thereof, of the invention is that the antibodies are capable of binding to tumor cells expressing EGFRvIII. While EGFRvIII is associated with certain types of cancer, many anti-EGFR antibodies known in the art, e.g., cetuximab, are not effective at inhibiting or decreasing tumor growth in EGFRvIII expressing tumors. Thus, in one embodiment, the antibodies, or antigen binding portions thereof, of the invention bind to EGFRvIII (SEQ ID NO: 33) with a $K_d$ of about $8.2 \times 10^{-9}$ M or less, as determined by surface plasmon resonance. Alternatively, the antibodies, or antigen binding portions thereof, of the invention bind to EGFRvIII (SEQ ID NO: 33) with a $K_d$ of between about $8.2 \times 10^{-9}$ M and about $6.3 \times 10^{-10}$ M; a $K_d$ of between about $8.2 \times 10^{-9}$ M and about $2.0 \times 10^{-9}$ M; a $K_d$ of between about $2.3 \times 10^{-9}$ M and about $1.5 \times 10^{-10}$ M, as determined by surface plasmon resonance.

The antibodies of the invention are able, in one embodiment, to inhibit or decrease tumor growth in an in vivo xenograft mouse model. For example, the antibodies, or antigen binding portions thereof, of the invention are able to inhibit tumor growth by at least about 50% in an in vivo human non-small-cell lung carcinoma (NSCLC) xenograft assay relative to a human IgG antibody which is not specific for EGFR. In certain embodiments, the antibodies, or antigen binding portions thereof, of the invention are able to inhibit or decrease tumor growth in an in vivo human non-small-cell lung carcinoma (NSCLC) xenograft assay relative to a human IgG antibody which is not specific for EGFR by at least about 55%, at least about 60%, at least about 65%, at least about 70%, at least about 75%, or at least about 80%, when administered at the same dose and dosing periodicity. In certain embodiments, the antibodies, or antigen-binding portions thereof, of the invention are able to inhibit or decrease tumor growth in an in vivo human non-small-cell lung carcinoma (NSCLC) xenograft assay relative to a human IgG antibody which is not specific for EGFR by from about 80% to about 90%, or from about 84% to about 90%, or from about 88% to about 90%, when administered at the same dose and dosing periodicity.

The term a "xenograft assay", as used herein, refers to a human tumor xenograft assay, wherein human tumor cells are transplanted, either under the skin or into the organ type in which the tumor originated, into immunocompromised mice that do not reject human cells.

It should be noted that anti-EGFR antibodies, or antigen binding portions thereof, having combinations of the aforementioned characteristics are also considered to be embodiments of the invention. For example, antibodies of the invention may bind to EGFR(1-525) (SEQ ID NO: 47) with a dissociation constant ($K_d$) of about $1 \times 10^{-6}$ M or less, as determined by surface plasmon resonance, and bind to an epitope within the amino acid sequence CGADSYEMEEDGVRKC (SEQ ID NO: 45) and compete with Ab1 (or an anti-EGFR antibody comprising a heavy chain variable domain comprising the amino acid sequence set forth in SEQ ID NO: 1 and a light chain variable domain comprising the amino acid sequence set forth in SEQ ID NO: 5) for binding to epidermal growth factor receptor variant III (EGFRvIII) (SEQ ID NO: 33) in a competitive binding assay.

In certain embodiments, the anti-EGFR antibodies, or antigen binding portions thereof, bind to an epitope within the amino acid sequence CGADSYEMEEDGVRKC (SEQ ID NO: 45) and compete with Ab1 (or an anti-EGFR antibody comprises a heavy chain variable domain comprising the amino acid sequence set forth in SEQ ID NO: 1 and a light chain variable domain comprising the amino acid sequence set forth in SEQ ID NO: 5) for binding to epidermal growth factor receptor variant III (EGFRvIII) (SEQ ID NO: 33) in a competitive binding assay; and bind to EGFRvIII (SEQ ID NO: 33) with a $K_d$ of about $8.2 \times 10^{-9}$ M or less, as determined by surface plasmon resonance.

In certain embodiments, the anti-EGFR antibodies, or antigen binding portions thereof, bind to an epitope within the amino acid sequence CGADSYEMEEDGVRKC (SEQ ID NO: 45) and compete with Ab1 (or an anti-EGFR antibody comprises a heavy chain variable domain comprising the amino acid sequence set forth in SEQ ID NO: 1 and a light chain variable domain comprising the amino acid sequence set forth in SEQ ID NO: 5) for binding to epidermal growth factor receptor variant III (EGFRvIII) (SEQ ID NO: 33) in a competitive binding assay; and inhibit or decrease tumor growth in an in vivo xenograft mouse model. More specifically, the antibodies, or antigen binding portions thereof, of the invention are able to inhibit tumor growth by at least about 50% in an in vivo human non-small-cell lung carcinoma (NSCLC) xenograft assay relative to a human IgG antibody which is not specific for EGFR when administered at the same dose and dosing periodicity. Alternatively, the antibodies, or antigen binding portions thereof, of the invention are able to inhibit or decrease tumor growth in an in vivo human non-small-cell lung carcinoma (NSCLC) xenograft assay relative to a human IgG antibody which is not specific for EGFR by at least about 55%, at least about 60%, at least about 65%, at least about 70%, at least about 75%, or at least about 80%, when administered at the same dose and dosing periodicity. In certain embodiments, the antibodies, or antigen-binding portions thereof, of the invention are able to inhibit or decrease tumor growth in an in vivo human non-small-cell lung carcinoma (NSCLC) xenograft assay relative to a human IgG antibody which is not specific for EGFR by from about 80% to about 90%, or from about 84% to about 90%, or from about 88% to about 90%, when administered at the same dose and dosing periodicity.

Antibodies having combinations of any of the aforementioned characteristics are contemplated as aspects of the invention. ADCs of the invention, described in more detail below, may also have any of the foregoing characteristics.

In one embodiment, the invention includes an anti-hEGFR antibody, or antigen binding portion thereof, comprising an LC CDR3 domain comprising the amino acid sequence set forth in SEQ ID NO: 40, an LC CDR2 domain comprising the amino acid sequence set forth in SEQ ID NO: 39, and an LC CDR1 domain comprising the amino acid sequence set forth in SEQ ID NO: 38; and an HC CDR3 domain comprising the amino acid sequence set forth in SEQ ID NO: 37, an HC CDR2 domain comprising the amino acid sequence set forth in SEQ ID NO: 36, and an HC CDR1 domain comprising the amino acid sequence set forth in SEQ ID NO: 35.

In one embodiment, the invention includes an anti-hEGFR antibody, or antigen binding portion thereof, comprising a heavy chain variable region comprising an amino acid sequence selected from the group consisting of 50, 52, 54, 56, 58, 60, 62, 64, 66, 68, 70, 72, 74, 76, and 78; and a light chain variable region comprising an amino acid sequence selected from the group consisting of 51, 53, 55, 57, 59, 61, 63, 65, 67, 69, 71, 73, 75, 77, and 79.

In one embodiment, the invention includes an anti-hEGFR antibody, or antigen binding portion thereof, comprising an HC CDR set (CDR1, CDR2, and CDR3) selected from the group consisting of SEQ ID NOs: 10, 11, and 12; SEQ ID NOs: 16, 17, and 18; SEQ ID NOs: 10, 11, and 19; SEQ ID NOs: 20, 11, and 12; SEQ ID NOs: 21, 3, and 22; SEQ ID NOs: 16, 17, and 19; SEQ ID NOs: 2, 3, and 4; SEQ ID NOs: 10, 3, and 12; SEQ ID NOs: 80, 11, and 18; SEQ ID NOs: 80, 3, and 18; SEQ ID NOs: 20, 3, and 12; SEQ ID NOs: 80, 11, and 12; and SEQ ID NOs: 81, 11, and 22; and an LC light chain CDR set (CDR1, CDR2, and CDR3) selected from the group consisting of SEQ ID NOs: 6, 7, and 8; SEQ ID NOs: 23, 24, and 25; SEQ ID NOs: 26, 27, and 28; SEQ ID NOs: 29, 30, and 31; SEQ ID NOs: 6, 7, and 84; SEQ ID NOs: 82, 83, and 31; and SEQ ID NOs: 82, 27, and 85, wherein the antibody, or antigen binding portion thereof, does not comprise both the HC CDR set of SEQ ID NOs: 2, 3, and 4, and the LC CDR set of SEQ ID NOs: 6, 7, and 8.

Preferably, anti-EGFR antibodies of the invention, exhibit a high capacity to reduce or to neutralize EGFR activity, e.g., as assessed by any one of several in vitro and in vivo assays known in the art. For example, inhibition of phosphorylation of EGFR in an EGFR expressing cell line, e.g., the h292 cell line, can be measured. In certain embodiments, the isolated antibody, or antigen binding portion thereof, binds human EGFR, wherein the antibody, or antigen binding portion thereof, dissociates from human EGFR (EGFR 1-525) with a $K_D$ rate constant of about $5.9 \times 10^{-7}$ M or less, as determined by surface plasmon resonance. Alternatively, the antibody, or an antigen binding portion thereof, may dissociate from human EGFR (1-525) with a $K_D$ rate constant of about $4.2 \times 10^{-7}$ M, as determined by surface plasmon resonance. Alternatively, the antibody, or an antigen binding portion thereof, may dissociate from human EGFR (1-525) with a $k_{off}$ rate constant of about $K_D$ rate constant of about $2.5 \times 10^{-7}$ M, as determined by surface plasmon resonance. In certain embodiments, the anti-EGFR antibodies, or antigen binding portion thereof, of the invention have a $K_D$ rate constant of between $5.9 \times 10^{-7}$ M and $5 \times 10^{-9}$ M.

Alternatively, the antibody, or an antigen binding portion thereof, may dissociate from human EGFRvIII with a $K_D$ rate constant of about $6.1 \times 10^{-9}$ M or less, as determined by surface plasmon resonance. Alternatively, the antibody, or an antigen binding portion thereof, may dissociate from human EGFRvIII with a $K_D$ rate constant of about $3.9 \times 10^{-9}$ M or less, as determined by surface plasmon resonance. Alternatively, the antibody, or an antigen binding portion thereof, may dissociate from human EGFRvIII with a $K_D$ rate constant of about $2.3 \times 10^{-9}$ M or less, as determined by surface plasmon resonance.

In one embodiment, the invention features an anti-EGFR antibody, or antigen binding portion thereof, which is antibody AbA. AbA has improved binding affinity over Ab1 for EGFR, and also exhibits unique in vitro and in vivo characteristics relative to Ab1. AbA binds EGFR in an in vitro keratinocyte binding assay with a much affinity greater than that of Ab1. Further, AbA is able to inhibit or decrease tumor growth in a xenograft H292 cell assay. Notably, AbA has improved in vitro and in vivo characteristics which are comparable to other Ab1 variant antibodies which had higher binding affinity than that of AbA. Despite having lower binding affinity in comparison to other Ab1 variant antibodies (see for example AbP and AbQ vs. AbA in FIG. 3), AbA was comparable at inhibiting cell growth in an in vivo assay.

The term "AbA" is meant to include an IgG antibody having at least the six CDRs of AbA. The AbA antibody has the same light chain as that of Ab1, but has a heavy chain containing six amino acid sequence changes relative to parental antibody Ab1 (four amino acid changes in the variable region and two changes in the constant region of the heavy chain). The AbA antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. The heavy chain variable region of AbA is defined by the amino acid sequence set forth in SEQ ID NO: 9, and a light chain variable region comprising the amino acid sequence of SEQ ID NO: 5. The full length heavy chain of antibody AbA is set forth in the amino acid sequence described in SEQ ID NO: 15, while the full length light chain of antibody AbA is set forth in the amino acid sequence described in SEQ ID NO: 13 (see FIG. 2). The nucleic acid sequence of the heavy chain of AbA is provided below:

(SEQ ID NO: 86)
gaggtgcaactccaagagagcgggcccggcctcgtgaagccctctcagac tctgtccctgacttgcactgtgagcgggtattccatcagcagagacttcg catggaactggatccgccagcctcccggtaagggactggagtggatgggg tacatcagctacaacggtaatacacgctatcagccctccctgaagtctcg cattaccattagtcgcgatacctccaagaaccagttctttctgaaactca acagcgtgacagccgctgacaccgccacctactactgcgtgaccgccagc -continued
```
aggggggttcccttactggggccagggcactctggtcaccgtttcttctgc gtcgaccaagggcccatcggtcttcccctggcaccctcctccaagagca cctctgggggcacagcggccctgggctgcctggtcaaggactacttcccc gaaccggtgacggtgtcgtggaactcaggcgccctgaccagcggcgtgca caccttcccggctgtcctacagtcctcaggactctactccctcagcagcg tggtgaccgtgccctccagcagcttgggcacccagacctacatctgcaac gtgaatcacaagcccagcaacaccaaggtggacaagaaagttgagcccaa atcttgtgacaaaactcacacatgcccaccgtgcccagcacctgaactcc tggggggaccgtcagtcttcctcttcccccaaaacccaaggacaccctc atgatctcccggacccctgaggtcacatgcgtggtggtggacgtgagcca cgaagaccctgaggtcaagttcaactggtacgtggacggcgtggaggtgc ataatgccaagacaaagccgcgggaggagcagtacaacagcacgtaccgt gtggtcagcgtcctcaccgtcctgcaccaggactggctgaatggcaagga gtacaagtgcaaggtctccaacaaagcctcccagccccatcgagaaaa ccatctccaaagccaaaggcagccccgagaaccacaggtgtacaccctg cccccatcccgcgaggagatgaccaagaaccaggtcagcctgacctgcct ggtcaaaggcttctatcccagcgacatcgccgtggagtgggagagcaatg ggcagccggagaacaactacaagaccacgcctcccgtgctggactccgac ggctccttcttcctctacagcaagctcaccgtggacaagagcaggtggca gcaggggaacgtcttctcatgctccgtgatgcatgaggctctgcacaacc actacacgcagaagagcctctccctgtctccgggtaaa
```

The nucleic acid sequence of the light chain of AbA is provided below:

```
                                        (SEQ ID NO: 87)
Gacatccagatgacccagtcccctccagtatgtctgtgtctgtgggcga ccgtgtgaccattacctgccactcctcccaggacatcaatagcaatatcg gttggttgcaacagaagccaggcaagtccttcaaagggctgatttaccat ggtaccaacctggacgacggggttcctagtcgtttcagcggctccgggtc cggaaccgattacactctgaccatcagcagtttgcagcctgaggactttg ctacctattattgtgtgcagtacgctcagttcccatggactttcggcggg ggcaccaaactggagatcaaacgtacggtggctgcaccatctgtcttcat cttcccgccatctgatgagcagttgaaatctggaactgcctctgttgtgt gcctgctgaataacttctatcccagagaggccaaagtacagtggaaggtg gataacgccctccaatcgggtaactcccaggagagtgtcacagagcagga cagcaaggacagcacctacagcctcagcagcaccctgacgctgagcaaag cagactacgagaaacacaaagtctacgcctgcgaagtcacccatcagggc ctgagctcgcccgtcacaaagagcttcaacaggggagagtgt
```

In one embodiment, the invention features an anti-EGFR antibody, or antigen binding portion thereof, which is the antibody AbB. The AbB antibody comprises a heavy chain variable region comprising a CDR3 domain comprising the amino acid sequence of SEQ ID NO: 19, a CDR2 domain comprising the amino acid sequence of SEQ ID NO: 17, and a CDR1 domain comprising the amino acid sequence of SEQ ID NO: 16, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, the invention provides an antibody having a heavy chain variable region comprising the amino acid sequence of SEQ ID NO: 64 and a light chain variable region comprising the amino acid sequence of SEQ ID NO: 65.

In one embodiment, the invention features an anti-EGFR antibody, or antigen binding portion thereof, which is the antibody AbC. The AbC antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 84, a CDR2 domain comprising the amino acid sequence of SEQ ID NO: 7, and a CDR1 domain comprising the amino acid sequence of SEQ ID NO: 6. In further embodiments, the invention provides an antibody having a heavy chain variable region comprising the amino acid sequence of SEQ ID NO: 66 and a light chain variable region comprising the amino acid sequence of SEQ ID NO: 67.

In one embodiment, the invention features an anti-EGFR antibody, or antigen binding portion thereof, which is the antibody AbD. The AbD antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 31, a CDR2 domain comprising the amino acid sequence of SEQ ID NO: 83, and a CDR1 domain comprising the amino acid sequence of SEQ ID NO: 82. In further embodiments, the invention provides an antibody having a heavy chain variable region comprising the amino acid sequence of SEQ ID NO: 68 and a light chain variable region comprising the amino acid sequence of SEQ ID NO: 69.

In one embodiment, the invention features an anti-EGFR antibody, or antigen binding portion thereof, which is the antibody AbE. The AbE antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 85, a CDR2 domain comprising the amino acid sequence of SEQ ID NO: 27, and a CDR1 domain comprising the amino acid sequence of SEQ ID NO: 82. In further embodiments, the invention provides an antibody having a heavy chain variable region comprising the amino acid sequence of SEQ ID NO: 50 and a light chain variable region comprising the amino acid sequence of SEQ ID NO: 51.

In one embodiment, the invention features an anti-EGFR antibody, or antigen binding portion thereof, which is the antibody AbF. The AbF antibody comprises a heavy chain variable region comprising a CDR3 domain comprising the amino acid sequence of SEQ ID NO: 12, a CDR2 domain comprising the amino acid sequence of SEQ ID NO: 3, and a CDR1 domain comprising the amino acid sequence of SEQ ID NO: 10, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, the invention provides an antibody having a heavy chain variable region comprising the amino acid sequence of SEQ ID NO: 52 and a light chain variable region comprising the amino acid sequence of SEQ ID NO: 53.

In one embodiment, the invention features an anti-EGFR antibody, or antigen binding portion thereof, which is the antibody AbG. The AbG antibody comprises a heavy chain variable region comprising a CDR3 domain comprising the amino acid sequence of SEQ ID NO: 18, a CDR2 domain comprising the amino acid sequence of SEQ ID NO: 17, and a CDR1 domain comprising the amino acid sequence of SEQ ID NO: 16, and a light chain variable region comprising a CDR3 domain comprising the amino acid sequence of SEQ ID NO: 25, a CDR2 domain comprising the amino acid sequence of SEQ ID NO: 24, and a CDR1 domain comprising the amino acid sequence of SEQ ID NO: 23. In further embodiments, the invention provides an antibody having a heavy chain variable region comprising the amino acid sequence of SEQ ID NO: 72 and a light chain variable region comprising the amino acid sequence of SEQ ID NO: 73.

In one embodiment, the invention features an anti-EGFR antibody, or antigen binding portion thereof, which is the antibody AbH. The AbH antibody comprises a heavy chain variable region comprising a CDR3 domain comprising the amino acid sequence of SEQ ID NO: 18, a CDR2 domain comprising the amino acid sequence of SEQ ID NO: 11, and a CDR1 domain comprising the amino acid sequence of SEQ ID NO: 80, and a light chain variable region comprising a CDR3 domain comprising the amino acid sequence of SEQ ID NO: 25, a CDR2 domain comprising the amino acid sequence of SEQ ID NO: 24, and a CDR1 domain comprising the amino acid sequence of SEQ ID NO: 23. In further embodiments, the invention provides an antibody having a heavy chain variable region comprising the amino acid sequence of SEQ ID NO: 54 and a light chain variable region comprising the amino acid sequence of SEQ ID NO: 55.

In one embodiment, the invention features an anti-EGFR antibody, or antigen binding portion thereof, which is the antibody AbJ. The AbJ antibody comprises a heavy chain variable region comprising a CDR3 domain comprising the amino acid sequence of SEQ ID NO: 18, a CDR2 domain comprising the amino acid sequence of SEQ ID NO: 3, and a CDR1 domain comprising the amino acid sequence of SEQ ID NO: 80, and a light chain variable region comprising a CDR3 domain comprising the amino acid sequence of SEQ ID NO: 25, a CDR2 domain comprising the amino acid sequence of SEQ ID NO: 24, and a CDR1 domain comprising the amino acid sequence of SEQ ID NO: 23. In further embodiments, the invention provides an antibody having a heavy chain variable region comprising the amino acid sequence of SEQ ID NO: 56 and a light chain variable region comprising the amino acid sequence of SEQ ID NO: 57.

In one embodiment, the invention features an anti-EGFR antibody, or antigen binding portion thereof, which is the antibody AbK. The AbK antibody comprises a heavy chain variable region comprising a CDR3 domain comprising the amino acid sequence of SEQ ID NO: 19, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26. In further embodiments, the invention provides an antibody having a heavy chain variable region comprising the amino acid sequence of SEQ ID NO: 74 and a light chain variable region comprising the amino acid sequence of SEQ ID NO: 75.

In one embodiment, the invention features an anti-EGFR antibody, or antigen binding portion thereof, which is the antibody AbL. The AbL antibody comprises a heavy chain variable region comprising a CDR3 domain comprising the amino acid sequence of SEQ ID NO: 18, a CDR2 domain comprising the amino acid sequence of SEQ ID NO: 11, and a CDR1 domain comprising the amino acid sequence of SEQ ID NO: 80, and a light chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26. In further embodiments, the invention provides an antibody having a heavy chain variable region comprising the amino acid sequence of SEQ ID NO: 58 and a light chain variable region comprising the amino acid sequence of SEQ ID NO: 59.

In one embodiment, the invention features an anti-EGFR antibody, or antigen binding portion thereof, which is the antibody AbM. The AbM antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 20, and a light chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26. In further embodiments, the invention provides an antibody having a heavy chain variable region comprising the amino acid sequence of SEQ ID NO: 76 and a light chain variable region comprising the amino acid sequence of SEQ ID NO: 77.

In one embodiment, the invention features an anti-EGFR antibody, or antigen binding portion thereof, which is the antibody AbN. The AbN antibody comprises a heavy chain variable region comprising a CDR3 domain comprising the amino acid sequence of SEQ ID NO: 12, a CDR2 domain comprising the amino acid sequence of SEQ ID NO: 3, and a CDR1 domain comprising the amino acid sequence of SEQ ID NO: 20, and a light chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26. In further embodiments, the invention provides an antibody having a heavy chain variable region comprising the amino acid sequence of SEQ ID NO: 60 and a light chain variable region comprising the amino acid sequence of SEQ ID NO: 61.

In one embodiment, the invention features an anti-EGFR antibody, or antigen binding portion thereof, which is the antibody AbO. The AbO antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 80, and a light chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26. In further embodiments, the invention provides an antibody having a heavy chain variable region comprising the amino acid sequence of SEQ ID NO: 62 and a light chain variable region comprising the amino acid sequence of SEQ ID NO: 63.

In one embodiment, the invention features an anti-EGFR antibody, or antigen binding portion thereof, which is the antibody AbP. The AbP antibody comprises a heavy chain variable region comprising a CDR3 domain comprising the amino acid sequence of SEQ ID NO: 22, a CDR2 domain comprising the amino acid sequence of SEQ ID NO: 3, and a CDR1 domain comprising the amino acid sequence of SEQ ID NO: 21, and a light chain variable region comprising a CDR3 domain comprising the amino acid sequence of SEQ ID NO: 31, a CDR2 domain comprising the amino acid sequence of SEQ ID NO: 30, and a CDR1 domain comprising the amino acid sequence of SEQ ID NO: 29. In further embodiments, the invention provides an antibody having a heavy chain variable region comprising the amino acid sequence of SEQ ID NO: 78 and a light chain variable region comprising the amino acid sequence of SEQ ID NO: 79.

In one embodiment, the invention features an anti-EGFR antibody, or antigen binding portion thereof, which is the antibody AbQ. The AbQ antibody comprises a heavy chain variable region comprising a CDR3 domain comprising the amino acid sequence of SEQ ID NO: 22, a CDR2 domain comprising the amino acid sequence of SEQ ID NO: 11, and a CDR1 domain comprising the amino acid sequence of SEQ ID NO: 81, and a light chain variable region comprising a CDR3 domain comprising the amino acid sequence of SEQ ID NO: 31, a CDR2 domain comprising the amino acid sequence of SEQ ID NO: 30, and a CDR1 domain comprising the amino acid sequence of SEQ ID NO: 29. In further embodiments, the invention provides an antibody having a heavy chain variable region comprising the amino acid sequence of SEQ ID NO: 70 and a light chain variable region comprising the amino acid sequence of SEQ ID NO: 71.

As described in Table 1 in the examples set forth below, the Ab1 variant antibody sequences provide amino acid consensus sequences that represent CDR domains resulting in improved binding to the Ab1 EGFR epitope. Thus, in one embodiment, the invention features an anti-EGFR antibody, or antigen binding portion thereof, comprising a light chain variable region comprising a CDR3 domain comprising the amino acid sequence set forth as SEQ ID NO: 40, a CDR2 domain comprising the amino acid sequence set forth as SEQ ID NO: 39, and a CDR1 domain comprising the amino acid sequence set forth as SEQ ID NO: 38; and a heavy chain variable region comprising a CDR3 domain comprising the amino acid sequence set forth as SEQ ID NO: 37, a CDR2 domain comprising the amino acid sequence set forth as SEQ ID NO: 36, and a CDR1 domain comprising the amino acid sequence set forth as SEQ ID NO: 35.

In one embodiment, the anti-Epidermal Growth Factor Receptor (anti-EGFR) antibody, or antigen binding portion thereof, comprises a heavy chain variable region comprising an amino acid sequence selected from the group consisting of 50, 52, 53, 56, 58, 60, 62, 64, 66, and 68; and a light chain variable region comprising an amino acid sequence selected from the group consisting of 51, 53, 55, 57, 59, 61, 63, 65, 67, and 69.

In a further embodiment, the anti-EGFR antibody, or antigen binding portion thereof, of the invention comprises a heavy chain variable region comprising a CDR3 domain comprising an amino acid sequence as set forth in SEQ ID NO: 12, 18, 19, and 22; a CDR2 domain comprising an amino acid sequence as set forth in SEQ ID NO: 11 or 17; and a CDR1 domain comprising an amino acid sequence as set forth in SEQ ID NO: 10, 16, 20, and 21; and a light chain variable region comprising a CDR3 domain comprising an amino acid sequence as set forth in SEQ ID NO: 8, 25, 28, and 31; a CDR2 domain comprising an amino acid sequence as set forth in SEQ ID NO: 7, 24, 27, and 30; and a CDR1 domain comprising an amino acid sequence as set forth in SEQ ID NO: 6, 23, 26, and 29.

Phosphorylation and proliferation assays demonstrated that the antibodies described herein, inhibited EGFR mediated phosphorylation and tumor cell growth. For example, as set forth in Example 6, the EGFR antibodies (as tested) of the invention were shown to inhibit tumor cell growth in vivo.

The foregoing anti-EGFR antibody CDR sequences establish a novel family of EGFR binding proteins, isolated in accordance with this invention, and comprising polypeptides that include the CDR sequences listed in Tables 1 to 3 below.

To generate and to select CDRs having preferred EGFR binding and/or neutralizing activity with respect to hEGFR, standard methods known in the art for generating antibodies, or antigen binding portions thereof, and assessing the EGFR binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-EGFR antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-EGFR antibody binding portion is a Fab, a Fab', a F(ab')2, a Fv, a disulfide linked Fv, an scFv, a single domain antibody, or a diabody.

In certain embodiments, the anti-EGFR antibody, or antigen binding portion thereof, is a multispecific antibody, e.g. a bispecific antibody.

In certain embodiments, the anti-EGFR antibody, or antigen binding portion thereof, comprises a heavy chain constant region comprising the amino acid sequence set forth in SEQ ID NO: 41 and/or a light chain constant region comprising the amino acid sequence set forth in SEQ ID NO: 43.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment of the invention includes a recombinant chimeric antigen receptor (CAR) comprising the binding regions of the antibodies described herein, e.g., the heavy and/or light chain CDRs of AbA. A recombinant CAR, as described herein, may be used to redirect T cell specificity to an antigen in a human leukocyte antigen (HLA)-independent fashion. Thus, CARS of the invention may be used in immunotherapy to help engineer a human subject's own immune cells to recognize and attack the subject's tumor (see, e.g., U.S. Pat. Nos. 6,410,319; 8,389,282; 8,822,647; 8,906,682; 8,911,993; 8,916,381; 8,975,071; and U.S. Patent Appln. Publ. No. US20140322275, each of which is incorporated by reference herein with respect to CAR technology). This type of immunotherapy is called adoptive cell transfer (ACT), and may be used to treat cancer in a subject in need thereof.

An anti-EGFR CAR of the invention preferably contains a extracellular antigen-binding domain specific for EGFR (e.g. EGFRvIII), a transmembrane domain which is used to anchor the CAR into a T cell, and one or more intracellular signaling domains. In one embodiment of the invention, the CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment of the invention, the CAR comprises a costimulatory domain, e.g., a costimulatory domain comprising a functional signaling domain of a protein selected from the group consisting of OX40, CD2, CD27, CD28, CD5, ICAM-1, LFA-1 (CD11a/CD18), ICOS (CD278), and 4-1BB (CD137). In certain embodiments of the invention, the CAR comprises an scFv comprising the CDR or variable regions described herein e.g., CDRs or variable regions from the AbA antibody, a transmembrane domain, a costimulatory domain (e.g., a functional signaling domain from CD28 or 4-1BB), and a signaling domain comprising a functional signaling domain from CD3 (e.g., CD3-zeta).

In certain embodiments, the invention includes a T cell comprising a CAR (also referred to as a CAR T cell) comprising antigen binding regions, e.g. CDRs, of the antibodies described herein or an scFv described herein.

In certain embodiments of the invention, the CAR comprises a variable heavy light chain comprising a CDR3 domain comprising the amino acid sequence set forth in SEQ ID NO: 40, a CDR2 domain comprising the amino acid sequence set forth in SEQ ID NO: 39, and a CDR1 domain comprising the amino acid sequence set forth in SEQ ID NO: 38; and a heavy chain variable region comprising a CDR3 domain comprising the amino acid sequence set forth in SEQ ID NO: 37, a CDR2 domain comprising the amino acid sequence set forth in SEQ ID NO: 36, and a CDR1 domain comprising the amino acid sequence set forth in SEQ ID NO: 35.

In certain embodiments of the invention, the CAR comprises a variable heavy light chain comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 10; and a heavy chain variable region comprising a CDR3 domain comprising the amino acid sequence set forth in SEQ ID NO: 8, a CDR2 domain comprising the amino acid sequence set forth in SEQ ID NO: 7, and a CDR1 domain comprising the amino acid sequence set forth in SEQ ID NO: 6.

One embodiment of the invention includes a labeled anti-EGFR antibody, or antibody portion thereof, where the antibody is derivatized or linked to one or more functional molecule(s) (e.g., another peptide or protein). For example, a labeled antibody can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody of the invention is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying EGFR positive tumors. In a certain embodiment, anti-EGFR antibodies (or ADCs) described herein are labeled with via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the invention provides a glycosylated binding protein wherein the anti-EGFR antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the invention is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the invention.

In still another embodiment, the glycosylation of the anti-EGFR antibody or antigen binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-EGFR antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell in a suitable culture medium until a recombinant antibody is synthesized. Recombinant antibodies of the invention may be produced using nucleic acid molecules corresponding to the amino acid sequences disclosed herein. In one embodiment, the nucleic acid molecules set forth in SEQ ID NOs: 86 and/or 87 are used in the production of a recombinant antibody. The method can further comprise isolating the recombinant antibody from the culture medium.

III. Anti-EGFR Antibody Drug Conjugates (ADCs)

Anti-EGFR antibodies described herein may be conjugated to a drug moiety to form an anti-EGFR Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues, such as a tumor-associated antigen, e.g., EGFR expressing tumors. Thus, in certain embodiments, the invention provides anti-EGFR ADCs for therapeutic use, e.g., treatment of cancer.

Anti-EGFR ADCs of the invention comprise an anti-EGFR antibody, i.e., an antibody that specifically binds to EGFR, linked to one or more drug moieties. The specificity of the ADC is defined by the specificity of the antibody, i.e., anti-EGFR. In one embodiment, an anti-EGFR antibody is linked to one or more cytotoxic drug(s) which is delivered internally to a transformed cancer cell expressing EGFR.

Examples of drugs that may be used in the anti-EGFR ADC of the invention are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

$$Ab-(L-D)_n \qquad (I)$$

wherein Ab is the antibody, e.g., anti-EGFR antibody AbA, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing EGFR; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I. In one embodiment, the ADC has a formula of $Ab-(L-D)_n$, wherein Ab is an anti-EGFR antibody, e.g. AbA, L is a linker, e.g., valine citrulline (vc), D is a drug, e.g., an auristatin such as MMAF or MMAE, and n is 2 to 4 (equivalent to a DAR of 2-4). Additional details regarding drugs (D of Formula I) and linkers (L of Formula I) that may be used in the ADCs of the invention, as well as alternative ADC structures, are described below.

A. Anti-EGFR ADCs: Exemplary Drugs for Conjugation

Anti-EGFR antibodies may be used in ADCs to target one or more drug(s) to a cell of interest, e.g., a cancer cell expressing EGFR. The anti-EGFR ADCs of the invention provide a targeted therapy that may, for example, reduce the side effects often seen with anti-cancer therapies, as the one or more drug(s) is delivered to a specific cell.

Auristatins

Anti-EGFR antibodies of the invention, e.g., the AbA antibody, may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

In one embodiment, anti-EGFR antibodies of the invention, e.g., AbA, are conjugated to at least one MMAE (mono-methyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-EGFR antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism.

In one embodiment, an anti-EGFR antibody described herein, e.g., AbA, is conjugated to at least one MMAF (monomethylauristatin F). Monomethyl auristatin F (MMAF) inhibits cell division by blocking the polymerization of tubulin. It has a charged C-terminal phenylalanine residue that attenuates its cytotoxic activity compared to its uncharged counterpart MMAE. Because of its super toxicity, it cannot be used as a drug itself, but can be linked to a monoclonal antibody (mAb) that directs it to the cancer cells. In one embodiment, the linker to the anti-EGFR antibody is stable in extracellular fluid, but is cleaved by cathepsin once the conjugate has entered a tumor cell, thus activating the anti-mitotic mechanism.

The structures of MMAF and MMAE are provided below.

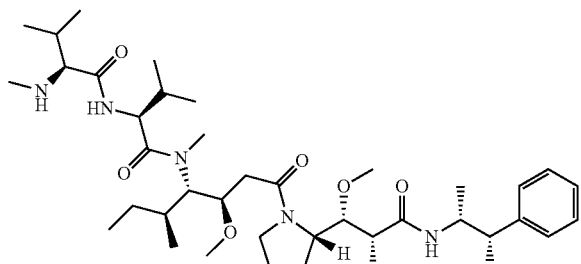

Monomethyl Auristatin E (MMAE)

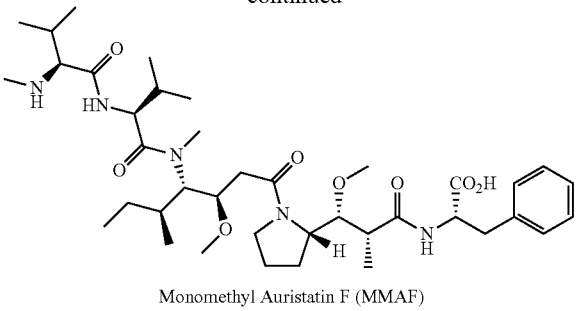

Monomethyl Auristatin F (MMAF)

Figure 11:
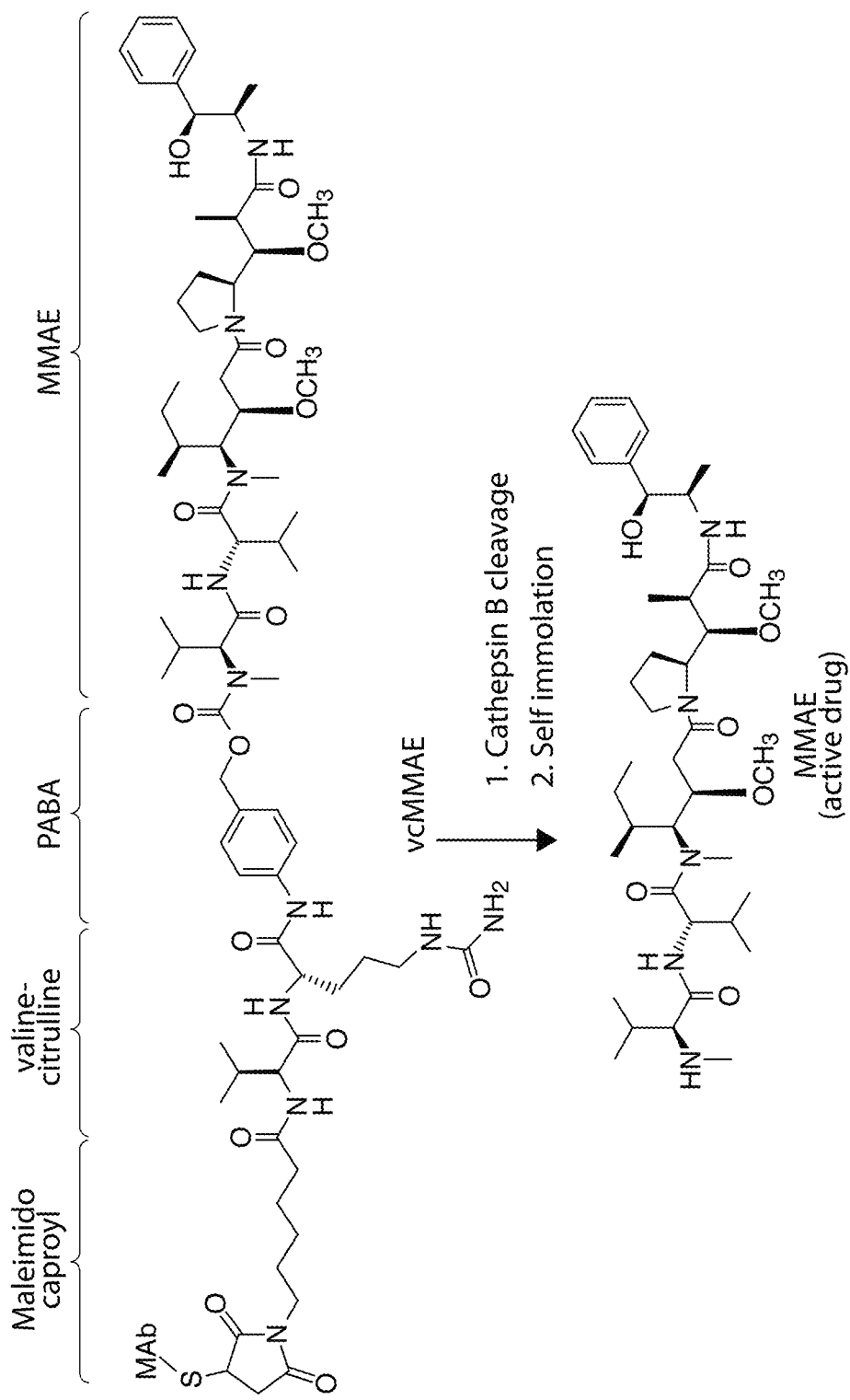
FIG. 11 provides the structure of the AbA-malemido-caproyl-vc-PABA-MMAE ADC (referred to herein as "AbA-vcMMAE").

An example of AbA-vcMMAE is also provided in FIG. 11. Notably, FIG. 11 describes a situation where the antibody (e.g., AbA) is coupled to a single drug and, therefore, has a DAR of 1. In certain embodiments, the ADC will have a DAR of 2 to 8, or, alternatively, 2 to 4.

Other Drugs for Conjugation

Examples of drugs that may be used in ADCs, i.e., drugs that may be conjugated to the anti-EGFR antibodies of the invention, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-EGFR antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by affecting microtubule polymerization or microtubule depolymerization. Thus, in one embodiment, an anti-EGFR antibody of the invention is conjugated to one or more mitotic inhibitor(s) that disrupts microtubule formation by inhibiting tubulin polymerization. In one embodiment, the mitotic inhibitor used in the ADCs of the invention is Ixempra (ixabepilone). Examples of mitotic inhibitors that may be used in the anti-EGFR ADCs of the invention are provided below. Included in the genus of mitotic inhibitors are auristatins, described above.

a. Dolastatins

The anti-EGFR antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-EGFR ADC of the invention comprises an anti-EGFR antibody, as described herein, and at least one dolastatin. Auristatins, described above, are synthetic derivatives of dolastatin 10.

b. Maytansinoids

The anti-EGFR antibodies of the invention may be conjugated to at least one maytansinoid to form an ADC. Maytansinoids are potent antitumor agents that were originally isolated from members of the higher plant families Celastraceae, Rhamnaceae and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in section III.B. The structure of an exemplary maytansinoid, mertansine (DM1), is provided below.

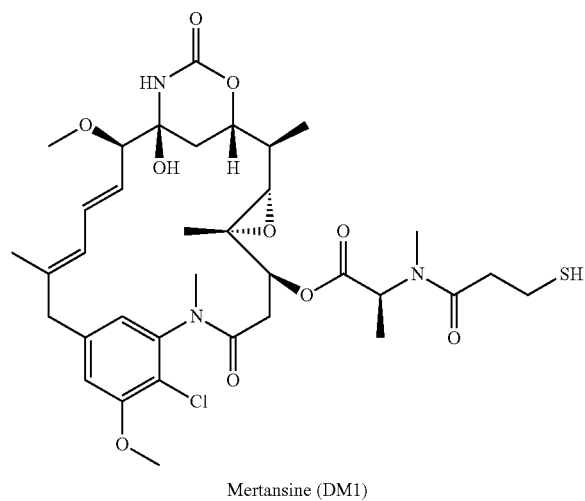

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) Cancer Res 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine) and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-EGFR antibody is conjugated to at least one DM1. In one embodiment, an anti-EGFR antibody is conjugated to at least one DM2. In one embodiment, an anti-EGFR antibody is conjugated to at least one DM3. In one embodiment, an anti-EGFR antibody is conjugated to at least one DM4.

d. Plant Alkaloids

The anti-EGFR antibodies of the invention may be conjugated to at least one plant alkaloid, e.g., a taxane or vinca alkaloid. Plant alkaloids are chemotherapy treatments derived made from certain types of plants. The vinca alkaloids are made from the periwinkle plant (catharanthus rosea), whereas the taxanes are made from the bark of the Pacific Yew tree (taxus). Both the vinca alkaloids and taxanes are also known as antimicrotubule agents, and are described in more detail below.

Taxanes

Anti-EGFR antibodies described herein may be conjugated to at least one taxane. The term "taxane" as used herein refers to the class of antineoplastic agents having a mechanism of microtubule action and having a structure that includes the taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869, each of which is incorporated by reference herein. Taxane compounds have also previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference. Further examples of taxanes include, but are not limited to, docetaxel (Taxotere; Sanofi Aventis), paclitaxel (Abraxane or Taxol; Abraxis Oncology), and nanoparticle paclitaxel (ABI-007/Abraxene; Abraxis Bioscience).

In one embodiment, the anti-EGFR antibody of the invention is conjugated to at least one docetaxel. In one embodiment, the anti-EGFR antibody of the invention is conjugated to at least one paclitaxel.

Vinca Alkaloids

In one embodiment, the anti-EGFR antibody is conjugated to at least one vinca alkaloid. Vinca alkaloids are a class of cell-cycle-specific drugs that work by inhibiting the ability of cancer cells to divide by acting upon tubulin and preventing the formation of microtubules. Examples of vinca alkaloids that may be used in the ADCs of the invention include, but are not limited to, vindesine sulfate, vincristine, vinblastine and vinorelbine.

2. Antitumor Antibiotics

Anti-EGFR antibodies of the invention may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-EGFR ADCs of the invention include, but are not limited to, actinomycines (e.g., pyrrolo[2,1-c][1,4]benzodiazepines), anthracyclines, calicheamicins, and duocarmycins, described in more detail below.

a. Actinomycines

The anti-EGFR antibodies of the invention may be conjugated to at least one actinomycine. Actinomycines are a subclass of antitumor antibiotics isolated from bacteria of the genus *Streptomyces*. Representative examples actinomycines include, but are not limited to, actinomycin D (Cosmegen [also known as actinomycin, dactinomycin, actinomycin IV, actinomycin C1], Lundbeck, Inc.), anthramycin, chicamycin A, DC-81, mazethramycin, neothramycin A, neothramycin B, porothramycin, prothracarcin B, SG2285, sibanomicin, sibiromycin and tomaymycin. In one embodiment, the anti-EGFR antibody of the invention is conjugated to at least one pyrrolobenzodiazepine (PBD). Examples of PBDs include, but are not limited to, anthramycin, chicamycin A, DC-81, mazethramycin, neothramycin A, neothramycin B, porothramycin, prothracarcin B, SG2000 (SJG-136), SG2202 (ZC-207), SG2285 (ZC-423), sibanomicin, sibiromycin and tomaymycin. Thus, in one embodiment, anti-EGFR antibodies of the invention are conjugated to at least one actinomycine, e.g., actinomycin D, or at least one PBD, e.g., a pyrrolobenzodiazepine (PBD) dimer.

The structures of PBDs can be found, for example, in U.S. Patent Application Pub. Nos. 2013/0028917 and 2013/0028919, and in WO 2011/130598 A1, each of which are incorporated herein by reference in their entirety. The generic structure of a PBD is provided below.

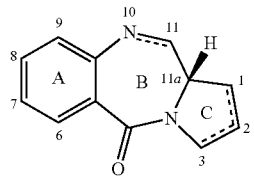

PBDs differ in the number, type and position of substituents, in both their aromatic A rings and pyrrolo C rings, and in the degree of saturation of the C ring. In the B-ring, there is generally an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11α position which provides them with a right-handed twist when viewed from the C ring towards the A ring. The PBD examples provided herein may be conjugated to the anti-EGFR antibodies of the invention. Further examples of PBDs which may be conjugated to the anti-EGFR antibodies of the invention can be found, for example, in U.S. Patent Application Publication Nos. 2013/0028917 A1 and 2013/0028919 A1, in U.S. Pat. No. 7,741,319 B2, and in WO 2011/130598 A1 and WO 2006/111759 A1, each of which are incorporated herein by reference in their entirety.

A representative PBD dimer having the following formula II may be conjugated to the anti-EGFR antibodies of the invention:

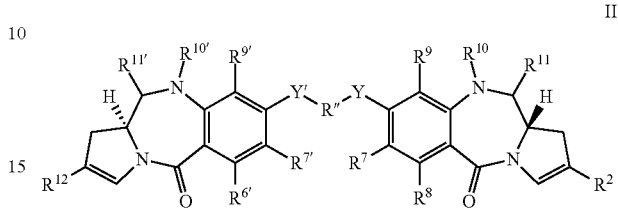

wherein:

$R^2$ is of formula III:

where A is a $C_{5-7}$ aryl group, X is a group conjugated to the Linker unit selected from the group consisting of —O—, —S—, —C(O)O—, —C(O)—, —NH(C=O)—, and —N($R^N$)—, wherein $R^N$ is selected from the group consisting of H, $C_{1-4}$ alkyl and $(C_2H_4O)_mCH_3$, where m is 1 to 3, and either:

(i) $Q^1$ is a single bond, and $Q^2$ is selected from the group consisting of a single bond and —Z—$(CH_2)_n$—, where Z is selected from the group consisting of a single bond, O, S and NH and n is from 1 to 3; or (ii) $Q^1$ is —C—H=CH—, and $Q^2$ is a single bond;

$R^{12}$ is a $C_{5-10}$ aryl group, optionally substituted by one or more substituents selected from the group consisting of halo, nitro, cyano, $C_{1-12}$ alkoxy, $C_{3-20}$ heterocycloalkoxy, $C_{5-20}$ aryloxy, heteroaryloxy, alkylalkoxy, arylalkoxy, alkylaryloxy, heteroarylalkoxy, alkylheteroaryloxy, $C_{1-7}$alkyl, $C_{3-7}$ heterocyclyl and bis-oxy-$C_{1-3}$ alkylene;

$R^6$ and $R^9$ are independently selected from the group consisting of H, R, OH, OR, SH, SR, $NH_2$, NHR, NRR', nitro, $Me_3Sn$ and halo;

where R and R' are independently selected from the group consisting of optionally substituted $C_{1-12}$ alkyl, $C_{3-20}$ heterocyclyl and $C_{5-20}$ aryl groups;

$R^7$ is selected from the group consisting of H, R, OH, OR, SH, SR, $NH_2$, NHR, NHRR', nitro, $Me_3Sn$ and halo;

either:

(a) $R^{10}$ is H, and $R^{11}$ is OH, $OR^A$, where $R^A$ is $C_{1-4}$ alkyl:

(b) $R^{10}$ and $R^{11}$ form a nitrogen-carbon double bond between the nitrogen and carbon atoms to which they are bound; or (c) $R^{10}$ is H and $R^{11}$ is $SO_zM$, where z is 2 or 3;

R" is a $C_{3-12}$ alkylene group, which chain may be interrupted by one or more heteroatoms, selected from the group consisting of O, S, NH, and an aromatic ring;

Y and Y' are is selected from the group consisting of O, S, and NH;

$R^{6'}$, $R^{7'}$, $R^{9'}$ are selected from the same groups as $R^6$, $R^7$ and $R^9$ respectively and $R^{10'}$ and $R^{11'}$ are the same as $R^{10}$ and $R^{11}$, and each M is a monovalent pharmaceutically acceptable cation or both M groups together are a divalent pharmaceutically acceptable cation.

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$); $O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$); $O_2$: dioxolane ($C_5$), dioxane ($C_6$), and dioxepane ($C_7$); $O_3$: trioxane ($C_6$); $N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$); $N_1S_1$: thiazoline ($C_5$), thiazolidine ($C_5$), thiomorpholine ($C_6$); $N_2O_1$: oxadiazine ($C_6$); $O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

In one embodiment, the anti-EGFR antibodies of the invention may be conjugated to a PBD dimer having the following formula:

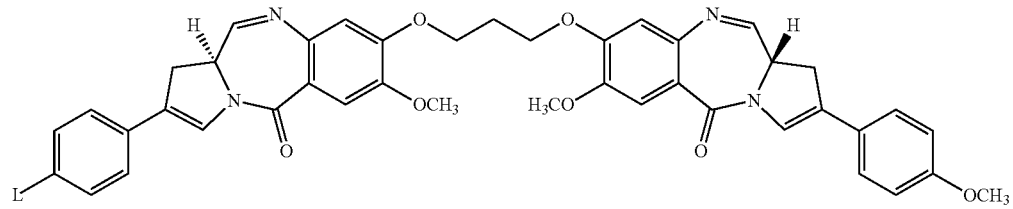

wherein the above structure describes the PBD dimer SG2202 (ZC-207) and is conjugated to the anti-EGFR antibody of the invention via a linker L. SG2202 (ZC-207) is disclosed in, for example, U.S. Patent App. Pub. No. 2007/0173497, which is incorporated herein by reference in its entirety.

Figure 21:
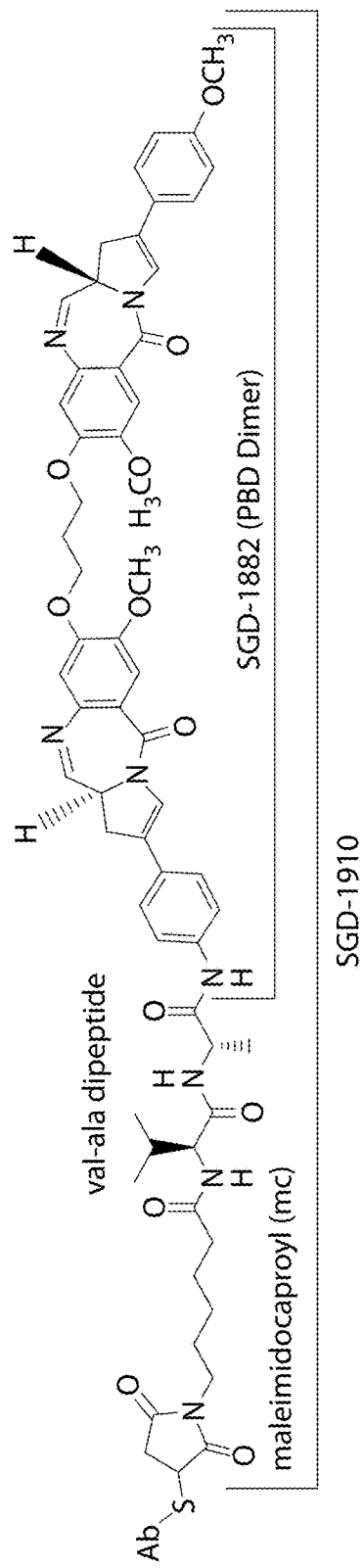
FIG. 21 depicts the structure of a PBD dimer (SGD-1882) conjugated to an antibody (Ab) via a maleimidocaproyl-valine-alanine linker (collectively referred to as SGD-1910).

In another embodiment, a PBD dimer, SGD-1882, is conjugated to anti-EGFR antibody of the invention via a drug linker, as depicted in FIG. 21. SGD-1882 is disclosed in Sutherland et al. (2013) Blood 122(8):1455 and in U.S Patent App. Pub. No. 2013/0028919, which is incorporated herein be reference in its entirety. As described in FIG. 21, the PBD dimer SGD-1882 may be conjugated to an antibody via an mc-val-ala-dipeptide linker (collectively referred to as SGD-1910 in FIG. 21). In a certain embodiment, an anti-EGFR antibody, as disclosed herein, is conjugated to the PBD dimer described in FIG. 21. Thus, in a further embodiment, the invention includes an anti-EGFR antibody, as disclosed herein, conjugated to a PBD dimer via a mc-val-ala-dipeptide linker, as described in FIG. 21.

In certain embodiments, the invention includes an anti-EGFR antibody comprising a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6, conjugated to a PBD, including, but not limited to, the PBD dimer described in FIG. 21. In certain embodiments, the invention includes an anti-EGFR antibody comprising the heavy chain variable region of AbA as defined by the amino acid sequence set forth in SEQ ID NO: 9, and a light chain variable region comprising the amino acid sequence of SEQ ID NO: 5, wherein the antibody is conjugated to a PBD, such as, but not limited to, the exemplary PBD dimer of FIG. 21.

b. Anthracyclines

Anti-EGFR antibodies of the invention may be conjugated to at least one anthracycline. Anthracyclines are a subclass of antitumor antibiotics isolated from bacteria of the genus *Streptomyces*. Representative examples include, but are not limited to daunorubicin (Cerubidine, Bedford Laboratories), doxorubicin (Adriamycin, Bedford Laboratories; also referred to as doxorubicin hydrochloride, hydroxydaunorubicin, and Rubex), epirubicin (Ellence, Pfizer), and idarubicin (Idamycin; Pfizer Inc.). Thus, in one embodiment, the anti-EGFR antibody of the invention is conjugated to at least one anthracycline, e.g., doxorubicin.

c. Calicheamicins

The anti-EGFR antibodies of the invention may be conjugated to at least one calicheamicin. Calicheamicins are a family of enediyne antibiotics derived from the soil organism *Micromonospora echinospora*. Calicheamicins bind the minor groove of DNA and induce double-stranded DNA breaks, resulting in cell death with a 100 fold increase over other chemotherapeutics (Damle et al. (2003) *Curr Opin Pharmacol* 3:386). Preparation of calicheamicins that may be used as drug conjugates in the invention have been described, see U.S. Pat. Nos. 5,712,374; 5,714,586; 5,739,116; 5,767,285; 5,770,701; 5,770,710; 5,773,001; and 5,877,296. Structural analogues of calicheamicin which may be used include, but are not limited to, $\gamma_1^I$, $\alpha_2^I$, $\alpha_3^I$, N-acetyl-$\gamma_1^1$, PSAG and $\theta^I_1$ (Hinman et al., Cancer Research 53:3336-3342 (1993), Lode et al., Cancer Research 58:2925-2928 (1998) and the aforementioned U.S. Pat. Nos. 5,712,374; 5,714,586; 5,739,116; 5,767,285; 5,770,701; 5,770,710; 5,773,001; and 5,877,296). Thus, in one embodiment, the anti-EGFR antibody of the invention is conjugated to at least one calicheamicin.

d. Duocarmycins

Anti-EGFR antibodies of the invention may be conjugated to at least one duocarmycin. Duocarmycins are a subclass of antitumor antibiotics isolated from bacteria of the genus *Streptomyces*. (see Nagamura and Saito (1998) *Chemistry of Heterocyclic Compounds*, Vol. 34, No. 12). Duocarmycins bind to the minor groove of DNA and alkylate the nucleobase adenine at the N3 position (Boger (1993) *Pure and Appl Chem* 65(6):1123; and Boger and Johnson (1995) *PNAS USA* 92:3642). Synthetic analogs of duocarmycins include, but are not limited to, adozelesin, bizelesin, and carzelesin. Thus, in one embodiment, the anti-EGFR antibody of the invention is conjugated to at least one duocarmycin.

e. Other Antitumor Antibiotics

In addition to the foregoing, additional antitumor antibiotics that may be used in the anti-EGFR ADCs of the invention include bleomycin (Blenoxane, Bristol-Myers Squibb), mitomycin, and plicamycin (also known as mithramycin).

3. Immunomodulating Agents

In one aspect, anti-EGFR antibodies of the invention may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, *bacillus* calmette-guerin (BCG) and levamisole (Ergamisol). Other examples of immunomodulating agents that may be used in the ADCs of the invention include, but are not limited to, cancer vaccines, cytokines, and immunomodulating gene therapy.

a. Cancer Vaccines

Anti-EGFR antibodies of the invention may be conjugated to a cancer vaccine. As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant invention, administering an ADC comprising an anti-EGFR antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-EGFR ADCs of the invention include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-EGFR antibody of the invention is conjugated to at least one cancer vaccine that is either an immunostimulator or is an immunosuppressant.

b. Cytokines

The anti-EGFR antibodies of the invention may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs of the invention include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the invention provides an ADC comprising an anti-EGFR antibody described herein and a cytokine.

c. Colony-Stimulating Factors (CSFs)

The anti-EGFR antibodies of the invention may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-EGFR ADCs of the invention include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, the invention provides an ADC comprising an anti-EGFR antibody described herein and a CSF.

4. Gene Therapy

The anti-EGFR antibody of the invention may be conjugated to at least one nucleic acid (directly or indirectly via a carrier) for gene therapy. Gene therapy generally refers to the introduction of genetic material into a cell whereby the genetic material is designed to treat a disease. As it pertains to immunomoduatory agents, gene therapy is used to stimulate a subject's natural ability to inhibit cancer cell proliferation or kill cancer cells. In one embodiment, the anti-EGFR ADC of the invention comprises a nucleic acid encoding a functional, therapeutic gene that is used to replace a mutated or otherwise dysfuntional (e.g. truncated) gene associated with cancer. In other embodiments, the anti-EGFR ADC of the invention comprises a nucleic acid that encodes for or otherwise provides for the production of a therapeutic protein to treat cancer. The nucleic acid that encodes the therapeutic gene may be directly conjugated to the anti-EGFR antibody, or alternatively, may be conjugated to the anti-EGFR antibody through a carrier. Examples of carriers that may be used to deliver a nucleic acid for gene therapy include, but are not limited to, viral vectors or liposomes.

5. Alkylating Agents

The anti-EGFR antibodies of the invention may be conjugated to one or more alkylating agent(s). Alkylating agents are a class of antineoplastic compounds that attaches an alkyl group to DNA. Examples of alkylating agents that may be used in the ADCs of the invention include, but are not limited to, alkyl sulfonates, ethylenimimes, methylamine derivatives, epoxides, nitrogen mustards, nitrosoureas, triazines and hydrazines.

a. Alkyl Sulfonates

The anti-EGFR antibodies of the invention may be conjugated to at least one alkyl sulfonate. Alkyl sulfonates are a subclass of alkylating agents with a general formula: $R-SO_2-O-R^1$, wherein R and $R^1$ are typically alkyl or aryl groups. A representative example of an alkyl sulfonate includes, but is not limited to, busulfan (Myleran, GlaxoSmithKline; Busulfex IV, PDL BioPharma, Inc.).

b. Nitrogen Mustards

The anti-EGFR antibodies of the invention may be conjugated to at least one nitrogen mustard. Representative examples of this subclass of anti-cancer compounds include, but are not limited to chlorambucil (Leukeran, GlaxoSmithKline), cyclophosphamide (Cytoxan, Bristol-Myers Squibb; Neosar, Pfizer, Inc.), estramustine (estramustine phosphate sodium or Estracyt), Pfizer, Inc.), ifosfamide (Ifex, Bristol-Myers Squibb), mechlorethamine (Mustargen, Lundbeck Inc.), and melphalan (Alkeran or L-Pam or phenylalanine mustard; GlaxoSmithKline).

c. Nitrosoureas

The anti-EGFR antibody of the invention may be conjugated to at least one nitrosourea. Nitrosoureas are a subclass of alkylating agents that are lipid soluble. Representative examples include, but are not limited to, carmustine (BCNU [also known as BiCNU, N,N-Bis(2-chloroethyl)-N-nitrosourea, or 1,3-bis(2-chloroethyl)-l-nitrosourea], Bristol-Myers Squibb), fotemustine (also known as Muphoran), lomustine (CCNU or 1-(2-chloro-ethyl)-3-cyclohexyl-1-nitrosourea, Bristol-Myers Squibb), nimustine (also known as ACNU), and streptozocin (Zanosar, Teva Pharmaceuticals).

d. Triazines and Hydrazines

The anti-EGFR antibody of the invention may be conjugated to at least one triazine or hydrazine. Triazines and hydrazines are a subclass of nitrogen-containing alkylating agents. In some embodiments, these compounds spontaneously decompose or can be metabolized to produce alkyl diazonium intermediates that facilitate the transfer of an alkyl group to nucleic acids, peptides, and/or polypeptides, thereby causing mutagenic, carcinogenic, or cytotoxic effects. Representative examples include, but are not limited to dacarbazine (DTIC-Dome, Bayer Healthcare Pharmaceuticals Inc.), procarbazine (Mutalane, Sigma-Tau Pharmaceuticals, Inc.), and temozolomide (Temodar, Schering Plough).

e. Other Alkylating Agents

The anti-EGFR antibodies of the invention may be conjugated to at least one ethylenimine, methylamine derivative, or epoxide. Ethylenimines are a subclass of alkylating agents that typically containing at least one aziridine ring. Epoxides represent a subclass of alkylating agents that are characterized as cyclic ethers with only three ring atoms.

Representatives examples of ethylenimines include, but are not limited to thiopeta (Thioplex, Amgen), diaziquone (also known as aziridinyl benzoquinone (AZQ)), and mitomycin C. Mitomycin C is a natural product that contains an aziridine ring and appears to induce cytotoxicity through cross-linking DNA (Dorn R T, et al. *Cancer Res.* 1985; 45:3510; Kennedy K A, et al *Cancer Res.* 1985; 45:3541). Representative examples of methylamine derivatives and their analogs include, but are not limited to, altretamine (Hexalen, MGI Pharma, Inc.), which is also known as hexamethylamine and hexastat. Representative examples of epoxides of this class of anti-cancer compound include, but are not limited to dianhydrogalactitol. Dianhydrogalactitol (1,2:5,6-dianhydrodulcitol) is chemically related to the aziridines and generally facilitate the transfer of an alkyl group through a similar mechanism as described above. Dibromodulcitol is hydrolyzed to dianhydrogalactitol and thus is a pro-drug to an epoxide (Sellei C, et al. *Cancer Chemother Rep.* 1969; 53:377).

6. Antiangiogenic Agents

In one aspect, the anti-EGFR antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs of the invention include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

7. Antimetabolites

The anti-EGFR antibodies of the invention may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolites that may be used in the ADCs of the invention include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

a. Antifolates

The anti-EGFR antibodies of the invention may be conjugated to at least one antifolate. Antifolates are a subclass of antimetabolites that are structurally similar to folate. Representative examples include, but are not limited to, methotrexate, 4-amino-folic acid (also known as aminopterin and 4-aminopteroic acid), lometrexol (LMTX), pemetrexed (Alimpta, Eli Lilly and Company), and trimetrexate (Neutrexin, Ben Venue Laboratories, Inc.)

b. Purine Antagonists

The anti-EGFR antibodies of the invention may be conjugated to at least one purine antagonist. Purine analogs are a subclass of antimetabolites that are structurally similar to the group of compounds known as purines. Representative examples of purine antagonists include, but are not limited to, azathioprine (Azasan, Salix; Imuran, GlaxoSmithKline), cladribine (Leustatin [also known as 2-CdA], Janssen Biotech, Inc.), mercaptopurine (Purinethol [also known as 6-mercaptoethanol], GlaxoSmithKline), fludarabine (Fludara, Genzyme Corporation), pentostatin (Nipent, also known as 2'-deoxycoformycin (DCF)), 6-thioguanine (Lanvis [also known as thioguanine], GlaxoSmithKline).

c. Pyrimidine Antagonists

The anti-EGFR antibodies of the invention may be conjugated to at least one pyrimidine antagonist. Pyrimidine antagonists are a subclass of antimetabolites that are structurally similar to the group of compounds known as purines. Representative examples of pyrimidine antagonists include, but are not limited to azacitidine (Vidaza, Celgene Corporation), capecitabine (Xeloda, Roche Laboratories), Cytarabine (also known as cytosine arabinoside and arabinosylcytosine, Bedford Laboratories), decitabine (Dacogen, Eisai Pharmaceuticals), 5-fluorouracil (Adrucil, Teva Pharmaceuticals; Efudex, Valeant Pharmaceuticals, Inc), 5-fluoro-2'-deoxyuridine 5'-phosphate (FdUMP), 5-fluorouridine triphosphate, and gemcitabine (Gemzar, Eli Lilly and Company).

8. Boron-Containing Agents

The anti-EGFR antibody of the invention may be conjugated to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

9. Chemoprotective Agents

The anti-EGFR antibodies of the invention may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

10. Hormone Agents

The anti-EGFR antibody of the invention may be conjugated to at least one hormone agent. A hormone agent (including synthetic hormones) is a compound that interferes with the production or activity of endogenously produced hormones of the endocrine system. In some embodiments, these compounds interfere with cell growth or produce a cytotoxic effect. Non-limiting examples include androgens, estrogens, medroxyprogesterone acetate (Provera, Pfizer, Inc.), and progestins.

11. Antihormone Agents

The anti-EGFR antibodies of the invention may be conjugated to at least one antihormone agent. An "antihormone" agent is an agent that suppresses the production of and/or prevents the function of certain endogenous hormones. In one embodiment, the antihormone agent interferes with the activity of a hormone selected from the group comprising androgens, estrogens, progesterone, and goanadotropin-releasing hormone, thereby interfering with the growth of various cancer cells. Representative examples of antihormone agents include, but are not limited to, aminoglutethimide, anastrozole (Arimidex, AstraZeneca Pharmaceuticals), bicalutamide (Casodex, AstraZeneca Pharmaceuticals), cyproterone acetate (Cyprostat, Bayer PLC), degarelix (Firmagon, Ferring Pharmaceuticals), exemestane (Aromasin, Pfizer Inc.), flutamide (Drogenil, Schering-Plough Ltd), fulvestrant (Faslodex, AstraZeneca Pharmaceuticals), goserelin (Zolodex, AstraZeneca Pharmaceuticals), letrozole (Femara, Novartis Pharmaceuticals Corporation), leuprolide (Prostap), lupron, medroxyprogesterone acetate (Provera, Pfizer Inc.), Megestrol acetate (Megace, Bristol-Myers Squibb Company), tamoxifen (Nolvadex, AstraZeneca Pharmaceuticals), and triptorelin (Decapetyl, Ferring).

12. Corticosteroids

The anti-EGFR antibodies of the invention may be conjugated to at least one corticosteroid. Corticosteroids may be used in the ADCs of the invention to decrease inflammation. An example of a corticosteroid includes, but is not limited to, a glucocorticoid, for example, prednisone (Deltasone, Pharmacia & Upjohn Company, a division of Pfizer, Inc.).

13. Photoactive Therapeutic Agents

The anti-EGFR antibodies of the invention may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

14. Oligonucleotides

The anti-EGFR antibodies of the invention may be conjugated to at least one oligonucleotide. Oligonucleotides are made of short nucleic acid chains that work by interfering with the processing of genetic information. In some embodiments, the oligonucleotides for use in ADCs are unmodified single-stranded and/or double-stranded DNA or RNA molecules, while in other embodiments, these therapeutic oligonucleotides are chemically-modified single-stranded and/or double-stranded DNA or RNA molecules. In one embodiment, the oligonulceotides used in the ADCs are relatively short (19-25 nucleotides) and hybridize to a unique nucleic acid sequence in the total pool of nucleic acid targets present in cells. Some of the important oligonucleotide technologies include the antisense oligonucleotides (including RNA interference (RNAi)), aptamers, CpG oligonucleotides, and ribozymes.

a. Antisense Oligonucleotides

The anti-EGFR antibody of the invention may be conjugated to at least one antisense oligonucleotide. Antisense oligonucleotides are designed to bind to RNA through Watson-Crick hybridization. In some embodiments the antisense oligonucleotide is complementary to a nucleotide encoding a region, domain, portion, or segment of EGFR. In some embodiments, the antisense oligonucleotide comprises from about 5 to about 100 nucleotides, from about 10 to about 50 nucleotides, from about 12 to about 35, and from about 18 to about 25 nucleotides. In some embodiments, the oligonucleotide is at least 50%, at least 60%, at least 70%, at least 80%, at least 90%, at least 95%, at least 96%, at least 97%, at least 98%, at least 99%, or at least 100% homologous to a region, portion, domain, or segment of the EGFR gene. In some embodiments there is substantial sequence homology over at least 15, 20, 25, 30, 35, 40, 50, or 100 consecutive nucleotides of the EGFR gene. In preferred embodiments, the size of these antisense oligonucleotides ranges from 12 to 25 nucleotides in length, with the majority of antisense oligonucleotides being 18 to 21 nucleotides in length. There are multiple mechanisms that can be exploited to inhibit the function of the RNA once the oligonucleotide binds to the target RNA (Crooke S T. (1999). *Biochim. Biophys. Acta,* 1489, 30-42). The best-characterized antisense mechanism results in cleavage of the targeted RNA by endogenous cellular nucleases, such as RNase H or the nuclease associated with the RNA interference mechanism. However, oligonucleotides that inhibit expression of the target gene by non-catalytic mechanisms, such as modulation of splicing or translation arrest, can also be potent and selective modulators of gene function.

Another RNase-dependent antisense mechanism that has recently received much attention is RNAi (Fire et al. (1998). *Nature,* 391, 806-811; Zamore P D. (2002). *Science,* 296, 1265-1269.). RNA interference (RNAi) is a post-transcriptional process where a double stranded RNA inhibits gene expression in a sequence specific fashion. In some embodiments, the RNAi effect is achieved through the introduction of relatively longer double-stranded RNA (dsRNA), while in preferred embodiments, this RNAi effect is achieved by the introduction of shorter double-stranded RNAs, e.g. small interfering RNA (siRNA) and/or microRNA (miRNA). In yet another embodiment, RNAi can also be achieved by introducing of plasmid that generate dsRNA complementary to target gene. In each of the foregoing embodiments, the double-stranded RNA is designed to interfere with the gene expression of a particular the target sequence within cells. Generally, the mechanism involves conversion of dsRNA into short RNAs that direct ribonucleases to homologous mRNA targets (summarized, Ruvkun, *Science* 2294:797

(2001)), which then degrades the corresponding endogenous mRNA, thereby resulting in the modulation of gene expression. Notably, dsRNA has been reported to have antiproliferative properties, which makes it possible also to envisage therapeutic applications (Aubel et al., *Proc. Natl. Acad. Sci., USA* 88:906 (1991)). For example, synthetic dsRNA has been shown to inhibit tumor growth in mice (Levy et al. *Proc. Nat. Acad. Sci. USA*, 62:357-361 (1969)), is active in the treatment of leukemic mice (Zeleznick et al., *Proc. Soc. Exp. Biol. Med.* 130:126-128 (1969)), and inhibits chemically induced tumorigenesis in mouse skin (Gelboin et al., *Science* 167:205-207 (1970)). Thus, in a preferred embodiment, the invention provides for the use of antisense oligonucleotides in ADCs for the treatment of breast cancer. In other embodiments, the invention provides compositions and methods for initiating antisense oligonucleotide treatment, wherein dsRNA interferes with target cell expression of EGFR at the mRNA level. dsRNA, as used above, refers to naturally-occurring RNA, partially purified RNA, recombinantly produced RNA, synthetic RNA, as well as altered RNA that differs from naturally-occurring RNA by the inclusion of non-standard nucleotides, non-nucleotide material, nucleotide analogs (e.g. locked nucleic acid (LNA)), deoxyribonucleotides, and any combination thereof. RNA of the invention need only be sufficiently similar to natural RNA that it has the ability to mediate the antisense oligonucleotide-based modulation described herein.

b. Aptamers

The anti-EGFR antibodies of the invention may be conjugated to at least one aptamer. An aptamer is a nucleic acid molecule that has been selected from random pools based on its ability to bind other molecules. Like antibodies, aptamers can bind target molecules with extraordinary affinity and specificity. In many embodiments, aptamers assume complex, sequence-dependent, three-dimensional shapes that allow them to interact with a target protein, resulting in a tightly bound complex analogous to an antibody-antigen interaction, thereby interfering with the function of said protein. The particular capacity of aptamers to bind tightly and specifically to their target protein underlines their potential as targeted molecular therapies.

c. CpG Oligonucleotides

The anti-EGFR antibodies of the invention may be conjugated to at least one CpG oligonucleotide. Bacterial and viral DNA are known to be a strong activators of both the innate and specific immunity in humans. These immunologic characteristics have been associated with unmethylated CpG dinucleotide motifs found in bacterial DNA. Owing to the fact that these motifs are rare in humans, the human immune system has evolved the ability to recognize these motifs as an early indication of infection and subsequently initiate immune responses. Therefore, oligonucleotides containing this CpG motif can be exploited to initiate an antitumor immune response.

d. Ribozymes

The anti-EGFR antibody of the invention may be conjugated to at least one ribozyme. Ribozymes are catalytic RNA molecules ranging from about 40 to 155 nucleotides in length. The ability of ribozymes to recognize and cut specific RNA molecules makes them potential candidates for therapeutics. A representative example includes angiozyme.

15. Radionuclide Agents (Radioactive Isotopes)

The anti-EGFR antibodies of the invention may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er; $^{194}$Ir, $^{198}$Au, $^{199}$Au, an $^{211}$Pb. Also preferred are radionuclides that substantially decay with Auger-emitting particles. For example, Co-58, Ga-67, Br-80m, Tc-99m, Rh-103m, Pt-109, In-111 1, Sb-119, I-125, Ho-161, Os-189m and Ir-192. Decay energies of useful beta-particle-emitting nuclides are preferably Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$H, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb and the like.

16. Radiosensitizers

The anti-EGFR antibodies of the invention may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

16. Topoisomerase Inhibitors

The anti-EGFR antibodies of the invention may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

17. Tyrosine Kinase Inhibitors

The anti-EGFR antibodies of the invention may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs of the invention include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

18. Other Agents

Examples of other agents that may be used in the ADCs of the invention include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-EGFR ADCs of the invention are not exclusive, in that certain examples of drugs may be found in more than one category, e.g., ansamitocins are both mitotic inhibitors and antitumor antibiotics.

All stereoisomers of the above drug moieties are contemplated for the compounds of the invention, i.e. any combination of R and S configurations at the chiral carbons of D.

The above agents (i.e., naked agents not conjugated to an antibody) may also be used in combination therapies with the anti-EGFR antibodies described herein. In one embodiment, anti-EGFR antibodies or ADCs are used with any of the foregoing agents in a combination therapy to treat cancer, where the agent is administered prior to, at the same time as, or following administration of the anti-EGFR antibody or ADC to the subject.

B. Anti-EGFR ADCs: Exemplary Linkers

An anti-EGFR ADC comprises an anti-EGFR antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components. For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine. e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Exemplary linker components include 6-maleimidocaproyl, maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl)cyclohexane-1 carboxylate ("MCC").

In one aspect, an anti-EGFR antibody is conjugated to an auristatin, e.g., MMAE, via a linker comprising maleimidocaproyl ("mc"), valine citrulline (val-cit or "vc"), and PABA (referred to as a "mc-vc-PABA linker"). Maleimidocaproyl acts as a linker to the anti-EGFR antibody and is not cleavable. Val-cit is a dipeptide that is an amino acid unit of the linker and allows for cleavage of the linker by a protease, specifically the protease cathepsin B. Thus, the val-cit component of the linker provides a means for releasing the auristatin from the ADC upon exposure to the intracellular environment. Within the linker, p-aminobenzylalcohol (PABA) acts as a spacer and is self immolative, allowing for the release of the MMAE. The structure of the mc-vc-PABA-MMAE linker is provided in FIG. 11.

Suitable linkers include, for example, cleavable and non-cleavable linkers. A linker may be a "cleavable linker,"

facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in EGFR-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-EGFR ADCs described herein is a non-cleavable linker that promotes cellular internalization.

In some embodiments, the ADC has the following formula (formula I):

$$\text{Ab-(L-D)}_n \tag{I}$$

or a pharmaceutically acceptable salt or solvate thereof; wherein Ab is the antibody, e.g., anti-EGFR antibody AbA, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing EGFR; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the -D moieties are the same. In yet another embodiment, the -D moieties are different.

As described above, the linker may be a single moiety or may include two or more components. As such, in some embodiments, the ADC has the following formula (II):

Ab-(A$_a$-W$_w$—Y$_y$-D)$_n$      (II)

or a pharmaceutically acceptable salt or solvate thereof, wherein Ab is the antibody, e.g., anti-EGFR antibody AbA, and -A$_a$-W$_w$—Y$_y$— is a Linker (L) comprising three or more components, including -A-, which is is an optional Stretcher unit, a is 0 or 1, each —W— is independently an Amino Acid unit (or in some embodiments, a Glucuronide unit, See also US Publication No. 2012/0107332 A1), w is an integer ranging from 0 to 12, —Y— is a self-immolative spacer unit, y is 0, 1 or 2; -D is a drug moiety having, for example, cytostatic, cytotoxic, or otherwise therapeutic activity against the target cell, e.g., cell expressing EGFR; and n is an integer from 1 to 20.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

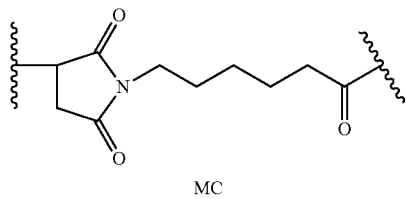 [SMILES: *C(=O)CCCCCN1C(=O)CC(*)C1=O]

MC

The stretcher unit (A), when present, is capable of linking an antibody to an amino acid unit (—W—), if present, to a spacer unit (—Y—), if present; or to a drug (-D) (see Formula II). Useful functional groups that can be present on the anti-EGFR antibodies described herein, either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of an anti-EGFR antibody. In another embodiment, sulfhydryl groups can be generated by reaction of an amino group of a lysine moiety of an anti-EGFR antibody with 2-iminothiolane (Traut's reagent) or other sulfhydryl generating reagents. In certain embodiments, the anti-EGFR antibody is a recombinant antibody and is engineered to carry one or more lysine moieties. In certain other embodiments, the recombinant anti-EGFR antibody is engineered to carry additional sulfhydryl groups, e.g., additional cysteines.

In one embodiment, the stretcher unit forms a bond with a sulfur atom of the antibody. The sulfur atom can be derived from a sulfhydryl group of an antibody. Representative stretcher units of this embodiment are depicted within the square brackets of Formulas Ma and Mb as shown below,

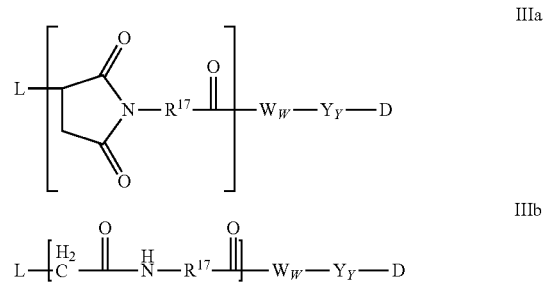

wherein L-, —W—, —Y—, -D, w and y are as defined above, and R$^{17}$ is selected from —C$_1$-C$_{10}$ alkylene-, —C$_1$-C$_{10}$ alkenylene-, —C$_1$-C$_{10}$ alkynylene-, carbocyclo-, —O—(C$_1$-C$_8$ alkylene)-, O—(C$_1$-C$_8$ alkenylene)-, —O—(C$_1$-C$_8$ alkynylene)-, -arylene-, —C$_1$-C$_{10}$ alkylene-arylene-, —C$_2$-C$_{10}$ alkenylene-arylene, —C$_2$-C$_{10}$ alkynylene-arylene, arylene-C$_1$-C$_{10}$ alkylene-, -arylene-C$_2$-C$_{10}$ alkenylene-, -arylene-C$_2$-C$_{10}$ alkynylene-, —C$_1$-C$_{10}$ alkylene-(carbocyclo)-, —C$_2$-C$_{10}$ alkenylene-(carbocyclo)-, C$_2$-C$_{10}$ alkynylene-(carbocyclo)-, -(carbocyclo)-C$_1$-C$_{10}$ alkylene-, -(carbocyclo)-C$_2$-C$_{10}$ alkenylene-, -(carbocyclo)-C$_2$-C$_{10}$ alkynylene, -heterocyclo-, —C$_1$-C$_{10}$ alkylene-(heterocyclo)-, —C$_2$-C$_{10}$ alkenylene-(heterocyclo)-, —C$_2$-C$_{10}$ alkynylene-(heterocyclo)-, -(heterocyclo)-C$_1$-C$_{10}$ alkylene-, -(heterocyclo)-C$_2$-C$_{10}$ alkenylene-, -(heterocyclo)-C$_1$-C$_{10}$ alkynylene-, —(CH$_2$CH$_2$O)$_r$—, or —(CH$_2$CH$_2$O)$_r$—CH$_2$—, and r is an integer ranging from 1-10, wherein said alkyl, alkenyl, alkynyl, alkylene, alkenylene, alkynyklene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynyklene, aryl, carbocyle, carbocyclo, heterocyclo, and arylene radicals, whether alone or as part of another group, are unsubstituted. In some embodiments, R$^{17}$ is selected from —C$_1$-C$_{10}$ alkylene-, -carbocyclo-, —O—(C$_1$-C$_8$ alkylene)-, -arylene-, —C$_1$-C$_{10}$ alkylene-arylene-, -arylene-C$_1$-C$_{10}$ alkylene-, —C$_1$-C$_{10}$ alkylene-(carbocyclo)-, -(carbocyclo)-C$_1$-C$_{10}$ alkylene-, —C$_3$-C$_8$ heterocyclo-, —C$_1$-C$_{10}$ alkylene-(heterocyclo)-, -(heterocyclo)-C$_1$-C$_{10}$ alkylene-, —(CH$_2$CH$_2$O)$_r$—, and —(CH$_2$CH$_2$O)$_r$—CH$_2$—; and r is an integer ranging from 1-10, wherein said alkylene groups are unsubstituted and the remainder of the groups are optionally substituted.

An illustrative stretcher unit is that of Formula IIIa wherein R$^{17}$ is —(CH$_2$)$_5$— as depicted below (see also U.S. Pat. No. 8,309,093).

Another illustrative stretcher unit is that of Formula IIIa wherein R$^{17}$ is —(CH$_2$CH$_2$O)$_r$—CH$_2$—; and r is 2, as depicted below (see also U.S. Pat. No. 8,309,093, incorporated by reference herein).

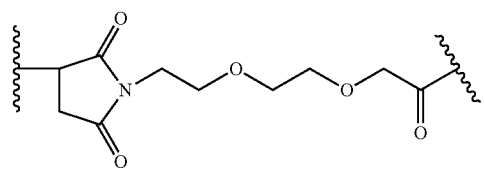 [SMILES: *C(=O)COCCOCCN1C(=O)CC(*)C1=O]

Another illustrative stretcher unit is that of Formula IIIa wherein $R^{17}$ is arylene- or arylene-$C_1$-$C_{10}$ alkylene-. In some embodiments, the aryl group is an unsubstituted phenyl group. Still, another illustrative stretcher unit is that of Formula IIIb wherein $R^{17}$ is —$(CH_2)_5$—, as depicted below (see also U.S. Pat. No. 8,309,093, incorporated by reference herein).

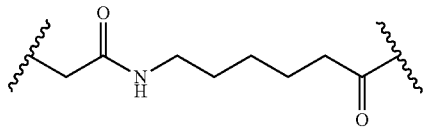 [SMILES: *CC(=O)NCCCCCC(*)=O]

In certain embodiments, the stretcher unit is linked to the anti-EGFR antibody via a disulfide bond between a sulfur atom of the anti-EGFR antibody unit and a sulfur atom of the stretcher unit. A representative stretcher unit of this embodiment is depicted within the square brackets of Formula IV (See below, and see also U.S. Pat. No. 8,309,093, incorporated by reference herein), wherein $R^{17}$, L-, —W—, —Y—, -D, w, and y are as defined above.

IV

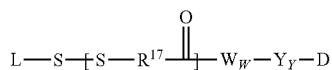

It should be noted that the S moiety in the formula shown below (see also U.S. Pat. No. 8,309,093, incorporated by reference herein) refers to a sulfur atom of the antibody, unless otherwise indicated by the context.

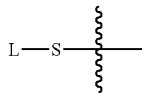

In yet other embodiments, the stretcher contains a reactive site that can form a bond with a primary or secondary amino group of an antibody. Examples of these reactive sites include but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative stretcher units of this embodiment are depicted within the square brackets of Formulas Va and Vb (See below (see also U.S. Pat. No. 8,309,093, incorporated by reference herein), wherein $R^{17}$, L-, —W—, —Y—, -D, w, and y are as defined above.

Va

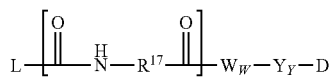

Vb

In some embodiments, the stretcher contains a reactive site that is reactive to a modified carbohydrate's (—CHO) group that can be present on an antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc (See below (see also U.S. Pat. No. 8,309,093, incorporated by reference herein), wherein —$R^{17}$—, L-, —W—, —Y—, -D, w and y are as defined as above.

VIa

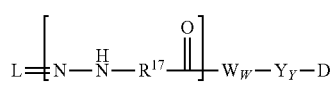

VIb

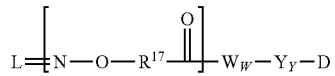

VIc

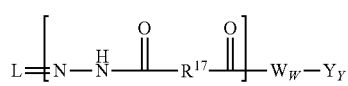

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the W amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Alternatively, in some embodiments, —W— is a glucuronide unit that links a stretcher unit to a spacer unit if the stretcher and spacer units are present, links a stretcher unit to the drug moiety if the spacer unit is absent, and links the linker unit to the drug if the stretcher and spacer units are absent. The glucuronide unit includes a site that can be cleaved by a β-glucuronidase enzyme (See also US 2012/0107332, incorporated by reference herein). In some embodiments, the glucuronide unit comprises a sugar moiety (Su) linked via a glycoside bond (—O'—) to a self-immolative group (Z) of the formula as depicted below (See also US 2012/0107332, incorporated by reference herein).

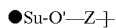

The glycosidic bond (—O'—) is typically a β-glucuronidase-cleavage site, such as a bond cleavable by human, lysosomal β-glucuronidase. In the context of a glucuronide unit, the term "self-immolative group" refers to a di- or tri-functional chemical moiety that is capable of covalently linking together two or three spaced chemical moieties (i.e., the sugar moiety (via a glycosidic bond), a drug moiety (directly or indirectly via a spacer unit), and, in some embodiments, a linker (directly or indirectly via a stretcher unit) into a stable molecule. The self-immolative group will spontaneously separate from the first chemical moiety (e.g., the spacer or drug unit) if its bond to the sugar moiety is cleaved.

In some embodiments, the sugar moiety (Su) is cyclic hexose, such as a pyranose, or a cyclic pentose, such as a furanose. In some embodiments, the pyranose is a glucuronide or hexose. The sugar moiety is usually in the β-D conformation. In a specific embodiment, the pyranose is a β-D-glucuronide moiety (i.e., β-D-glucuronic acid linked to the self-immolative group —Z— via a glycosidic bond that is cleavable by β-glucuronidase). In some embodiments, the sugar moiety is unsubstituted (e.g., a naturally occurring cyclic hexose or cyclic pentose). In other embodiments, the sugar moiety can be a substituted β-D-glucuronide (i.e., glucuronic acid substituted with one or more group, such hydrogen, hydroxyl, halogen, sulfur, nitrogen or lower alkyl.

In some embodiments, the glucuronide unit has one of the formulas as depicted below (See also US 2012/0107332, incorporated by reference herein),

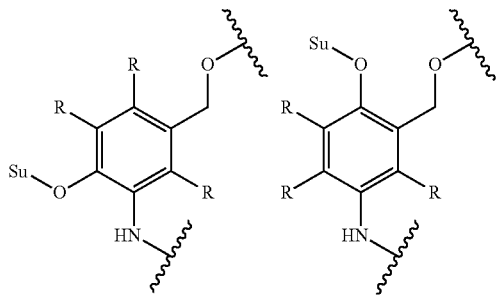

wherein Su is the sugar moiety, the glycosidic bond comprises the oxygen bond between Su and the self immolative group Z, and each R is independently hydrogen, halo (e.g., chloro, bromo, fluoro, etc), —CN, —NO$_2$, or other electron withdrawing or donating group, provided that the Glucuronide unit (and Z in particular) undergoes self-immolation upon cleavage of the glycosidic bond. In some embodiments, each R is independently hydrogen, halo (e.g., chloro, bromo, fluoro, etc), —CN or —NO$_2$.

In some embodiments, the glucuronide unit has one of the formulas as depicted below (see also US 2012/0107332, incorporated by reference herein),

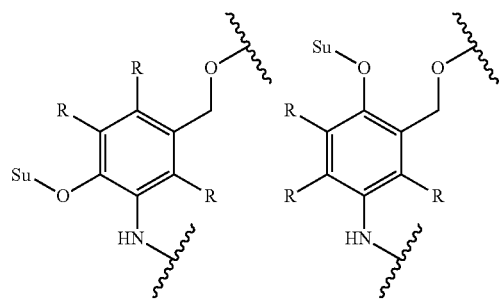

wherein Su is the Sugar moiety, the glycosidic bond (—O'—) comprises the oxygen bond between Su and the self immolative group Z, and each R is independently hydrogen.

In some embodiments, the self-immolative group (Z) is covalently linked to the sugar moiety, to the drug (directly or indirectly via the spacer unit(s)), and to the linker (directly or indirectly via the stretcher unit(s)). In some embodiments, a drug linker conjugate has the formula as depicted below (See also US 2012/0107332, incorporated by reference herein),

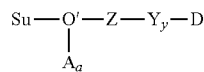

wherein Su, O', Z, Y, y, D, A and a are defined herein. Typically from 1 to 20 of such drug-linker conjugates can be linked to a linker.

In some embodiments, an ADC comprising the glucuronide unit has one of the formulas as depicted below (See also US 2012/0107332, incorporated by reference herein), wherein Su, Y, y, D, A, a, and L are defined as described herein.

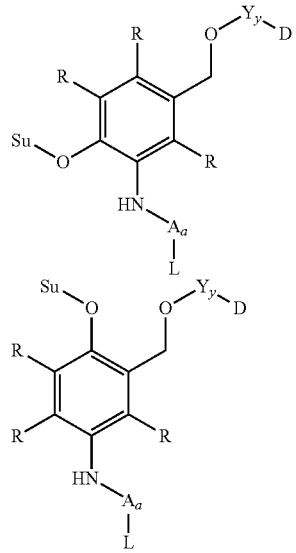

In some embodiments, an ADC comprising the glucuronide unit has the formula as depicted below (See also US 2012/0107332, incorporated by reference herein), wherein Y, y, D, A, a, and L are defined herein.

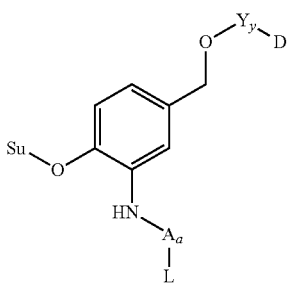

In some embodiments, an ADC comprising the Glucuronide unit has the formula as depicted below (See also US 2012/0107332, incorporated by reference herein), wherein Y, y, D and L are defined as described herein.

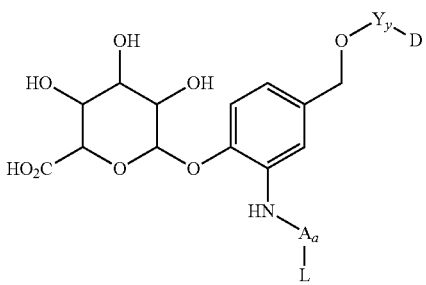

In some embodiments, an ADC comprising the Glucuronide unit has the formula as depicted below (See also US 2012/0107332, incorporated by reference herein), wherein Y, y, D and L are defined as described herein.

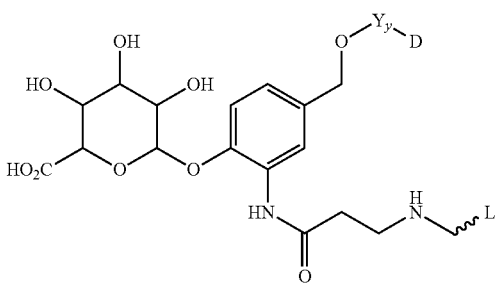

In some embodiments, an ADC comprising the Glucuronide unit has the formula as depicted below (See also US 2012/0107332 A1), wherein D is as described herein and mAb is a monoclonal antibody.

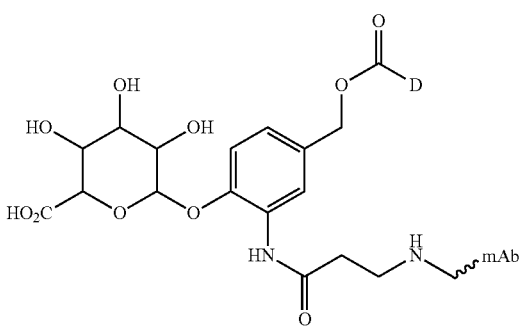

The spacer unit (—Y—), when present, links an amino acid unit (or Glucuronide unit, see also US 2012/0107332, incorporated by reference herein) to the drug moiety when an amino acid unit is present. Alternately, the spacer unit links the stretcher unit to the drug moiety when the amino acid unit is absent. The spacer unit may also links the drug unit to the antibody unit when both the amino acid unit and stretcher unit are absent.

Spacer units are of two general types: non self-immolative or self-immolative. A non self-immolative spacer unit is one in which part or all of the spacer unit remains bound to the drug moiety after cleavage, particularly enzymatic, of an amino acid unit (or glucuronide unit) from the antibody-drug conjugate. Examples of a non self-immolative spacer unit include, but are not limited to a (glycine-glycine) spacer unit and a glycine spacer unit (both depicted in Scheme 1 below (see also U.S. Pat. No. 8,309,093, incorporated by reference herein)).

Scheme 1

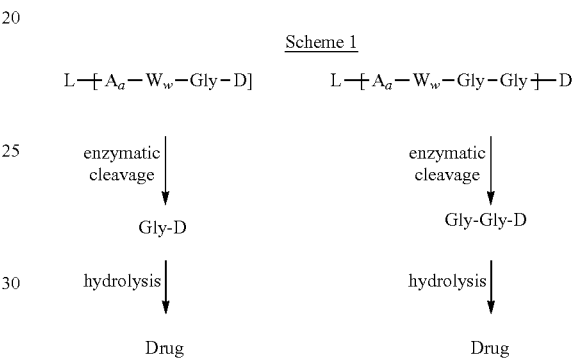

When a conjugate containing a glycine-glycine spacer unit or a glycine spacer unit undergoes enzymatic cleavage via an enzyme (e.g., a tumor-cell associated-protease, a cancer-cell-associated protease or a lymphocyte-associated protease), a glycine-glycine-drug moiety or a glycine-drug moiety is cleaved from L-$A_a$-$W_w$—. In one embodiment, an independent hydrolysis reaction takes place within the target cell, cleaving the glycine-drug moiety bond and liberating the drug.

In some embodiments, a non self-immolative spacer unit (—Y—) is -Gly-. In some embodiments, a non self-immolative spacer unit (—Y—) is -Gly-Gly-.

In one embodiment, a drug-linker conjugate is provided in which the spacer unit is absent (y=0), or a pharmaceutically acceptable salt or solvate thereof.

Alternatively, a conjugate containing a self-immolative spacer unit can allow for the release of the drug moiety. A self-immolative spacer unit will spontaneously separate from the second chemical moiety if its bond to the first moiety is cleaved.

In some embodiments, —$Y_y$— is a p-aminobenzyl alcohol (PAB) unit whose phenylene portion is substituted with $Q_m$, wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 below (see also U.S.

Pat. No. 8,309,093) depicts a possible mechanism of drug release of a PAB group which is attached directly to -D via a carbamate or carbonate group as described by Toki et al., 2002, J. Org. Chem. 67:1866-1872.

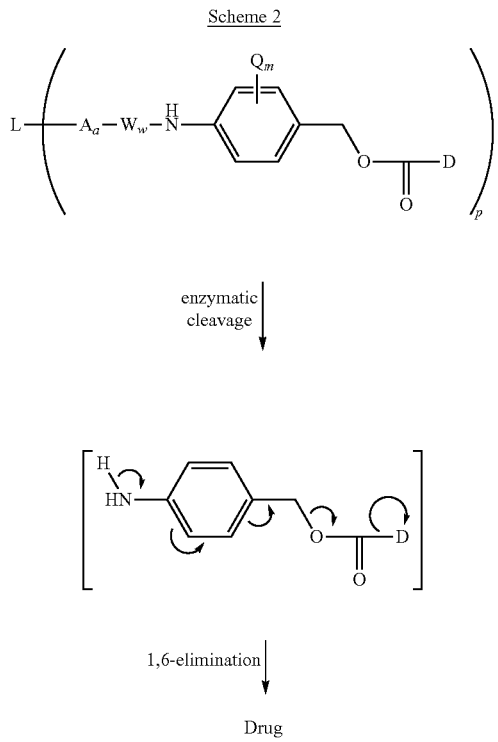

Scheme 2 enzymatic cleavage 1,6-elimination

Drug

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867). Elimination of amine-containing drugs that are substituted at the α-position of glycine (Kingsbury et al., 1984, J. Med. Chem. 27:1447) are also examples of self-immolative spacers.

In one aspect, spacer units (—$Y_y$—) are represented by Formulas (X)-(XII) (See below (see also U.S. Pat. No. 8,309,093) wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4.

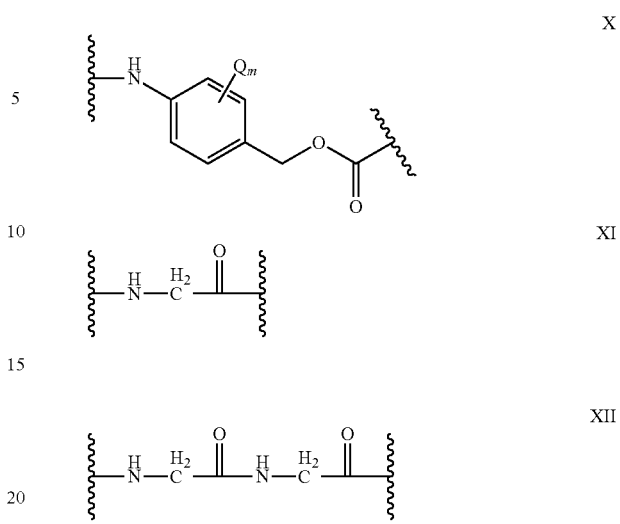

Other examples of self-immolative spacers include, but are not limited to, aromatic compounds that are electronically similar to the PAB group such as 2-aminoimidazol-5-methanol derivatives (see, e.g., Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, Chemistry Biology 2:223), appropriately substituted bicyclo[2.2.1] and bicyclo[2.2.2] ring systems (see, e.g., Storm et al., 1972, J. Amer. Chem. Soc. 94:5815) and 2-aminophenylpropionic acid amides (see, e.g., Amsberry et al., 1990, J. Org. Chem. 55:5867). Elimination of amine-containing drugs that are substituted at the a-position of glycine (see, e.g., Kingsbury et al., 1984, J. Med. Chem. 27:1447) are also examples of self-immolative spacers.

Other suitable spacer units are disclosed in Published U.S. Patent Application No. 2005-0238649, the disclosure of which is incorporated by reference herein.

Another approach for the generation of ADCs involves the use of heterobifunctional cross-linkers which link the anti-EGFR antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethylcarboxamido-2-pyridyldithio) butyrate (SSCPB)). The antibodies of the invention may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC. Preferably, the cross-linkers are compounds of the formula as depicted below (see also U.S. Pat. No. 6,913,748, incorporated by reference herein),

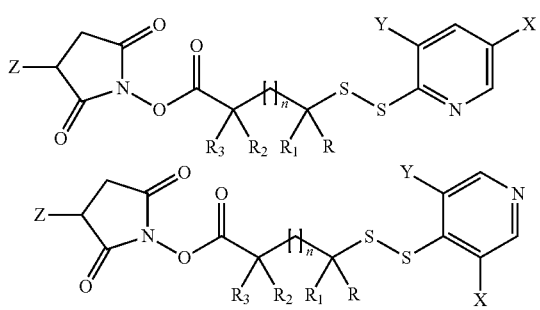

wherein R, $R_1$, $R_2$ and $R_3$ are the same or different and are H, methyl, ethyl, or linear, branched, or cyclic alkyl having 3 to 6 carbon atoms, n is 0 or an integer from 1 to 4, X and Y are the same or different and are H, $CONR_4R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and Z is $SO_3^-M^+$ or H, wherein $M^+$ represents a metal ion or a tetra alkyl ammonium ion, provided that when X and/or Y is $NO_2$, Z is not H. Additional heterobifunctional crosslinkers and methods of making ADCs using the same are described in U.S. Pat. No. 6,913,748, which is expressly incorporated by reference herein.

In one embodiment, charged linkers (also referred to as pro-charged linkers) are used to conjugate anti-EGFR antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

In a further embodiment, the ADC of the invention comprises a linker having the formula as depicted below (see also U.S. Pat. No. 8,236,319, incorporated by reference herein),

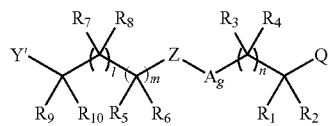

wherein Y' represents a functional group that enables reaction with an antibody; Q represents a functional group that enables linkage of a drug via a disulfide, thioether, thioester, peptide, hydrazone, ester, ether, carbamate or amide bond; $R_1$, $R_2$, $R_3$, $R_4$, $R_5$, $R_6$, $R_7$, $R_8$, $R_9$, and $R_{10}$ are the same or different and are H, linear alkyl having from 1 to 6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$, $X-SO_3^-$, $OPO_3^{2-}$, $X-OPO_3^{2-}$, $PO_3^{2-}$, $X-PO_3^{2-}$, $CO_2-$, cations, such as but not limited to, a nitrogen containing heterocycle, $N^+R_{11}R_{12}R_{13}$, or $X-N^+R_{11}R_{12}R_{13}$ or a phenyl, wherein: $R_{11}$, $R_{12}$, and $R_{13}$ are the same or different and are H, linear alkyl having from 1 to 6 carbon atoms, or branched or cyclic alkyl having from 3 to 6 carbon atoms and X represents phenyl or a linear alkyl having from 1 to 6 carbon atoms, or a branched or cyclic alkyl having from 3 to 6 carbon atoms; 1, m, and n are 0 or an integer from 1 to 4; A is a phenyl or substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$, $X-SO_3^-$, $OPO_3^{2-}$, $X-OPO_3^{2-}$, $PO_3^{2-}$, $X-PO_3^{2-}$, $CO_2-$, and cations, such as but not limited to, a nitrogen containing heterocycle, $N^+R_{11}R_{12}R_{13}$ or $X-N^+R_{11}R_{12}R_{13}$, wherein X has the same definition as above, and wherein g is 0 or 1; Z is an optional polyethyleneoxy unit of formula $(OCH_2CH_2)_p$, wherein p is 0 or an integer from 2 to about 1000, or F1-E1-P-E2-F2 unit in which E1 and E2 are the same or different and are C=O, O, or NR14, wherein $R_{14}$ is H, a linear alkyl having from 1 to 6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use in the invention includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used in the invention include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers for use in the invention may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly (lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfo-succinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the invention.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-EGFR antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Purification of Anti-EGFR ADCs

Purification of the ADCs may be achieved in such a way that ADCs having certain DARs are collected. For example, HIC resin may be used to separate high drug loaded ADCs from ADCs having optimal drug to antibody ratios (DARs), e.g. a DAR of 4 or less. In one embodiment, a hydrophobic resin is added to an ADC mixture such that undesired ADCs, i.e., higher drug loaded ADCs, bind the resin and can be selectively removed from the mixture. In certain embodiments, separation of the ADCs may be achieved by contacting an ADC mixture (e.g., a mixture comprising a drug loaded species of ADC of 4 or less and a drug loaded species of ADC of 6 or more) with a hydrophobic resin, wherein the amount of resin is sufficient to allow binding of the drug loaded species which is being removed from the ADC mixture. The resin and ADC mixture are mixed together, such that the ADC species being removed (e.g., a drug loaded species of 6 or more) binds to the resin and can be separated from the other ADC species in the ADC mixture. The amount of resin used in the method is based on a weight ratio between the species to be removed and the resin, where the amount of resin used does not allow for significant binding of the drug loaded species that is desired. Thus, methods may be used to reduce the average DAR 5.5 to less than 4. Further, the purification methods described herein may be used to isolate ADCs having any desired range of drug loaded species, e.g., a drug loaded species of 4 or less, a drug loaded species of 3 or less, a drug loaded species of 2 or less, a drug loaded species of 1 or less.

Certain species of molecule(s) binds to a surface based on hydrophobic interactions between the species and a hydrophobic resin. In one embodiment, method of the invention refers to a purification process that relies upon the intermixing of a hydrophobic resin and a mixture of ADCs, wherein the amount of resin added to the mixture determines which species (e.g., ADCs with a DAR of 6 or more) will bind. Following production and purification of an antibody from an expression system (e.g., a mammalian expression system), the antibody is reduced and coupled to a drug through a conjugation reaction. The resulting ADC mixture often contains ADCs having a range of DARs, e.g., 1 to 8. In one embodiment, the ADC mixture comprises a drug loaded species of 4 or less and a drug loaded species of 6 or more. According to the methods of the invention, the ADC mixture may be purified using a process, such as, but not limited to, a batch process, such that ADCs having a drug loaded species of 4 or less are selected and separated from ADCs having a higher drug load (e.g., ADCs having a drug loaded species of 6 or more). Notably, the purification methods described herein may be used to isolate ADCs having any desired range of DAR, e.g., a DAR of 4 or less, a DAR of 3 or less, a DAR of 2 or less.

Thus, in one embodiment, an ADC mixture comprising a drug loaded species of 4 or less and a drug loaded species of 6 or more may be contacted with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to an auristatin. In a separate embodiment, the method of the invention comprises contacting an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to an auristatin, wherein the hydrophobic resin weight is 3 to 12 times the weight of the drug loaded species of 6 or more in the ADC mixture.

The ADC separation method described herein method may be performed using a batch purification method. The batch purification process generally includes adding the ADC mixture to the hydrophobic resin in a vessel, mixing, and subsequently separating the resin from the supernatant. For example, in the context of batch purification, a hydrophobic resin may be prepared in or equilibrated to the desired equilibration buffer. A slurry of the hydrophobic resin may thus be obtained. The ADC mixture may then be contacted with the slurry to adsorb the specific species of ADC(s) to be separated by the hydrophobic resin. The solution comprising the desired ADCs that do not bind to the hydrophobic resin material may then be separated from the slurry, e.g., by filtration or by allowing the slurry to settle and removing the supernatant. The resulting slurry can be subjected to one or more washing steps. In order to elute bound ADCs, the salt concentration can be decreased. In one embodiment, the process used in the invention includes no more than 50 g of hydrophobic resin.

Thus, a batch method may be used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to an auristatin. In a separate embodiment, a batch method is used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to an auristatin, wherein the hydrophobic resin weight is 3 to 12 times the weight of the drug loaded species of 6 or more in the ADC mixture.

Alternatively, in a separate embodiment, purification may be performed using a circulation process, whereby the resin is packed in a container and the ADC mixture is passed over the hydrophobic resin bed until the specific species of ADC(s) to be separated have been removed. The supernatant (containing the desired ADC species) is then pumped from the container and the resin bed may be subjected to washing steps.

A circulation process may be used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to an auristatin. In a separate embodiment, a circulation process is used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to an auristatin, wherein the hydrophobic resin weight is 3 to 12 times the weight of the drug loaded species of 6 or more in the ADC mixture.

Alternatively, a flow through process may be used to purify an ADC mixture to arrive at a composition comprising a majority of ADCs having a certain desired DAR. In a flow through process, resin is packed in a container, e.g., a column, and the ADC mixture is passed over the packed resin such that the desired ADC species does not substantially bind to the resin and flows through the resin, and the undesired ADC species is bound to the resin. A flow through process may be performed in a single pass mode (where the ADC species of interest are obtained as a result of a single pass through the resin of the container) or in a multi-pass mode (where the ADC species of interest are obtained as a result of multiple passes through the resin of the container). The flow through process is performed such that the weight of resin selected binds to the undesired ADC population, and the desired ADCs (e.g., DAR 2-4) flow over the resin and are collected in the flow through after one or multiple passes.

A flow through process may be used to contact an ADC mixture comprising a drug loaded species of 4 or less and a drug loaded species of 6 or more with a hydrophobic resin, wherein the amount of hydrophobic resin contacted with the ADC mixture is sufficient to allow binding of the drug loaded species of 6 or more to the resin but does not allow significant binding of the drug load species of 4 or less, where the drug load species of 4 or less passes over the resin and is subsequently collected after one or multiple passes, such that the composition comprising the desired ADCs (e.g. DAR 2-4) is obtained, wherein the composition comprises less than 15% of the drug loaded species of 6 or more, and wherein the ADC comprises an antibody conjugated to an auristatin. In a separate embodiment, a flow through process is used to contact an ADC mixture comprising a drug loaded species of 4 or less and a drug loaded species of 6 or more with a hydrophobic resin by passing the ADC mixture over the resin, wherein the amount of hydrophobic resin contacted with the ADC mixture is sufficient to allow binding of the drug loaded species of 6 or more to the resin but does not allow significant binding of the drug load species of 4 or less, where the drug load species of 4 or less passes over the resin and is subsequently collected, such that the composition comprising ADCs is obtained, wherein the composition comprises less than 15% of the drug loaded species of 6 or more, and wherein the ADC comprises an antibody conjugated to an auristatin, wherein the amount of hydrophobic resin weight is 3 to 12 times the weight of the drug loaded species of 6 or more in the ADC mixture.

Following a flow through process, the resin may be washed with a one or more washes following in order to further recover ADCs having the desired DAR range (found in the wash filtrate). For example, a plurality of washes having decreasing conductivity may be used to further recover ADCs having the DAR of interest. The elution material obtained from the washing of the resin may be subsequently combined with the filtrate resulting from the flow through process for improved recovery of ADCs having the DAR of interest.

The aforementioned batch, circulation, and flow through process purification methods are based on the use of a hydrophobic resin to separate high vs. low drug loaded species of ADC. Hydrophobic resin comprises hydrophobic groups which interact with the hydrophobic properties of the ADCs. Hydrophobic groups on the ADC interact with hydrophobic groups within the hydrophobic resin. The more hydrophobic a protein is the stronger it will interact with the hydrophobic resin.

Hydrophobic resin normally comprises a base matrix (e.g., cross-linked agarose or synthetic copolymer material) to which hydrophobic ligands (e.g., alkyl or aryl groups) are coupled. Many hydrophobic resins are available commercially. Examples include, but are not limited to, Phenyl Sepharose™ 6 Fast Flow with low or high substitution (Pharmacia LKB Biotechnology, AB, Sweden); Phenyl Sepharose™ High Performance (Pharmacia LKB Biotechnology, AB, Sweden); Octyl Sepharose™ High Performance (Pharmacia LKB Biotechnology, AB, Sweden); Fractogel™ EMD Propyl or Fractogel™ EMD Phenyl columns (E. Merck, Germany); Macro-Prep™ Methyl or Macro-Prep™. t-Butyl Supports (Bio-Rad, California); WP HI-Propyl ($C_3$)™ (J. T. Baker, New Jersey); and Toyopearl™ ether, hexyl, phenyl or butyl (TosoHaas, PA). In one embodiment, the hydrophobic resin is a butyl hydrophobic resin. In another embodiment, the hydrophobic resin is a phenyl hydrophobic resin. In another embodiment, the hydrophobic resin is a hexyl hydrophobic resin, an octyl hydrophobic resin, or a decyl hydrophobic resin. In one embodiment, the hydrophobic resin is a methacrylic polymer having n-butyl ligands (e.g. TOYOPEARL" Butyl-600M).

Further methods for purifying ADC mixtures to obtain a composition having a desired DAR are described in U.S. application Ser. No. 14/210,602 (U.S. Patent Appln. Publication No. US 2014/0286968), incorporated by reference in its entirety.

V. Uses of Anti-EGFR Antibodies and Anti-EGFR ADCs

The antibodies and antibody portions (and ADCs) of the invention preferably are capable of neutralizing human EGFR activity both in vivo. Accordingly, such antibodies and antibody portions of the invention can be used to inhibit hEGFR activity, e.g., in a cell culture containing hEGFR, in human subjects or in other mammalian subjects having EGFR with which an antibody of the invention cross-reacts. In one embodiment, the invention provides a method for inhibiting hEGFR activity comprising contacting hEGFR with an antibody or antibody portion of the invention such that hEGFR activity is inhibited. For example, in a cell culture containing, or suspected of containing hEGFR, an antibody or antibody portion of the invention can be added to the culture medium to inhibit hEGFR activity in the culture.

In another embodiment, of the invention a method for reducing hEGFR activity in a subject, advantageously from a subject suffering from a disease or disorder in which EGFR activity is detrimental. The invention provides methods for reducing EGFR activity in a subject suffering from such a disease or disorder, which method comprises administering to the subject an antibody or antibody portion of the invention such that EGFR activity in the subject is reduced. Preferably, the EGFR is human EGFR, and the subject is a human subject. Alternatively, the subject can be a mammal expressing a EGFR to which antibodies of the invention are capable of binding. Still further the subject can be a mammal into which EGFR has been introduced (e.g., by administration of EGFR or by expression of a EGFR transgene). Antibodies of the invention can be administered to a human subject for therapeutic purposes. Moreover, antibodies of the invention can be administered to a non-human mammal expressing a EGFR with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which EGFR activity is detrimental" is intended to include diseases and other disorders in which the presence of EGFR in a subject suffering from the disorder has been shown to be or is suspected of being either responsible for the pathophysiology of the disorder or a factor that contributes to a worsening of the disorder. Accordingly, a disorder in which EGFR activity is detrimental is a disorder in which reduction of EGFR activity is expected to alleviate the symptoms and/or progression of the disorder. Such disorders may be evidenced, for example, by an increase in the concentration of EGFR in a biological fluid of a subject suffering from the disorder (e.g., an increase in the concentration of EGFR in a tumor, serum, plasma, synovial fluid, etc. of the subject), which can be detected, for example, using an anti-EGFR antibody as described above. Non-limiting examples of disorders that can be treated with the antibodies of the invention, for example, AbA, or antigen binding fragments thereof, include those disorders discussed below. For example, suitable disorders include, but are not limited to, a variety of cancers including, but not limited to, breast cancer, lung cancer, a glioma, prostate cancer, pancreatic cancer, colon cancer, head and neck cancer, and kidney cancer. Other examples of cancer that may be treated using the compositions and methods disclosed herein include squamous cell carcinoma (e.g., squamous lung cancer or squamous head and neck cancer), triple negative breast cancer, non-small cell lung cancer. colorectal cancer, and mesothelioma. In one embodiment, the antibodies and ADCs disclosed herein are used to treat a solid tumor, e.g., inhibit growth of or decrease size of a solid tumor, overexpressing EGFR or which is EGFR positive. In one embodiment, the invention is directed to the treatment of EGFR amplified squamous lung cancer. In one embodiment, the antibodies and ADCs disclosed herein are used to treat EGFR amplified squamous head and neck cancer. In another embodiment, the antibodies and ADCs disclosed herein are used to treat triple negative breast cancer (TNBC). Diseases and disorders described herein may be treated by anti-EGFR antibodies or ADCs of the invention, as well as pharmaceutical compositions comprising such anti-EGFR antibodies or ADCs.

In certain embodiments, the antibodies and ADCs disclosed herein are administered to a subject in need thereof in order to treat advanced solid tumor types likely to exhibit elevated levels of Epidermal Growth Factor Receptor (EGFR). Examples of such tumors include, but are not limited to, head and neck squamous cell carcinoma, non-small cell lung cancer, triple negative breast cancer, colorectal carcinoma, and glioblastoma multiforme.

In certain embodiments, the invention includes a method for inhibiting or decreasing solid tumor growth in a subject having a solid tumor, said method comprising administering an anti-EGFR antibody or ADC described herein, to the subject having the solid tumor, such that the solid tumor growth is inhibited or decreased. In certain embodiments, the solid tumor is a non-small cell lung carcinoma or a glioblastoma. In further embodiments, the solid tumor is an EGFRvIII positive tumor or an EGFR-expressing solid tumors. In further embodiments, the solid tumor is an EGFR amplified solid tumor or an EGFR overexpressing solid tumors. In certain embodiments the anti-EGFR antibodies or ADCs described herein are are administered to a subject having glioblastima multiforme, alone or in combination with an additional agent, e.g., radiation and/or temozolomide.

In certain embodiments, the invention includes a method for inhibiting or decreasing solid tumor growth in a subject having a solid tumor which was identified as an EGFR expressing or EGFR overexpressing tumor (or an EGFRvIII expressing tumor), said method comprising administering an anti-EGFR antibody or ADC described herein, to the subject having the solid tumor, such that the solid tumor growth is inhibited or decreased. Methods for identifying EGFR expressing tumors (e.g., EGFR overexpressing tumors) are known in the art, and include FDA-approved tests and validation assays. For example, the EGFR pharmDx™ assay (Dako North America, Inc.) is a qualitative immunohistochemical (IHC) kit system used to identify EGFR expression in normal and neoplastic tissues routinely-fixed for histological evaluation. EGFR pharmDx specifically detects the EGFR (HER1) protein in EGFR-expressing cells. In addition, PCR-based assays may also be used for identifying EGFR overexpressing tumors. For example, these assays may use primers that are specific for the variant EGFR gene (e.g., SEQ ID NO: 33) and/or cDNA and result in the amplification of the EGFR gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

Any of the methods for gene therapy available in the art can be used according to the invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, *Science* 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley & Sons, N Y (1993); and Kriegler, Gene Transfer and Expression, A Laboratory Manual, Stockton Press, NY (1990). Detailed description of various methods of gene therapy is provided in US20050042664 A1 which is incorporated herein by reference.

In another aspect, this application features a method of treating (e.g., curing, suppressing, ameliorating, delaying or preventing the onset of, or preventing recurrence or relapse of) or preventing a EGFR-associated disorder, in a subject. The method includes: administering to the subject an EGFR binding agent (particularly an antagonist), e.g., an anti-EGFR antibody or fragment thereof as described herein, in an amount sufficient to treat or prevent the EGFR-associated disorder. The EGFR antagonist, e.g., the anti-EGFR antibody or fragment thereof, can be administered to the subject, alone or in combination with other therapeutic modalities as described herein.

Antibodies or ADCs of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the invention. The additional agent also can be an agent that imparts a beneficial attribute to the therapeutic composition, e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the invention and at least one additional agent selected from the lists below. The combination can also include more than one additional agent, e.g., two or three additional agents if the combination is such that the formed composition can perform its intended function.

The combination therapy can include one or more EGFR antagonists, e.g., anti-EGFR antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-EGFR binding proteins described herein, for example, anti-EGFR antibodies, are used in combination with an anti-cancer agent or an antineoplastic agent. The terms "anti-cancer agent" and "antineoplastic agent" refer to drugs used to treat malignancies, such as cancerous growths. Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone. Anti-cancer agents that may be used in conjunction with the anti-EGFR antibodies or ADCs of the invention include, among others, the following agents:

| Anti-Cancer Agent | Comments | Examples |
|---|---|---|
| Antibodies<br>(a) antibodies other than anti-EGFR antibodies; and<br>(b) anti-EGFR antibodies which bind different epitopes | Antibodies which bind IGF-1R (insulin-like growth factor type 1 receptor), which is expressed on the cell surface of most human cancers | A12 (fully humanized mAb)<br>19D12 (fully humanized mAb)<br>Cp751-871 (fully humanized mAb)<br>H7C10 (humanized mAb)<br>alphaIR3 (mouse)<br>ScFV/FC (mouse/human chimera)<br>EM/164 (mouse) |
| | Antibodies which bind EGFR (epiderman growth factor receptor); Mutations affecting EGFR expression or activity could result in cancer | Matuzumab (EMD72000)<br>Erbitux ®/Cetuximab (Imclone)<br>Vectibix ®/Panitumumab (Amgen)<br>mAb 806<br>Nimotuxumab (TheraCIM) |
| | Antibodies which bind cMET (Mesechymal epithelial transition factor); a member of the MET family of receptor tyrosine kinases) | AVEO (AV299) (AVEO)<br>AMG102 (Amgen)<br>5D5 (OA-5d5) (Genentech)<br>H244G11 (Pierre Fabre) |
| | Anti-ErbB3 antibodies which bind different epitopes | Ab #14 (MM 121-14)<br>Herceptin ® (Trastuzumab; Genentech)<br>1B4C3; 2D1D12 (U3 Pharma AG) |
| Small Molecules Targeting IGF1R | Insulin-like growth factor type 1 receptor which is expressed on the cell surface of many human cancers | NVP-AEW541-A<br>BMS-536,924 (1H-benzoimidazol-2-yl)-1H-pyridin-2-one)<br>BMS-554,417<br>Cycloligan<br>TAE226<br>PQ401 |
| Small Molecules Targeting EGFR | EGFR (epidermal growth factor receptor); Overexpression or mutations affecting EGFR expression or activity could result in cancer | Iressa ®/Gefitinib (AstraZeneca)<br>CI-1033 (PD 183805) (Pfizer)<br>Lapatinib (GW-572016) (GlaxoSmithKline)<br>Tykerb ®/Lapatinib Ditosylate (Smith Kline Beecham)<br>Tarceva ®/Erlotinib HCL (OSI-774) (OSI Pharma)<br>PKI-166 (Novartis)<br>PD-158780<br>EKB-569<br>Tyrphostin AG 1478 (4-(3-Chloroanillino)-6,7-dimethoxyquinazoline) |
| Small Molecules Targeting cMET | cMET (Mesenchymal epithelial transition factor); a member of the MET family of receptor tyrosine kinases) | PHA665752<br>ARQ 197 |
| Antimetabolites | | Flourouracil (5-FU)<br>Capecitabine/XELODA ® (HLR Roche)<br>5-Trifluoromethyl-2'-deoxyuridine<br>Methotrexate sodium (Trexall) (Barr)<br>Raltitrexed/Tomudex ® (AstraZeneca)<br>Pemetrexed/Alimta ® (Lilly)<br>Tegafur<br>Cytosine Arabinoside (Cytarabine, Ara-C)/<br>Thioguanine ® (GlaxoSmithKline)<br>5-azacytidine<br>6-mercaptopurine (Mercaptopurine, 6-MP)<br>Azathioprine/Azasan ® (AAIPHARMA LLC)<br>6-thioguanine (6-TG)/Purinethol ® (TEVA)<br>Pentostatin/Nipent ® (Hospira Inc.)<br>Fludarabine phosphate/Fludara ® (Bayer Health Care)<br>Cladribine (2-CdA, 2-chlorodeoxyadenosine)/<br>Leustatin ® (Ortho Biotech) |

| Anti-Cancer Agent | Comments | Examples |
|---|---|---|
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumors. | Ribonucleotide Reductase Inhibitor (RNR) Cyclophosphamide/Cytoxan (BMS) Neosar (TEVA) Ifosfamide/Mitoxana ® (ASTA Medica) Thiotepa (Bedford, Abraxis, Teva) BCNU→ 1,3-bis(2-chloroethyl)-1-nitosourea CCNU→ 1,-(2-chloroethyl)-3-cyclohexyl-1-nitrosourea (methyl CCNU) Hexamethylmelamine (Altretamine, HMM)/ Hexalen ® (MGI Pharma Inc.) Busulfan/Myleran (GlaxoSmithKline) Procarbazine HCL/ Matulane (Sigma Tau Pharmaceuticals, Inc.) Dacarbazine (DTIC) Chlorambucil/Leukara ® (SmithKline Beecham) Melphalan/Alkeran ® (GlaxoSmithKline) Cisplatin (Cisplatinum, CDDP)/Platinol (Bristol Myers) Carboplatin/Paraplatin (BMS) Oxaliplatin/Eloxitan ® (Sanofi-Aventis US) |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | Doxorubicin HCL/Doxil ® (Alza) Daunorubicin citrate/Daunoxome ® (Gilead) Mitoxantrone HCL/Novantrone (EMD Serono) Actinomycin D Etoposide/Vepesid ® (BMS)/Etopophos ® (Hospira, Bedford, Teva Parenteral, Etc.) Topotecan HCL/Hycamtin ® (GlaxoSmithKline) Teniposide (VM-26)/Vumon ® (BMS) Irinotecan HCL(CPT-ll)/Camptosar ® (Pharmacia & Upjohn) |
| Microtubule targeting agents | Microtubules are one of the components of the cytoskeleton. They have diameter of ~24 nm and length varying from several micrometers to possibly millimeters in axons of nerve cells. Microtubules serve as structural components within cells and are involved in many cellular processes including mitosis, cytokinesis, and vesicular transport. | Vincristine/Oncovin ® (Lilly) Vinblastine sulfate/Velban ® (discontinued) (Lilly) Vinorelbine tartrate/Navelbine ® (PierreFabre) Vindesine sulphate/Eldisine ® (Lilly) Paclitaxel/Taxol ® (BMS) Docetaxel/Taxotere ® (Sanofi Aventis US) Nanoparticle paclitaxel (ABI-007)/Abraxane ® (Abraxis BioScience, Inc.) Ixabepilone/IXEMPRA ™ (BMS) |
| Kinase inhibitors | Tyrosine kinases are enzymes within the cell that function to attach phosphate groups to the amino acid tyrosine. By blocking the ability of protein tyrosine kinases to function, these compounds provide a tool for controlling cancerous cell growth. | Imatinib mesylate/Gleevec (Novartis) Sunitinib malate/Sutent ® (Pfizer) Sorafenib toslate/Nexavar ® (Bayer) Nilotinib hydrochloride monohydrate/Tasigna ® (Novartis) |
| Protein synthesis inhibitors | Induces cell apoptosis | L-asparaginase/Elspar ® (Merck & Co.) |
| Immunotherapeutic agents | Induces cancer patients to exhibit immune responsiveness | Alpha interferon Angiogenesis Inhibitor/Avastin ® (Genentech) IL-2→ Interleukin 2 (Aldesleukin)/Proleukin ® (Chiron) IL-12→ Interleukin 12 |
| | Antibody/small molecule immune checkpoint modulators | Anti-CTLA-4 and PR-1 therapies Yervoy ® (ipilimumab; Bristol-Myers Squibb) Opdivo ® (nivolumab; Bristol-Myers Squibb) Keytrada ® (pembrolizumab; Merck) |

| Anti-Cancer Agent | Comments | Examples |
| --- | --- | --- |
| Hormones | Hormone therapies associated with menopause and aging seek to increase the amount of certain hormones in your body to compensate for age- or disease-related hormonal declines. Hormone therapy as a cancer treatment either reduces the level of specific hormones or alters the cancer's ability to use these hormones to grow and spread. | Toremifene citrate/Fareston ® (GTX, Inc.) Fulvestrant/Faslodex ® (AstraZeneca) Raloxifene HCL/Evista ® (Lilly) Anastrazole/Arimidex ® (AstraZeneca) Letrozole/Femara ® (Novartis) Fadrozole (CGS 16949A) Exemestane/Aromasin ® (Pharmacia & Upjohn) Leuprolide acetate/Eligard ® (QTL USA) Lupron ® (TAP Pharm) Goserelin acetate/Zoladex ® (AstraZeneca) Triptorelin pamoate/Trelstar ® (Watson Labs) Buserelin/Suprefact ® (Sanofi Aventis) Nafarelin/Synarel ® (Pfizer) Cetrorelix/Cetrotide ® (EMD Serono) Bicalutamide/Casodex ® (AstraZeneca) Nilutamide/Nilandron ® (Aventis Pharm.) Megestrol acetate/Megace ® (BMS) Somatostatin Analogs (Octreotide acetate/ Sandostatin ® (Novartis) |
| Glucocorticoids | Anti-inflammatory drugs used to reduce swelling that causes cancer pain. | Predinsolone Dexamethasone/Decadron ® (Wyeth) |
| Aromatose inhibitors | Includes imidazoles | Ketoconazole |
| mTOR inhibitors | the mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase(PI-3K) to cell growth, proliferation, and angiogenesis. | Sirolimus (Rapamycin)/Rapamune ® (Wyeth) Temsirolimus (CCI-779)/Torisel ® (Wyeth) Deforolimus (AP23573)/(Ariad Pharm.) Everolimus (RAD00I)/Certican ® (Novartis) |

In addition to the above anti-cancer agents, the anti-EGFR antibodies and ADCs described herein may be administered in combination with the agents described in section II. Further, the aforementioned anti-cancer agents may also be used in the ADCs of the invention.

In particular embodiments, the anti-EGFR antibodies or ADCs can be administered alone or with another anti-cancer agent which acts in conjunction with or synergistically with the antibody to treat the disease associated with EGFR activity. Such anti-cancer agents include, for example, agents well known in the art (e.g., cytotoxins, chemotherapeutic agents, small molecules and radiation). Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof of the invention.

In particular embodiments of the invention, the anti-EGFR antibodies or ADCs described herein can be used in a combination therapy with an apoptotic agent, such as a bcl-xl inhibitor or a Bcl-2 (B-cell lymphoma 2) inhibitor (e.g., ABT-199 (venetoclax)) to treat cancer, such as leukemia, in a subject. In one embodiment, the anti-EGFR antibodies or ADCs described herein can be used in a combination therapy with a bcl-xl inhibitor for treating cancer. In one embodiment, the anti-EGFR antibodies or ADCs described herein can be used in a combination therapy with venetoclax for treating cancer.

In particular embodiments of the invention, the anti-EGFR antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment of the invention, anti-EGFR antibodies and ADCs described herein are administered in combination with a NAMPT inhibitor for the treatment of cancer in a subject.

In particular embodiments of the invention, the anti-EGFR antibodies or ADCs described herein can be used in a combination therapy with SN-38, which is the active metabolite of the topoisomerase inhibitor irinotecan.

In other embodiments of the invention, the anti-EGFR antibodies or ADCs described herein can be used in a combination therapy with a PARP (poly ADP ribose polymerase) inhibitor, e.g., veliparib, to treat cancer, including breast, ovarian and non-small cell lung cancers.

Further examples of additional therapeutic agents that can be co-administered and/or formulated with anti-EGFR antibodies or anti-EGFR ADCs described herein, include, but are not limited to, one or more of: inhaled steroids; beta-agonists, e.g., short-acting or long-acting beta-agonists; antagonists of leukotrienes or leukotriene receptors; combination drugs such as ADVAIR; IgE inhibitors, e.g., anti-IgE antibodies (e.g., XOLAIR®, omalizumab); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat, for example, asthma and other respiratory disorders. Other examples of additional therapeutic agents that can be co-administered and/or formulated with anti-EGFR antibodies or anti-EGFR ADCs described herein, include, but are not limited to, one or more of, temozolomide, ibrutinib, duvelisib, and idelalisib. Additional examples of therapeutic agents that can be co-administered and/or formulated with one or more anti-EGFR antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA, CTLA-4, PD-1, or their ligands including CD154 (gp39 or CD40L).

Preferred combinations of therapeutic agents may interfere at different points in the inflammatory cascade; preferred examples include TNF antagonists like chimeric, humanized or human TNF antibodies, adalimumab, (HUMIRA; D2E7; PCT Publication No. WO 97/29131 and U.S. Pat. No. 6,090,382, incorporated by reference herein), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-IRA etc.) may be effective for the same reason. Other preferred combinations include Interleukin 4.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion of the invention is 0.1-20 mg/kg, more preferably 1-10 mg/kg. In one embodiment, the dose of the antibodies and ADCs described herein is 1 to 6 mg/kg, including the individual doses recited therein, e.g., 1 mg/kg, 2 mg/kg, 3 mg/kg, 4 mg/kg, 5 mg/kg, and 6 mg/kg. In another embodiment, the dose of the antibodies and ADCs described herein is 1 to 200 µg/kg, including the individual doses recited therein, e.g., 1 µg/kg, 2 µg/kg, 3 µg/kg, 4 µg/kg, 5 µg/kg, 10 µg/kg, 20 µg/kg, 30 µg/kg, 40 µg/kg, 50 µg/kg, 60 µg/kg, 80 µg/kg, 100 µg/kg, 120 µg/kg, 140 µg/kg, 160 µg/kg, 180 µg/kg and 200 µg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In one embodiment, an anti-EGFR antibody described herein, e.g., AbA, or an antigen binding portion thereof, is administered to a subject in need thereof, e.g., a subject having cancer, as an ADC at a dose of 0.1 to 30 mg/kg. In another embodiment, the anti-EGFR antibody, e.g., AbA, or an antigen binding portion thereof, is administered to a subject in need thereof, e.g., a subject having cancer, as an ADC at a dose of 1 to 15 mg/kg. In another embodiment, the anti-EGFR antibody, e.g., AbA, or an antigen binding portion thereof, is administered to a subject in need thereof, e.g., a subject having cancer, as an ADC at a dose of 1 to 10 mg/kg. In another embodiment, the anti-EGFR antibody, e.g., AbA, or an antigen binding portion thereof, is administered to a subject in need thereof, e.g., a subject having cancer, as an ADC at a dose of 2 to 3. In another embodiment, the anti-EGFR antibody, e.g., AbA, or an antigen binding portion thereof, is administered to a subject in need thereof, e.g., a subject having cancer, as an ADC at a dose of 1 to 4 mg/kg.

In one embodiment, an anti-EGFR antibody described herein, e.g., AbA, or an antigen binding portion thereof, is administered to a subject in need thereof, e.g., a subject having cancer, as an ADC at a dose of 1 to 200 µg/kg. In another embodiment, the anti-EGFR antibody, e.g., AbA, or an antigen binding portion thereof, is administered to a subject in need thereof, e.g., a subject having cancer, as an ADC at a dose of 5 to 150 µg/kg. In another embodiment, the anti-EGFR antibody, e.g., AbA, or an antigen binding portion thereof, is administered to a subject in need thereof, e.g., a subject having cancer, as an ADC at a dose of 5 to 100 µg/kg. In another embodiment, the anti-EGFR antibody, e.g., AbA, or an antigen binding portion thereof, is administered to a subject in need thereof, e.g., a subject having cancer, as an ADC at a dose of 5 to 90 µg/kg. In another embodiment, the anti-EGFR antibody, e.g., AbA, or an antigen binding portion thereof, is administered to a subject in need thereof, e.g., a subject having cancer, as an ADC at a dose of 5 to 80 µg/kg. In another embodiment, the anti-EGFR antibody, e.g., AbA, or an antigen binding portion thereof, is administered to a subject in need thereof, e.g., a subject having cancer, as an ADC at a dose of 5 to 70 µg/kg. In another embodiment, the anti-EGFR antibody, e.g., AbA, or an antigen binding portion thereof, is administered to a subject in need thereof, e.g., a subject having cancer, as an ADC at a dose of 5 to 60 µg/kg. In another embodiment, the anti-EGFR antibody, e.g., AbA, or an antigen binding portion thereof, is administered to a subject in need thereof, e.g., a subject having cancer, as an ADC at a dose of 10 to 80 µg/kg.

In one embodiment, an anti-EGFR ADC described herein, e.g., AbA-vc-MMAE, is administered to a subject in need thereof, e.g., a subject having cancer, at a dose of 0.1 to 6 mg/kg. In another embodiment, an anti-EGFR ADC described herein, e.g., AbA-vc-MMAE, is administered to a subject in need thereof, e.g., a subject having cancer, at a dose of 0.5 to 4 mg/kg. In another embodiment, an anti-EGFR ADC described herein, e.g., AbA-vc-MMAE, is administered to a subject in need thereof, e.g., a subject having cancer, at a dose of 1.8 to 2.4 mg/kg. In another embodiment, an anti-EGFR ADC described herein, e.g., AbA-vc-MMAE, is administered to a subject in need thereof, e.g., a subject having cancer, at a dose of 1 to 4 mg/kg. In another embodiment, an anti-EGFR ADC described herein, e.g., AbA-vc-MMAE, is administered to a subject in need thereof, e.g., a subject having cancer, at a dose of about 1 mg/kg. In another embodiment, an anti-EGFR ADC described herein, e.g., AbA-vc-MMAE, is administered to a subject in need thereof, e.g., a subject having cancer, at a dose of 3 to 6 mg/kg. In another embodiment, an anti-EGFR ADC described herein, e.g., AbA-vc-MMAE, is administered to a subject in need thereof, e.g., a subject having cancer, at a dose of 3 mg/kg. In another embodiment, an anti-EGFR ADC described herein, e.g., AbA-vc-MMAE, is administered to a subject in need thereof, e.g., a subject having cancer, at a dose of 2 to 3 mg/kg. In another embodiment, an anti-EGFR ADC described herein, e.g., AbA-vc-MMAE, is administered to a subject in need thereof, e.g., a subject having cancer, at a dose of 6 mg/kg.

In another embodiment, an anti-EGFR antibody described herein, conjugated to a drug, e.g., a PBD, (an ADC) is administered to a subject in need thereof, e.g., a subject having cancer, at a dose of 1 to 200 µg/kg. In another embodiment, an anti-EGFR ADC described herein, is administered to a subject in need thereof, e.g., a subject having cancer, at a dose of 5 to 100 µg/kg. In another embodiment, an anti-EGFR ADC described herein, is administered to a subject in need thereof, e.g., a subject having cancer, at a dose of 5 to 90 µg/kg. In another embodiment, an anti-EGFR ADC described herein, is administered to a subject in need thereof, e.g., a subject having cancer, at a dose of 5 to 80 µg/kg. In another embodiment, an anti-EGFR ADC described herein, is administered to a subject in need thereof, e.g., a subject having cancer, at a dose of 5 to 70 µg/kg. In another embodiment, an anti-EGFR ADC described herein, is administered to a subject in need thereof, e.g., a subject having cancer, at a dose of 5 to 60 µg/kg.

Doses described above may be useful for the administration of either anti-EGFR ADCs or antibodies disclosed herein.

In another aspect, this application provides a method for detecting the presence of EGFR in a sample in vitro (e.g., a biological sample, such as serum, plasma, tissue, biopsy). The subject method can be used to diagnose a disorder, e.g., a cancer. The method includes: (i) contacting the sample or a control sample with the anti-EGFR antibody or fragment thereof as described herein; and (ii) detecting formation of a complex between the anti-EGFR antibody or fragment thereof, and the sample or the control sample, wherein a statistically significant change in the formation of the complex in the sample relative to the control sample is indicative of the presence of EGFR in the sample.

Given their ability to bind to human EGFR, the anti-human EGFR antibodies, or portions thereof, of the invention, (as well as ADCs thereof) can be used to detect human EGFR (e.g., in a biological sample, such as serum or plasma), using a conventional immunoassay, such as an enzyme linked immunosorbent assays (ELISA), an radioimmunoassay (RIA) or tissue immunohistochemistry. In one aspect, the invention provides a method for detecting human EGFR in a biological sample comprising contacting a biological sample with an antibody, or antibody portion, of the invention and detecting either the antibody (or antibody portion) bound to human EGFR or unbound antibody (or antibody portion), to thereby detect human EGFR in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Alternative to labeling the antibody, human EGFR can be assayed in biological fluids by a competition immunoassay utilizing rhEGFR standards labeled with a detectable substance and an unlabeled anti-human EGFR antibody. In this assay, the biological sample, the labeled rhEGFR standards and the anti-human EGFR antibody are combined and the amount of labeled rhEGFR standard bound to the unlabeled antibody is determined. The amount of human EGFR in the biological sample is inversely proportional to the amount of labeled rhEGFR standard bound to the anti-EGFR antibody. Similarly, human EGFR can also be assayed in biological fluids by a competition immunoassay utilizing rhEGFR standards labeled with a detectable substance and an unlabeled anti-human EGFR antibody.

In yet another aspect, this application provides a method for detecting the presence of EGFR in vivo (e.g., in vivo imaging in a subject). The subject method can be used to diagnose a disorder, e.g., a EGFR-associated disorder. The method includes: (i) administering the anti-EGFR antibody or fragment thereof as described herein to a subject or a control subject under conditions that allow binding of the antibody or fragment to EGFR; and (ii) detecting formation of a complex between the antibody or fragment and EGFR, wherein a statistically significant change in the formation of the complex in the subject relative to the control subject is indicative of the presence of EGFR.

VI. Pharmaceutical Compositions

The invention also provides pharmaceutical compositions comprising an antibody, or antigen binding portion thereof, or ADC of the invention and a pharmaceutically acceptable carrier. The pharmaceutical compositions comprising antibodies or ADCs of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies or ADCs of the invention and one or more prophylactic or therapeutic agents other than antibodies or ADCs of the invention for treating a disorder in which EGFR activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

In one embodiment, the invention features a lyophilized formulation comprising an anti-EGFR antibody drug conjugate, sucrose, polysorbate 80, and histidine, wherein the formulation has a pH of about 5-7, wherein the anti-EGFR antibody drug conjugate comprises an anti-EGFR antibody, or antigen binding portion thereof, conjugated to monomethylauristatin E (MMAE). In one embodiment, the invention further provides a lyophilized formulation comprising an anti-EGFR ADC comprising an anti-EGFR antibody, or antigen-binding portion thereof, as described herein, conjugated to an auristatin, e.g., MMAE, a sugar, e.g., sucrose, a surfactant, e.g., a polysorbate, such as polysorbate 80, and histidine. In one embodiment, the lyophilized formulation comprises 1-20 mg of histidine, about 320-410 mg of a sugar, about 0.1 to 0.9 mg of a surfactant, and about 1-150 mg of an anti-EGFR ADC comprising an anti-EGFR antibody, or antigen-binding portion thereof, as described herein, conjugated to an auristatin, e.g., MMAE. The invention also provides an aqueous formulation comprising about 1-100 mg/ml of an anti-EGFR ADC comprising an anti-EGFR antibody, or antigen-binding portion thereof, as described herein, conjugated to an auristatin, e.g., MMAE, about 1-10 mg/mL histidine, about 50-90 mg/ml of a sugar, e.g., sucrose, and about 0.01-0.2 mg/ml of a surfactant, e.g., polysorbate 80.

Various delivery systems are known and can be used to administer one or more antibodies or ADCs of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985, 309, 5,934, 272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397, Cleek et al., 1997, "Biodegradable Polymeric Carriers for a bFGF Antibody for Cardiovascular Application," *Pro. Int'l. Symp. Control. Rel. Bioact. Mater.* 24:853-854, and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the invention comprises intranasal administration of a composition, the composition can be formulated in an aerosol form, spray, mist or in the form of drops. In particular, prophylactic or therapeutic agents for use according to the invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p- hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985, 320, 5, 985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions or ADCs of the invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion or ADC of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In other embodiments, an antibody or antibody portion or ADC of the invention may be conjugated to a polymer-based species such that said polymer-based species may confer a sufficient size upon said antibody or antibody portion of the invention such that said antibody or antibody portion of the invention benefits from the enhanced permeability and retension effect (EPR effect) (See also PCT Publication No. WO2006/042146A2 and U.S. Publication Nos. 2004/0028687A1, 2009/0285757A1, and 2011/0217363A1, and U.S. Pat. No. 7,695,719 (each of which is incorporated by reference herein in its entirety and for all purposes).

Supplementary active compounds can also be incorporated into the compositions. In certain embodiments, an antibody or antibody portion or ADC of the invention is formulated with and/or co-administered with one or more additional therapeutic agents that are useful for treating disorders in which EGFR activity is detrimental. For example, an anti-hEGFR antibody or antibody portion or ADC of the invention may be formulated and/or co-administered with one or more additional antibodies that bind other targets (e.g., antibodies that bind cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody or ADC to EGFR or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting

EXAMPLES

Example 1: Identification of Improved Anti-EGFR Antibodies

Antibody 1

Antibody 1 (Ab1) is a humanized anti-EGFR antibody. The heavy chain variable region (VH) amino acid sequence of Ab1 is provided below as SEQ ID NO: 1. The VH CDR amino acid sequences of Ab1 are underlined below and are as follows: GYSISSDFAWN (VH CDR1; SEQ ID NO: 2); YISYSGNTRYQPSLKS (VH CDR2; SEQ ID NO: 3); and AGRGFPY (VH CDR3; SEQ ID NO: 4).

Ab1 VH sequence (SEQ ID NO: 1)
QVQLQESGPGLVKPSQTLSLTCTVS<u>GYSISSDFAWN</u>WIRQPPGKGLEWMG <u>YISYSGNTRYQPSLKS</u>RITISRDTSKNQFFLKLNSVTAADTATYYCVTA<u>G</u>

<u>RGFPYWGQGTLVTVSS</u>

The light chain variable region (VL) amino acid sequence of Ab1 is provided below as SEQ ID NO 5. The VL CDR amino acid sequences of Ab1 are underlined below and are as follows: HSSQDINSNIG (VL CDR1; SEQ ID NO: 6); HGTNLDD (VL CDR2; SEQ ID NO: 7); and VQYAQF-PWT (VL CDR3; SEQ ID NO: 8).

Ab1 VL sequence (SEQ ID NO: 5)
DIQMTQSPSSMSVSVGDRVTITC<u>HSSQDINSNIG</u>WLQQKPGKSFKGLIY <u>HGTNLDD</u>GVPSRFSGSGSGTDYTLTISSLQPEDFATYYC<u>VQYAQFPWTF</u>

GGGTKLEIK

A screen was performed to identify anti-EGFR antibodies having improved properties over Ab1. The details of the identification of Ab1 variants are provided below.

Preparation of Ab1 variant VL and VH libraries

Ab1 variant antibodies were identified by screening three single chain (scFv) libraries containing variant heavy or light chain variable regions of Ab1. One of the scFv libraries contained Ab1 variant variable heavy chains (i.e., scFvs containing an Ab1 variant variable heavy chain and an Ab1 variable light chain), while the second scFv library contained Ab1 variant variable light chains (i.e., scFvs containing an Ab1 variant variable light chain and an Ab1 variable heavy chain). Ab1 variant VH and VL regions were also combined into a third scFv library which was subsequently screened through multiple rounds to select combinations of VH and VL Ab1 variants having higher binding affinity than Ab1. The design of the Ab1 variant VH and VL libraries is shown in FIG. 16.

To create variant Ab1 VH regions, twelve amino acid residues were selected for mutation based, at least in part, on alignment of the VH of Ab1 with the VH4-4 (SEQ ID NO: 93) and VH4-b germline sequences (see FIG. 16A where mutated amino acid residues are designated "X"). A P101D alteration (designated "Z" in FIG. 16A) was also generated based on human germline and Ab1 sequences. Using the codon usage described above, it was calculated that by targeting twelve residues ("X" residues in FIG. 16A) a $10^9$ library would provide the majority of VH Ab1 variants with four or fewer mutated residues per clone. As described in FIG. 16A, one framework residue (Q1E) was also changed to prevent N-terminal pyroglutamate formation.

To create variant Ab1 VL regions, eleven amino acid residues were selected for mutation based, at least in part, on alignment of the VL region of Ab1 with the IGKV1-12 (L5) germline sequence (see residues marked "X" in FIG. 16B) (IGKV1-12 is described in SEQ ID NO: 94). Residues at positions 33 and 52 (marked "1" and "2", respectively, in FIG. 16B) were designed to have limited diversity. Residues at position 33 were limited to L, V, I, or F, and residues at position 52 were limited to S, A, T, and P.

Yeast libraries based on the foregoing were created using transformation methods described in Benatuil et al. (2010) *Protein Eng. Design, and Selection,* 23 (4): 155-159.

Screening of scFv Ab1 Variant Libraries

Single chain variable fragments (scFvs) containing either the Ab1 variant VH or VL regions were expressed from the respective libraries, and were screened based on the scFv's ability to bind truncated wild type (wt) human EGFR1-525, and mutant EGFR(CA). EGFR (CA) is an EGFR variant that contains cysteine to alanine mutations at positions 295 and 307 (see Garrett et al. (2009) *PNAS USA* 106(13): 5082-5087). Libraries containing about $1 \times 10^9$ clones were screened.

Given that Ab1 binds to EGFR (CA) but does not substantially bind wtEGFR, initial rounds of screening used EGFR (CA) to identify Ab1 variant heavy and light chains having improved binding affinity ($k_{on}$, $k_{off}$, or both rates) for EGFR(CA) relative to Ab1. Later rounds of screening, however, used EGFR(1-525) to identify Ab1 variants having improved binding affinity ($k_{on}$, $k_{off}$, or both rates) over Ab1 for EGFR(1-525).

Library screening was performed using two methods, including magnetic bead sorting (MACS (magnetic cell separation technology)) and a FACS based assay (for MACS and FACS see, e.g., Chao et al (2006) *Nature Protocols* 1:755-765; Feldhaus et al. (2003) *Nature Biotech* 21:163-170; and VanAntwerp (2000) *Biotechnol. Prog.* 16:31-37). At least two rounds of screening based on magnetic bead enrichment was performed followed by at least three rounds of screening based on flow cytometric sorting (Feldhaus and Siegel, Ch. 17 of Flow Cytometry Protocols, $2^{nd}$ ed., ed. Hawley and Hawley, vol. 263). Both equilibrium and $k_{off}$ selection were used to identify scFvs having improved binding over Ab1. In total, three libraries were screened for Ab1 variant VH and VL regions having improved binding over Ab1. Four to five rounds of screening was performed using the Ab1 variant VH and VL libraries, and five to six rounds was performed for the combined Ab1 variant VH/VL library. Screening of the Ab1 variant VL library, the Ab1 variant VH library, and the combined Ab1 variant VH and VL library resulted in the identification of scFvs containing Ab1 variant VH and VL regions having higher binding affinities for EGFR (EGFR(1-525) and EGFR (CA)) over Ab1.

Identification of Improved Antibodies

Fifteen Ab1 variant scFvs identified as having improved binding characteristics, including specific binding to EGFR (1-525), were selected for conversion into IgG proteins (specifically IgG1 antibodies). The fifteen Ab1 variant antibodies are described herein, and include Antibody A (referred to throughout as "AbA") (see VH SEQ ID NO: 9; VL SEQ ID NO: 5), Antibody B (referred to herein as "AbB") (see VH SEQ ID NO: 64; VL SEQ ID NO: 65), Antibody C (referred to herein as "AbC") (see VH SEQ ID NO: 66; VL SEQ ID NO: 67), and Antibody D (referred to herein as "AbD") (see VH SEQ ID NO: 68; VL SEQ ID NO: 69), Antibody E (referred to herein as "AbE") (see VH SEQ ID NO: 50; VL SEQ ID NO: 51), Antibody F (referred to herein as "AbF") (see VH SEQ ID NO: 52; VL SEQ ID NO: 53), Antibody G (referred to herein as "AbG") (see VH SEQ ID NO: 72; VL SEQ ID NO: 73), Antibody H (referred to herein as "AbH") (see VH SEQ ID NO: 54; VL SEQ ID NO: 55), Antibody J (referred to herein as "AbJ") (see VH SEQ ID NO: 56; VL SEQ ID NO: 57), Antibody K (referred to herein as "AbK"), Antibody L (referred to herein as "AbL") (see VH SEQ ID NO: 58; VL SEQ ID NO: 59), Antibody M (referred to herein as "AbM") (see VH SEQ ID NO: 76; VL SEQ ID NO: 77), Antibody N (referred to herein as "AbN") (see VH SEQ ID NO: 60; VL SEQ ID NO: 61), Antibody 0 (referred to herein as "AbO") (see VH SEQ ID NO: 62; VL SEQ ID NO: 63), and Antibody P (referred to herein as "AbP") (see VH SEQ ID NO: 78; VL SEQ ID NO: 79). Selected clones from the VH and VL libraries were paired with the Ab1 VL or VH region, respectively (see AbA, AbB, AbC, AbD, AbE, and AbF).

Amino acid sequences of the VH regions of the Ab1 variant antibodies are provided below. The CDRs are underlined, and the amino acid changes relative to Ab1 are highlighted in bold.

AbA VH
(SEQ ID NO: 9)
EVQLQESGPGLVKPSQTLSLTCTVS<u>GYSISRDFAWN</u>WIRQPPGKGLEWMG <u>YISYNGNTRYQPSLKS</u>RITISRDTSKNQFFLKLNSVTAADTATYYCVT<u>AS RGFPY</u>WGQGTLVTVSS

AbB VH
(SEQ ID NO: 64)
EVQLQESGPGLVKPSQTLSLTCTVS<u>GYSISNDFAWN</u>WIRQPPGKGLEWMG <u>YISYKGNTRYQPSLKS</u>RITISRDTSKNQFFLKLNSVTAADTATYYCVT<u>AS RGFPW</u>WGQGTLVTVSS

AbC VH
(SEQ ID NO: 66)
EVQLQESGPGLVKPSQTLSLTCTVS<u>GYSISSDFAWN</u>WIRQPPGKGLEWMG <u>YISYSGNTRYQPSLKS</u>RITISRDTSKNQFFLKLNSVTAADTATYYCVT<u>AG RGFPY</u>WGQGTLVTVSS

AbD VH
(SEQ ID NO: 68)
EVQLQESGPGLVKPSQTLSLTCTVS<u>GYSISSDFAWN</u>WIRQPPGKGLEWMG <u>YISYSGNTRYQPSLKS</u>RITISRDTSKNQFFLKLNSVTAADTATYYCVT<u>AG RGFPY</u>WGQGTLVTVSS

AbE VH
(SEQ ID NO: 50)
EVQLQESGPGLVKPSQTLSLTCTVS<u>GYSISSDFAWN</u>WIRQPPGKGLEWMG <u>YISYSGNTRYQPSLKS</u>RITISRDTSKNQFFLKLNSVTAADTATYYCVT<u>AG RGFPY</u>WGQGTLVTVSS

AbF VH
(SEQ ID NO: 52)
EVQLQESGPGLVKPSQTLSLTCTVS<u>GYSISRDFAWN</u>WIRQPPGKGLEWMG <u>YISYSGNTRYQPSLKS</u>RITISRDTSKNQFFLKLNSVTAADTATYYCVT<u>AS RGFPY</u>WGQGTLVTVSS

AbG VH
(SEQ ID NO: 72)
EVQLQESGPGLVKPSQTLSLTCTVS<u>GYSISNDFAWN</u>WIRQLPGKGLEWMG <u>YISYKGNTRYQPSLKS</u>RITISRDTSKNQFFLKLNSVTAADTATYYCVT<u>AS RGLPY</u>WGQGTLVTVSS

AbH VH
(SEQ ID NO: 54)
EVQLQESGPGLVKPSQTLSLTCTVS<u>GYSIGKDFAWN</u>WIRQPPGKGLEWMG <u>YISYNGNTRYQPSLKS</u>RITISRDTSKNQFFLKLNSVTAADTATYYCVT<u>AS RGLPY</u>WGQGTLVTVSS

AbJ VH
(SEQ ID NO: 56)
EVQLQESGPGLVKPSQTLSLTCTVS<u>GYSIGKDFAWN</u>WIRQPPGKGLEWMG <u>YISYSGNTRYQPSLKS</u>RITISRDTSKNQFFLKLNSVTAADTATYYCVT<u>AS RGLPY</u>WGQGTLVTVSS

AbK VH
(SEQ ID NO: 74)
EVQLQESGPGLVKPSQTLSLTCTVS<u>GYSISRDFAWN</u>WIRQPPGKGLEWMG <u>YISYNGNTRYQPSLKS</u>RITISRDTSKNQFFLKLNSVTAADTATYYCVT<u>AS RGFPW</u>WGQGTLVTVSS

AbL VH
(SEQ ID NO: 58)
EVQLQESGPGLVKPSQTLSLTCTVS<u>GYSIGKDFAWN</u>WIRQPPGKGLEWMG <u>YISYNGNTRYQPSLKS</u>RITISRDTSKNQFFLKLNSVTAADTATYYCVT<u>AS RGLPY</u>WGQGTLVTVSS

AbM VH
(SEQ ID NO: 76)
EVQLQESGPGLVKPSQTLSLTCTVS<u>GYSIGRDFAWN</u>WIRQPPGKGLEWMG <u>YISYNGNTRYQPSLKS</u>RITISRDTSKNQFFLKLNSVTAADTATYYCVT<u>AS RGFPY</u>WGQGTLVTVSS

AbN VH
(SEQ ID NO: 60)
EVQLQESGPGLVKPSQTLSLTCTVS<u>GYSIGRDFAWN</u>WIRQPPGKGLEWMG <u>YISYSGNTRYQPSLKS</u>RITISRDTSKNQFFLKLNSVTAADTATYYCVT<u>AS RGFPY</u>WGQGTLVTVSS

AbO VH
(SEQ ID NO: 62)
EVQLQESGPGLVKPSQTLSLTCTVS<u>GYSIGKDFAWN</u>WIRQPPGKGLEWMG <u>YISYNGNTRYQPSLKS</u>RITISRDTSKNQFFLKLNSVTAADTATYYCVT<u>AS RGFPY</u>WGQGTLVTVSS

AbQ VH
(SEQ ID NO: 70)
EVQLQESGPGLVKPSQTLSLTCTVS<u>GYSISHDFAWN</u>WIRQPPGKGLEWMG <u>YISYNGNTRYQPSLKS</u>RITISRDTSKNQFFLKLNSVTAADTATYYCVT<u>AS WGLPW</u>WGQGTLVTVSS

AbP VH
(SEQ ID NO: 78)
EVQLQESGPGLVKPSQTLSLTCTVS<u>GYSISHDFAWN</u>WIRQPPGKGLEWMG <u>YISYSGNTRYQPSLKS</u>RITISRDTSKNQFFLKLNSVTAADTATYYCVT<u>AS WGLPW</u>WGQGTLVTVSS

Amino acid sequences of the VL regions of the Ab1 variant antibodies are provided below. The CDRs are underlined, and the amino acid changes relative to Ab1 are highlighted in bold.

AbA VL
(SEQ ID NO: 5)
DIQMTQSPSSMSVSVGDRVTITC<u>HSSQDINSNIG</u>WLQQKPGKSFKGLIY <u>HGTNLDD</u>GVPSRFSGSGSGTDYTLTISSLQPEDFATYYC<u>VQYAQFPWT</u>F GGGTKLEIK

AbB VL
(SEQ ID NO: 65)
DIQMTQSPSSMSVSVGDRVTITC<u>HSSQDINSNIG</u>WLQQKPGKSFKGLIY <u>HGTNLDD</u>GVPSRFSGSGSGTDYTLTISSLQPEDFATYYC<u>VQYAQFPWT</u>F GGGTKLEIK

AbC VL
(SEQ ID NO: 67)
DIQMTQSPSSMSVSVGDRVTITC<u>HSSQDINSNIG</u>WLQQKPGKSFKGLIY <u>HGTNLDD</u>GVPSRFSGSGSGTDYTLTISSLQPEDFATYYC<u>VQYEQFPWT</u>F GGGTKLEIK

-continued

AbD VL
(SEQ ID NO: 69)
DIQMTQSPSSMSVSVGDRVTITC<u>HSSQDINSNL</u>GWLQQKPGKSFKGLIY

<u>HGANLHD</u>GVPSRFSGSGSGTDYTLTISSLQPEDFATYYC<u>VQYAEFPWT</u>F

GGGTKLEIK

AbE VL
(SEQ ID NO: 51)
DIQMTQSPSSMSVSVGDRVTITC<u>HSSQDINSNL</u>GWLQQKPGKSFKGLIY

<u>HGSNLDH</u>GVPSRFSGSGSGTDYTLTISSLQPEDFATYYC<u>VQYDQFPWT</u>F

GGGTKLEIK

AbF VL
(SEQ ID NO: 53)
DIQMTQSPSSMSVSVGDRVTITC<u>HSSQDINSNI</u>GWLQQKPGKSFKGLIY

<u>HGTNLDD</u>GVPSRFSGSGSGTDYTLTISSLQPEDFATYYC<u>VQYAQFPWT</u>F

GGGTKLEIK

AbG VL
(SEQ ID NO: 73)
DIQMTQSPSSMSVSVGDRVTITC<u>HSSQDITYNI</u>GWLQQKPGKSFKGLIY

<u>HGANLDD</u>GVPSRFSGSGSGTDYTLTISSLQPEDFATYYC<u>VQYDEFPWT</u>F

GGGTKLEIK

AbH VL
(SEQ ID NO: 55)
DIQMTQSPSSMSVSVGDRVTITC<u>HSSQDITYNI</u>GWLQQKPGKSFKGLIY

<u>HGANLDD</u>GVPSRFSGSGSGTDYTLTISSLQPEDFATYYC<u>VQYDEFPWT</u>F

GGGTKLEIK

AbJ VL
(SEQ ID NO: 57)
DIQMTQSPSSMSVSVGDRVTITC<u>HSSQDITYNI</u>GWLQQKPGKSFKGLIY

<u>HGANLDD</u>GVPSRFSGSGSGTDYTLTISSLQPEDFATYYC<u>VQYDEFPWT</u>F

GGGTKLEIK

AbK VL
(SEQ ID NO: 75)
DIQMTQSPSSMSVSVGDRVTITC<u>HSSQDITYNV</u>GWLQQKPGKSFKGLIY

<u>HGSNLDH</u>GVPSRFSGSGSGTDYTLTISSLQPEDFATYYC<u>VQYDDFPWT</u>F

GGGTKLEIK

AbL VL
(SEQ ID NO: 59)
DIQMTQSPSSMSVSVGDRVTITC<u>HSSQDITYNV</u>GWLQQKPGKSFKGLIY

<u>HGSNLDH</u>GVPSRFSGSGSGTDYTLTISSLQPEDFATYYC<u>VQYDDFPWT</u>F

GGGTKLEIK

AbM VL
(SEQ ID NO: 77)
DIQMTQSPSSMSVSVGDRVTITC<u>HSSQDITYNV</u>GWLQQKPGKSFKGLIY

<u>HGSNLDH</u>GVPSRFSGSGSGTDYTLTISSLQPEDFATYYC<u>VQYDDFPWT</u>F

GGGTKLEIK

AbN VL
(SEQ ID NO: 61)
DIQMTQSPSSMSVSVGDRVTITC<u>HSSQDITYNV</u>GWLQQKPGKSFKGLIY

<u>HGSNLDH</u>GVPSRFSGSGSGTDYTLTISSLQPEDFATYYC<u>VQYDDFPWT</u>F

GGGTKLEIK

AbO VL
(SEQ ID NO: 63)
DIQMTQSPSSMSVSVGDRVTITC<u>HSSQDITYNV</u>GWLQQKPGKSFKGLIY

<u>HGSNLDH</u>GVPSRFSGSGSGTDYTLTISSLQPEDFATYYC<u>VQYDDFPWT</u>F

GGGTKLEIK

AbQ VL
(SEQ ID NO: 71)
DIQMTQSPSSMSVSVGDRVTITC<u>HSSQDINMNV</u>GWLQQKPGKSFKGLIY

<u>HGAILDD</u>GVPSRFSGSGSGTDYTLTISSLQPEDFATYYC<u>VQYAEFPWT</u>F

GGGTKLEIK

AbP VL
(SEQ ID NO: 79)
DIQMTQSPSSMSVSVGDRVTITC<u>HSSQDINMNV</u>GWLQQKPGKSFKGLIY

<u>HGAILDD</u>GVPSRFSGSGSGTDYTLTISSLQPEDFATYYC<u>VQYAEFPWT</u>F

GGGTKLEIK

Nucleic acid sequences of the fifteen Ab1 variant VH and/or VL domains were subcloned into expression vectors for expression of full length IgG antibodies (see vectors and methods disclosed in U.S. Pat. No. 8,187,836 and U.S. Pat. No. 8,455,219, both incorporated by reference herein). The antibody expression vectors were transiently transfected into HEK293 cells according to standard methods (see Durocher et al. (2002) *Nucleic Acid Res.* 30(2;e9)). The amino acid sequence of the leader sequence used for expression of the heavy chain of each of the Ab1 variants was MEFGLSWL-FLVAILKGVQC (SEQ ID NO: 88), while the amino acid sequence used for the leader sequence for the expression of the light chain of each of the Ab1 variants was MRVPAQLL-GLLLLWFPGSRC (SEQ ID NO: 89). The Ab1 antibody variants were subsequently purified from media by protein A chromatography for affinity and functional assessment.

Antibody AbA

One of the identified Ab1 variant antibodies was AbA. AbA has the same variable light chain sequence as Ab1 (SEQ ID NO: 5), including the same CDR1, CDR2, and CDR3 amino acid sequences (described in SEQ ID NOs: 6, 7, and 8, respectively).

The VH amino acid sequence of AbA is provided below in SEQ ID NO: 9. The VH CDR amino acid sequences of AbA are as follows: GYSISRDFAWN (CDR1; SEQ ID NO: 10); YISYNGNTRYQPSLKS (CDR2; SEQ ID NO: 11); and ASRGFPY (CDR3; SEQ ID NO: 12), and are underlined below. Residues that are different in the heavy chain variable region of AbA versus Ab1 are shown below in bold.

AbA VH amino acid sequence
(SEQ ID NO: 9)
EVQLQESGPGLVKPSQTLSLTCTVS<u>GYSISRDFAWN</u>WIRQPPGKGLEWMG <u>YISYNGNTRYQPSLKS</u>RITISRDTSKNQFFLKLNSVTAADTATYYCVT<u>AS</u>

<u>RGFPY</u>WGQGTLVTVSS

Figures 1, 12:
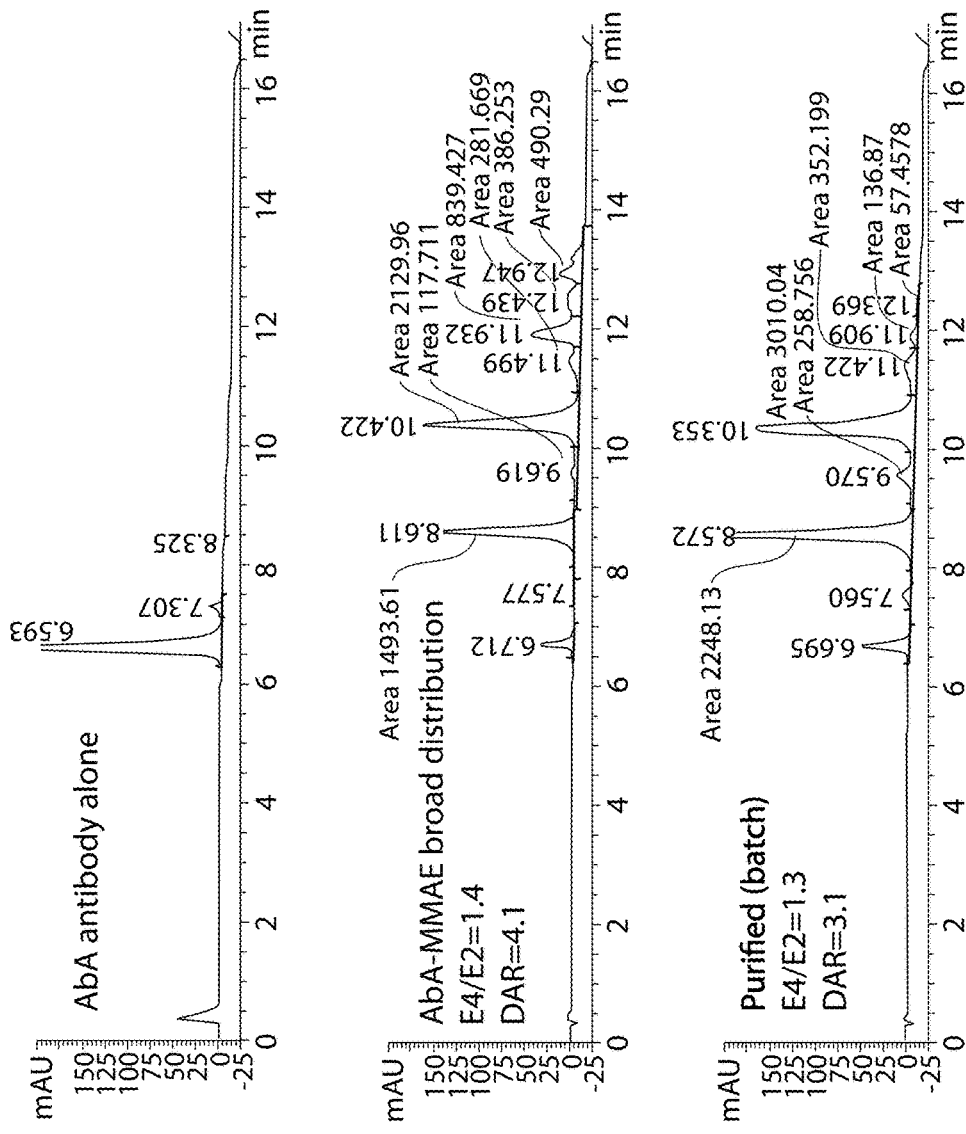
Figures 2, 12:
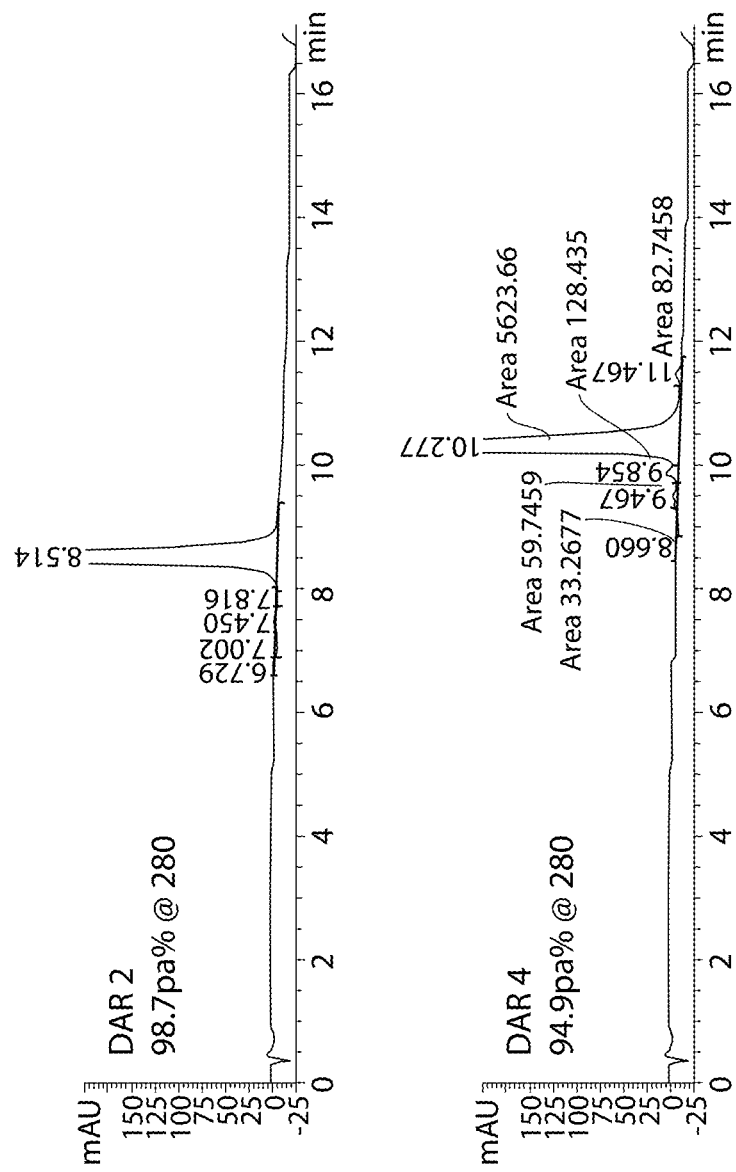

FIGS. 1 and 2 provide an alignment of the amino acid sequences of the VH and VL regions (FIG. 1) and the complete heavy and light chains (FIG. 2) of Ab1 and AbA. The light chain amino acid sequences of Ab1 and AbA are the same (SEQ ID NO: 13). The heavy chain amino acid sequences of Ab1 and AbA, however, have six amino acid differences between the two sequences, three of which are in the CDRs. Differences between the Ab1 VH amino acid sequence and the AbA VH amino acid sequence are shaded in FIG. 1 and are found in each of the VH CDRs. The CDR1 domain of the variable heavy chain of AbA included an amino acid change from a serine (Ab1) to an arginine. The CDR2 domain of the variable heavy chain included an amino acid change from a serine in Ab1 to an asparagine in AbA. Finally, the CDR3 domain of the variable heavy chain included an amino acid change from a glycine in Ab1 to a serine in AbA. Two of the amino acid changes within AbA are in the constant region of the heavy chain (D354E and L356M). The Fc region amino acid mutations in AbA represent human IgG allotype changes from a z, a allotype to a z, non-a allotype. In addition to the other changes, the first amino acid was changed from a glutamine (Q) to a glutamic acid (E), as described, for example, in FIG. 1.

Comparison of Ab1 Variant Antibody Sequences to Ab1 Sequence

Table 1 provides an alignment of the amino acid sequences of the heavy and light chain CDRs for Ab1 variant antibodies AbA, AbG, AbK, AbM, and AbP in comparison to Ab1. Table 2 provides a comparison of the anti-EGFR antibody CDR consensus sequences for Ab1, AbA, AbG, AbK, AbM, and AbP. Blank spaces in Tables 1 and 3 indicate that the residue is the same as Ab1.

TABLE 2

Heavy and Light Chain CDR Sequence Comparison of Ab1 vs. AbA, AbG, AbK, AbM, and AbP Variants TABLE 2-continued CDR Consensus Sequences for Ab1 Variants from Table 1

| CDR region | SEQ ID NO: | CDR Consensus Sequences for Ab1 Variants |
|---|---|---|
| VH CDR3 | SEQ ID NO: 37 | A S(R/W) G (F/L) P (Y/W) |
| VL CDR1 | SEQ ID NO: 38 | H S S Q D I(N/T) (Y/M/S) N(I/V) G |
| VL CDR2 | SEQ ID NO: 39 | H G (T/A/S) (N/I) L D(D/H) |
| VL CDR3 | SEQ ID NO: 40 | V Q Y(A/D) (Q/E/D) F P W T |

TABLE 1

Heavy and Light Chain CDR Sequence Comparison of Ab1 vs. AbA, AbG, AbK, AbM, and AbP Variants

HEAVY CHAIN CDRS

| | Variable Heavy Chain (VH) CDR1 | SEQ ID NO: | VH CDR2 | SEQ ID NO: | VH CDR3 | SEQ ID NO: |
|---|---|---|---|---|---|---|
| Ab1 | G Y S I S S D F A W N | 2 | Y I S Y S G N T R Y Q P S L K S | 3 | A G R G F P Y | 4 |
| AbA |          R | 10 |         N | 11 |   S | 12 |
| AbG |          N | 16 |         K | 17 |   S   L | 18 |
| AbK |          R | 10 |         N | 11 |   S      W | 19 |
| AbM |       G R | 20 |         N | 11 |   S | 12 |
| AbP |          H | 21 | | 3 | S W  L  W | 22 |

LIGHT CHAIN CDRS

| | Variable Light Chain (VL) CDR1 | SEQ ID NO: | VL CDR2 | SEQ ID NO: | VL CDR3 | SEQ ID NO: |
|---|---|---|---|---|---|---|
| Ab1 | H S S Q D I N S N I G | 6 | H G T N L D D | 7 | V Q Y A Q F P W T | 8 |
| AbA | | 6 | | 7 | | 8 |
| AbG |         T Y | 23 |     A | 24 |     D E | 25 |
| AbK |         T Y  V | 26 |     S     H | 27 |     D D | 28 |
| AbM |         T Y  V | 26 |     S     H | 27 |     D D | 28 |
| AbP |          M V | 29 |     A  I | 30 |     E | 31 |

TABLE 2

CDR Consensus Sequences for Ab1 Variants from Table 1

| CDR region | SEQ ID NO: | CDR Consensus Sequences for Ab1 Variants |
|---|---|---|
| VH CDR1 | SEQ ID NO: 35 | G Y S I(S/G/H) (S/R/N) D F A W N |
| VH CDR2 | SEQ ID NO: 36 | Y I S Y(S/N/K) G N T R Y Q P S L K S |

As described in Table 2, the Ab1 variant antibodies AbA, AbG, AbK, AbM, AbP each has a serine residue in the variable heavy chain of CDR3 in place of a glycine (shown in bold/underlined in Table 2).

A comparison of the VH and VL CDR sequences of Ab1 versus antibodies AbB, AbC, AbD, AbE, AbF, AbH, AbJ, AbL, AbN, AbO, and AbQ is described in Table 3. In addition to the CDR changes described in Table 3, AbG has an amino acid residue change within the framework 2 regions of the VH.

TABLE 3

Heavy and Light Chain CDR Sequence Comparison of Ab1 vs. Certain Ab1 Variants

HEAVY CHAIN CDRS

| | Variable Heavy Chain (VH) CDR1 | SEQ ID NO: | VH CDR2 | SEQ ID NO: | VH CDR3 | SEQ ID NO: |
|---|---|---|---|---|---|---|
| Ab1 | G Y S I S S D F A W N | 2 | Y I S Y S G N T R Y Q P S L K S | 3 | A G R G F P Y | 4 |
| AbB |         N           | 16 |         K                       | 17 |     S     W | 19 |
| AbC |                     | 2  |                                 | 3  |             | 4  |
| AbD |                     | 2  |                                 | 3  |             | 4  |
| AbE |                     | 2  |                                 | 3  |             | 4  |
| AbF |       R             | 10 |                                 | 3  |   S         | 12 |
| AbH |     G   K           | 80 |           N                     | 11 |   S   L     | 18 |
| AbJ |     G   K           | 80 |                                 | 3  |   S   L     | 18 |
| AbL |     G   K           | 80 |           N                     | 11 |   S   L     | 18 |
| AbN |     G   R           | 20 |                                 | 3  |   S         | 12 |
| AbO |     G   K           | 80 |           N                     | 11 |   S         | 12 |
| AbQ |         H           | 81 |           N                     | 11 |   S W   L W | 22 |

LIGHT CHAIN CDRS

| | Variable Light Chain (VL) CDR1 | SEQ ID NO: | VL CDR2 | SEQ ID NO: | VL CDR3 | SEQ ID NO: |
|---|---|---|---|---|---|---|
| Ab1 | H S S Q D I N S N I G | 6 | H G T N L D D | 7 | V Q Y A Q F P W T | 8 |
| AbB |                       | 6 |               | 7 |                   | 8 |
| AbC |                       | 6 |               | 7 |     E             | 84 |
| AbD |                 L     | 82 |   A     H   | 83 |     E             | 31 |
| AbE |                 L     | 82 |   S       H | 27 |     D             | 85 |
| AbF |                       | 6 |               | 7 |                   | 8 |
| AbH |         T Y           | 23 |   A         | 24 |     D E           | 25 |
| AbJ |         T Y           | 23 |   A         | 24 |     D E           | 25 |
| AbL |         T Y     V     | 26 |   S       H | 27 |     D D           | 28 |
| AbN |         T Y     V     | 26 |   S       H | 27 |     D D           | 28 |
| AbO |         T Y     V     | 26 |   S       H | 27 |     D D           | 28 |
| AbQ |             M   V     | 29 |   A I       | 30 |     E             | 31 |

Characterization of the Ab1 variant antibodies are described in Examples 2 to 8 below.

Example 2: Binding Analysis of Anti-EGFR Antibodies

Biacore Analysis

Biacore analysis was performed to compare the affinity of Ab1, Ab2 (an antibody having the same six CDR amino acid sequences of cetuximab), and the anti-EGFR antibodies identified in Example 1 to three forms of recombinant EGFR, specifically the wild type EGFR extra-cellular domain (ECD) (EGFR 1-645) (SEQ ID NO: 34), EGFRvIII (EGFR (1-29)-G-(298-645) (SEQ ID NO: 46)) and a truncated wild type EGFR 1-525 (EGFR1 (1-525) (SEQ ID NO: 47)). Ab2 includes the heavy and light chain amino acid sequences of Ab2 as provided in SEQ ID NOs: 48 and 49, respectively, and was made according to standard methods.

While Ab1 and Ab2 are both anti-EGFR antibodies, they have distinct properties and bind to unique epitopes. Ab2 binds to the L2 domain of EGFR (Gan et al. (2012) *Cancer Res* 72(12)1-7; Li et al. (2005) *Cancer Cell* 7:301), whereas Ab1 binds to amino acid residues 287-302 of the CR1 domain (domain II) of EGFR (Gan et al. (2012) 72(12)1-7; Johns et al. (2004) *J Biol Chem* 279:30375-30384). Domain II of EGFR is exposed in the extended conformation of EGFR (Li et al. (2005) *Cancer Cell* 7:301). FIG. 17 provides a diagram of the overall structural domain organization of EGFR and indicates generally where the epitopes for Ab2 and Ab1 are located. Unlike Ab2, Ab1 does not bind (or has very weak binding) to the EGFR ECD (SEQ ID NO: 34). Although Ab1 can bind to activated wild type EGFR, and has a higher binding affinity for EGFRvIII versus Ab2 in vivo. Thus, Ab2 was used as a control in the experiments described herein as a second anti-EGFR antibody that binds to a different epitope and has different binding affinity characteristics than Ab1.

Biacore analysis was performed using a Biacore T100 with a CM5 sensory chip, and test antibodies were captured via anti-human Fc antibodies that were amino coupled to the chip using a standard amine coupling kit according to manufacturer's instructions (GE healthcare). Briefly, a CM5 chip surface was activated with EDC/NHS. Goat anti-human Fc specific polyclonal antibody (Thermo Fisher Scientific Inc., Rockford, Ill.) was diluted to 25 µg/mL in 10 mM sodium acetate (pH 4.5) and injected over the activated surface to achieve immobilization. Unreacted moieties on the biosensor surface were blocked with ethanolamine. The Biacore T100 is a surface plasmon resonance based biosensor for detecting, characterizing and quantifying bimolecular interactions, including the interactions between an antibody and its antigen. Antigen was injected at 804/minute for 3 minutes and dissociation was followed for 15 minutes. The EGFR ECD tested included amino acids 1-645 of EGFR fused to a myc and histidine tag (EGFR (1-645)-LESRGPF-Myc-NMHTG-6His ("LESRGPF" (SEQ ID NO: 90); "6His" (SEQ ID NO: 91)). The EGFRvIII variant was also fused to myc and histidine tag (EGFR (1-29)-G-(298-645)-LESRGPF-Myc-NMHTG-6His), as was the ECD EGFR 1-525 (EGFR1 (1-525)-SRGPF-Myc-NMHTG-6His ("SRGPF" (SEQ ID NO: 92)). The running buffer used in the Biacore analysis was HBS-EP+: 10 mM Hepes, pH7.5, 150 mM NaCl, 3 mM EDTA, 0.05% Tween 20.

Results from the Biacore binding analysis are shown in FIG. 3. Of the Ab1 variant antibodies tested, AbK had the highest binding affinity for truncated EGFR (1-525) with a $K_D$ of $1.7 \times 10^{-9}$ M, which was more than a 1300 fold increase over the $K_D$ of Ab1. As described in FIG. 3, AbE showed the lowest determinable affinity for truncated EGFR (1-525) with a $K_D$ of $5.9 \times 10^{-7}$ M, only about a 4 fold increase in affinity over the $K_D$ of Ab1. AbA showed a ten-fold improvement in $K_D$ for truncated EGFR (1-525) ($K_D$ of $2.2 \times 10^{-7}$ M (AbA) vs $K_D$ of $2.3 \times 10^{-6}$ M (Ab1)). The $K_D$ ratios of AbB, AbC, AbD, AbF, AbG, AbH, AbJ, AbL, AbM, AbN, AbO, and AbP versus Ab1 are also described in FIG. 3 for truncated EGFR 1-525.

Binding affinity of the Ab1 variant antibodies, Ab1, and Ab2 to EGFRvIII was also tested. As shown in FIG. 3, all of the Ab1 variants showed higher binding affinity to EGFRvIII than Ab1. For example, AbA dissociated from EGFRvIII with a $K_D$ of $2.3 \times 10^{-9}$ M, whereas Ab1 had a dissociation constant of $K_D$ of $9.4 \times 10^{-9}$ M. Thus, AbA had a four fold increase in affinity (determined by dissociation constants) versus Ab1.

Ab1 variant antibodies that showed a higher dissociation constant for truncated EGFR(1-525) relative to Ab1, did not necessarily show the same increase in affinity for EGFRvIII. For example, while AbO showed the greatest fold increase (63 fold) in affinity for EGFRvIII relative to Ab1, AbK showed the greatest fold increase (over 1300 fold increase) for truncated EGFR(1-525) relative to Ab1, as described in FIG. 3. In another example, AbG showed the second highest fold increase in binding to EGFRvIII among the Ab1 variant antibodies (with an increase of over 47 fold), yet ranked sixth in the affinity increase for truncated EGFR(1-525) relative to Ab1 (with a 263 fold increase), as described in FIG. 3.

Many of the Ab1 variants were determined in the Biacore testing as having lower affinity for both EGFR 1-525 and EGFRvIII than Ab2 which had, for example, a $K_D$ of $4.0 \times 10^{-9}$ M for truncated EGFR(1-525).

Biacore analysis revealed that neither Ab1 nor the Ab1 variant antibodies bound to the full length ECD of EGFR (EGFR amino acids 1-645). In contrast, Ab2 bound to the ECD of EGFR. Thus, despite the observation that binding of the Ab1 variants to the wild type EGFR ECD was absent or negligible, as was also observed for Ab1, increased binding affinity to the truncated receptor EGFR(1-525) increased with the Ab1 variants.

FACS (Fluorescence Activated Cell Sorting) Analysis

FACS analysis was performed to determine the binding characteristics of AbA to tumor cells (A431 cells) in comparison to Ab1 and Ab2. Using FACS analysis, the fluorescence intensity and cell count were determined where the amount of antibody bound to the cells was reflected in the fluorescence intensity (i.e., the value of geometric mean) obtained through analysis using flow cytometry software. Specifically, the binding activity of the antibody, which is represented by the amount of bound antibody, was be assessed by determining the value of the geometric mean.

A431 cells were harvested from flasks at approximately 80% confluence using a cell dissociation buffer. The harvested A431 cells were washed once in PBS/1% FBS (fetal bovine serum) (FACS buffer) then resuspended at $2.5 \times 10^6$ cells/mL in FACS buffer. 100 µL of cells/well were added to a round bottom 96-well plate. 10 µL of a 10× concentration of antibody was used (final concentrations are indicated in FIG. 4). Wells were washed twice with FACS buffer and resuspended in 50 µL of secondary antibody (AlexaFluor 488) diluted in FACS buffer. The plate was incubated at 4° C. for one hour and washed twice with FACS buffer. Cells were resuspended in 100 µL of PBS/1% formaldehyde and analyzed on a Becton Dickinson LSRII flow cytometer. Data were analyzed using WinList flow cytometry analysis software.

Results from the FACS analysis of Ab1, Ab2, and AbA binding to A431 tumor cells are provided in FIG. 4, which shows the geometric mean versus the concentration of antibody incubated with the cells. As described in FIG. 4, AbA had higher binding to EGFR on A431 tumor cells than Ab1, but AbA had a lower binding affinity in comparison to Ab2. The data in FIG. 4 represents direct binding of each antibody to its antigen.

As described in FIGS. 3 and 4, AbA had increased binding affinity to EGFR and showed increased binding to cells with high levels of EGFR (A431 tumor cells) relative to Ab1. It was also determined that AbA exhibited a more modest increase in binding to cells with lower levels of EGFR (data not shown), versus the binding to the A431 cells.

Example 3: Epitope Analysis of Anti-EGFR Antibodies

Tests were performed to determine whether the anti-EGFR antibodies identified in Example 1 had the same epitope as antibody Ab1 or whether the amino acid changes within Ab1 variant antibodies AbA, AbG, AbK, AbM, and AbP impacted epitope binding.

Competition Assay Analysis

A competition binding FACS assay was used to determine epitope specificity among the improved anti-EGFR antibodies in comparison to Ab1, Ab2, and Control 1 antibody (an anti-CD20 antibody (rituximab (Roche)) used as a negative control). U87MG cells (a human glioblastoma cell line (obtained from A. Scott, Ludwig Institute for Cancer Research) (U87MG cells are available from ATTC as ATCC HTB-14™; see also, e.g., U-87MG Cell Line human, Sigma-Aldrich) which express EGFRvIII were used. U87MG cells were harvested from flasks at approximately 80% confluence using a cell dissociation buffer. Cells were washed once in PBS/1% FBS (fetal bovine serum) (FACS buffer) then resuspended at $2.5 \times 10^6$ cells/mL in FACS buffer. 100 µL of cells/well were added to a round bottom 96-well plate. For competition FACS, Ab1 was fluorescently conjugated by addition of fluorescein isothiocyanate (FITC) at a final concentration of 100 nM (with or without the competing antibodies), and then wells were washed twice in FACS buffer, suspended in 100 µL of PBS/1% formaldehyde, and analyzed on a Becton Dickinson LSRII flow cytometer. Fluorescence was measured at 488 nM.

Figure 5:
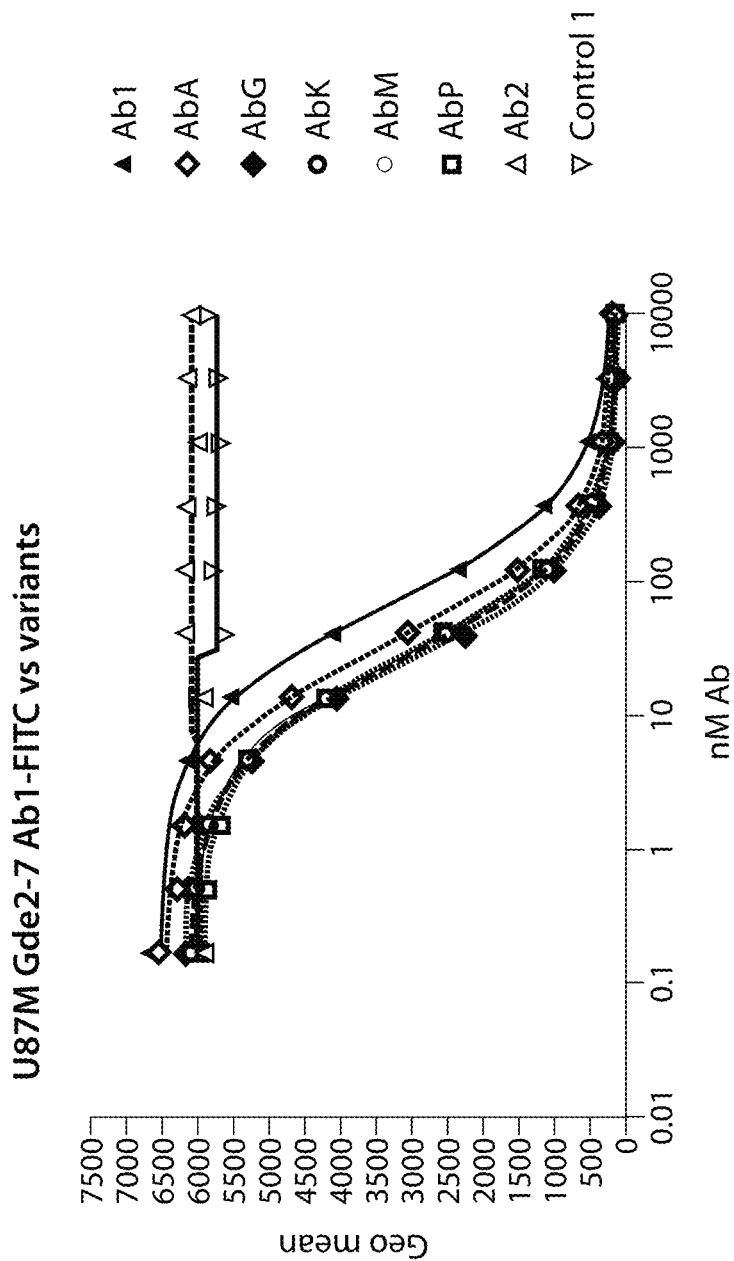
FIG. 5 depicts the results from a FACS competition assay that indicates that the Ab1 variant antibodies recognize the same EGFR epitope as Ab1.

The results from the competition assay are described in FIG. 5 and indicate that the Ab1 variant antibodies tested (i.e., AbA, AbG, AbK, AbM, and AbP) recognized the same epitope as Ab1 (domain II of EGFR, which is exposed in the "extended" EGFR conformation) given that the Geo mean calculation of fluorescence decreased with an increase in unlabeled Ab1 variant antibody concentration. The results also show that the Ab1/AbA/AbG/AbK/AbM/AbP epitope is distinct from the Ab2 epitope, as no competition between Ab2 and Ab1 or between Ab2 and the Ab1 variant antibodies was observed. The Control 1 antibody also showed no detectable binding to the Ab1 epitope in the competition assay, as the Control 1 antibody failed to compete with FITC labeled Ab1 for binding to the cells.

Imaging Analysis

Figure 20A:
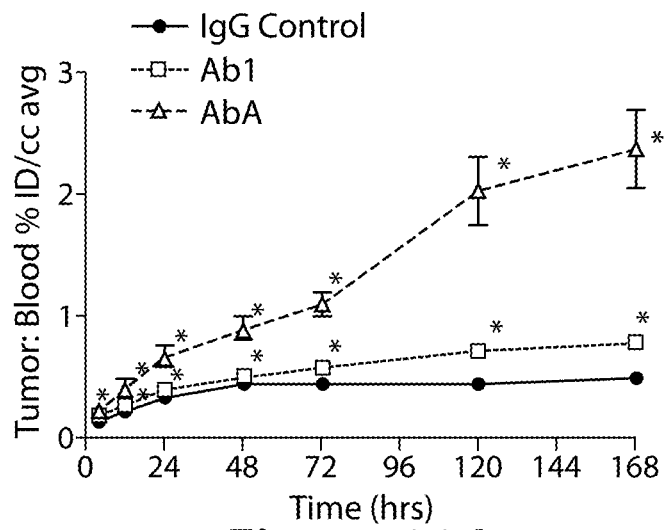
Figure 20B:
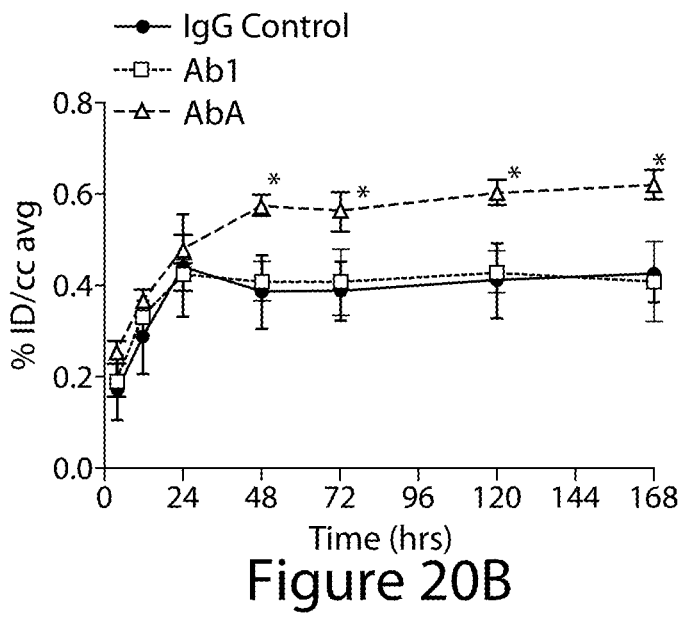

To evaluate the efficacy of antibody uptake by EGFR expressing tumors, a SPECT imaging assay was performed using AbA labeled with $^{111}$In (see, e.g., Khalil, et al. International Journal of Molecular Imaging, Vol. 2011, Article ID 796025, p. 1-15). Two tumor models, SW48 cells (colon tumor cells; ATCC No. CCL-231™) and EBC-1 cells (EBC-1 cells are from a human lung squamous cell carcinoma line that is from the Japanese Research Resources Bank (Id No. RCB1965) (Tokyo, Japan)) were chosen for their moderate EGFR expression levels based on immunohistochemistry analysis. Following injection of the tumor cells into the mice, and subsequent administration of the labelled AbA antibody, labelled Ab1, or the labelled negative control (a non-EGFR binding IgG), SPECT/CT images were acquired of the mice at 4, 12, 24, 48, 72, 120, and 168 hours post-injection using a nanoSPECT/CT. All labelled antibodies were dosed via venous tail injection. To account for differences in blood clearance for the antibodies, data are reported as the ratio of tumor to blood. The results provided in both FIGS. 20A and 20B demonstrate higher AbA uptake into both the SW48 (FIG. 20A) and EBC-1 (FIG. 20B) cells in the mouse compared to Ab1 and the IgG control. In the EBC1 model (FIG. 20B), which is the model with a lower level of EGFR expression, Ab1 uptake was similar to the IgG control while AbA uptake was higher than both Ab1 or the negative control. The results provided in FIG. 20 demonstrate that AbA is able to target specific EGFR-expressing tumors. Similar imaging results for AbA were also observed using A431 tumor cells (derived from an epidermoid carcinoma solid tumor (ATCC No. CRL-1555) known to have high levels of EGFR expression.)

Example 4: In Vitro Analysis of Anti-EGFR Antibody Activity in Tumor Cell Lines

In Vitro Analysis of EGFR Signaling in SCC-15 and H292 Tumor Cell Lines

The ability of Ab1, Ab2, AbA, AbB, AbC, AbD, AbG, AbK, AbM, and AbP to inhibit EGF-mediated tyrosine phosphorylation of EGFR in tumor cell lines in vitro was assessed by Western blot analysis using squamous carcinoma cells (SCC)-15 (ATCC® CRL-1623™) and H292 cells (lung carcinoma cell line; ATCC® CRL-1848™). Both SCC-15 and H292 cells express wild type EGFR. The down regulation of pEGFR in wild-type EGFR expressing tumor cells induced by antibody treatment indicates that those antibodies function at least in part by inhibition of signaling through the receptor. SCC-15 cells (human tongue squamous cell carcinoma) are transformed keratinocytes and are sensitive to Ab1 in vivo. While SCC-15 cells are sensitive to Ab1 in vivo, H292 (human non-small cell lung cancer (NSCLC)) cells are resistant to Ab1 inhibition of EGF-mediated tyrosine phosphorylation of EGFR both in vitro and in vivo. Thus, both cell lines were used to test the ability of AbA, AbB, AbC, AbD, AbG, AbK, AbM, and AbP to inhibit EGFR signaling in tumor cells in vitro.

Cells were either plated at 60,000-80,000 per well in 24-well plate, or were plated at 100,000-200,000 per well in 6-well tissue culture plates. Cells were incubated overnight in growth media. Following serum-starvation for 24 hours at 37° C., where appropriate, cells were incubated with the antibodies for one hour at 37° C., and then stimulated with recombinant human EGF (R&D Systems) for 10 minutes at 37° C. Cells were then washed twice with ice-cold PBS, and lysed with 100-200 µL/well of Cell Lysis Buffer (Cell Signaling Technology) supplemented with Complete Mini Protease Inhibitor Cocktail (Roche) and 0.1% NP40 (Tergitol-type NP-40; nonyl phenoxypolyethoxylethanol). After flash-freezing at −80° C. for at least 20 minutes, cell lysates were cleared by centrifugation at 14,000 rpm, for 10 minutes at 4° C. Protein concentrations of cleared sample lysates were determined via BCA Protein Assay (Pierce_Thermo Scientific). Cell lysates (10 µg) were resolved by SDS-PAGE using 4-12% bis-Tris, Midi gels, (Life Technologies) and transferred to nitrocellulose membranes using the iBlot Dry Transfer system (Life Technologies). Blots were blocked with 5% milk/Tween-Tris buffered saline (TTBS) for one hour at room temperature, washed three times with TTBS, and then incubated overnight with appropriate primary antibodies (anti-Phosphotyrosine (4G10) biotin conjugate, Millipore, 1:1000 dilution to detect phosphorylated EGFR; rabbit anti-EGFR, Lifespan Biosciences, 1:2000 dilution to detect total EGFR; rabbit anti-Pan actin, Cell Signaling Technology, 1:1000 dilution to detect the internal control actin) at 4° C. Following overnight incubation with primary antibodies, blots were washed three times with TTBS for five minutes, and then incubated for one hour at room temperature with either donkey anti-rabbit antibody (Jackson Laboratories, 1:2000 dilution) to detect total EGFR and actin, or incubated with streptavidin-HRP conjugate (KPL, 1:1000 dilution) to detect phosphorylated EGFR. Blots were then washed three times with TTBS, and treated with West Dura Chemiluminescent substrate (Thermo Scientific). Blots were visualized by scanning using an LAS-4000 scanner (Fuji).

Ab2 was used as a positive control (i.e., an inhibitor of EGFR phosphorylation) and Control 1 antibody was used as a negative control (i.e., does not bind EGFR and, therefore, has no impact on phosphorylated EGFR).

Figure 7A:
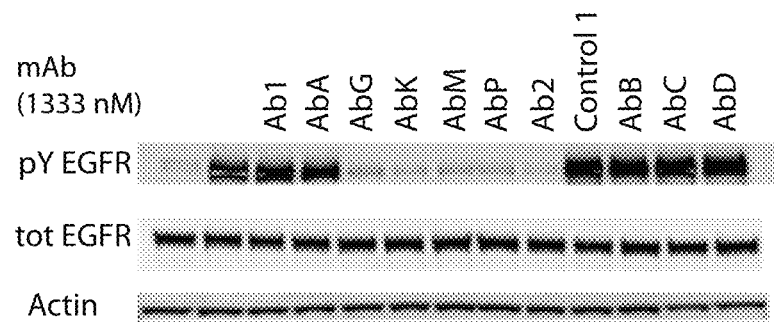
FIGS. 7A and 7B provide results from Western blot analysis examining the activity of Ab1 and the Ab1 variant antibodies on different cell lines in vitro. Cells from SCC-15 (FIG. 7A) and H292 cells were exposed to conditions as described in Example 4, and analyzed using Western Blot Analysis using anti-phosphotyrosine EGFR (pY EGFR), anti-EGFR (tot EGFR (total EGFR)), and anti-actin (actin) antibodies.

Results from the Western blot analysis of the in vitro study using SCC-15 cells are provided in FIG. 7A and indicate that Ab1 and antibodies AbA, AbB, AbC, and AbD were not able to significantly inhibit EGFR signaling in SCC-15 cells as indicated by no significant down regulation of phosphorylated EGFR. In contrast, a decrease in phosphorylated EGFR, as shown in FIG. 7A, indicated that antibodies AbG, AbK, AbP, and AbM decreased EGFR activity in SCC-15 cells in vitro given that the level of phosphorylated EGFR was lower relative to the negative control and Ab1 and comparable to the positive control (Ab2) levels. Thus, a number of Ab1 variants gained in vitro activity versus Ab1.

Figure 7B:
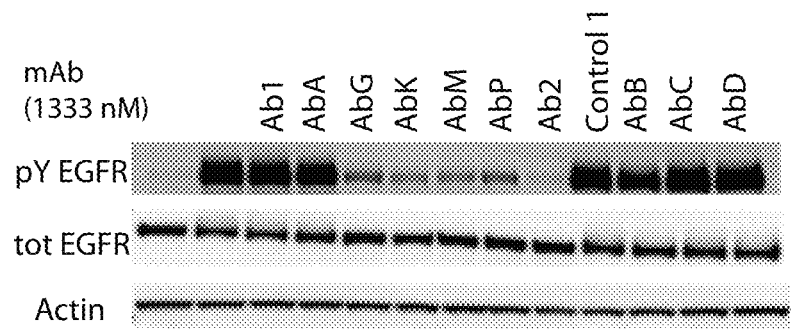

Results from the Western blot analysis of the in vitro study using H292 cells are provided in FIG. 7B. The results in FIG. 7B indicate that Ab1 and antibodies AbA, AbB, AbC, and AbD showed little inhibition of EGFR signaling in H292 cells in vitro with no significant reduction on phosphorylated EGFR in comparison to Ab2 and antibodies AbG, AbK, AbM, and AbP. Antibodies AbG, AbK, AbM, and AbP were more effective at inhibiting tyrosine phosphorylation of EGFR in H292 cells (see FIG. 7B) better than was Ab1. Ab2 (positive control) also inhibited EGFR phosphorylation, as described in FIG. 7B, whereas the negative control (Control 1 antibody) showed no detectable inhibition of phosphorylation given the results compared to Ab2.

As described below, while AbA was found to be relatively inactive at inhibiting EGFR phosphorylation in wild type EGFR positive cells (H292) in vitro, AbA was able to inhibit phosphorylation of these cells in vivo, in comparison to antibody Ab1 tested under the same conditions.

Thus, the in vitro results described in FIGS. 7A and 7B indicate that despite the increased binding of AbA, AbB, AbC, AbD, AbG, AbK, AbM, and AbP to EGFR (relative to Ab1), only some of the Ab1 variant antibodies (i.e., AbG, AbK, AbM, and AbP) were able to significantly inhibit or decrease EGF-mediated signaling in vitro in the tested tumor cell lines. Generally, the ability of the tested Ab1 variant antibodies to inhibit EGF-mediated tyrosine phosphorylation of EGFR in SCC-15 and H292 cells in vitro correlated with increased affinity to both EGFRvIII and truncated EGFR(1-525), as determined by surface plasmon resonance.

Figure 6:
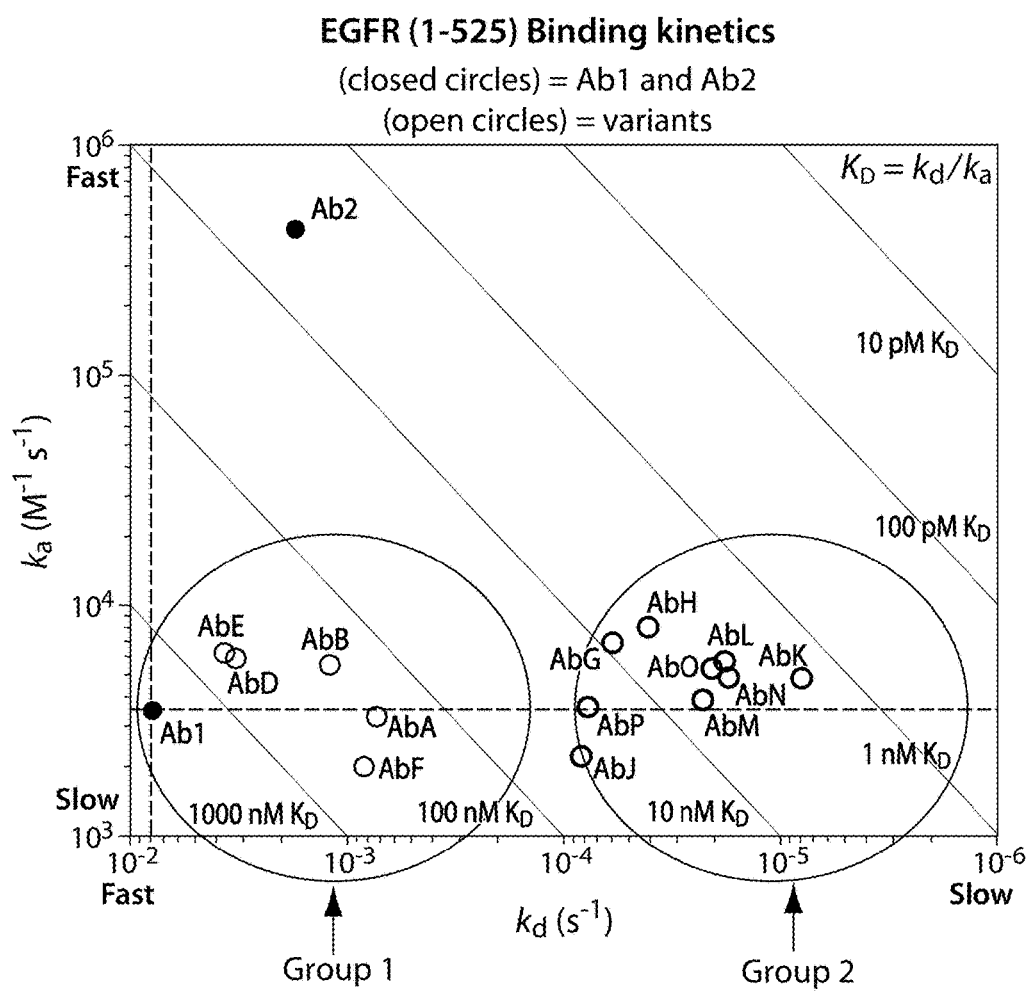
FIG. 6 provides a summary of the binding of Ab1 and the Ab1 variant antibodies to EGFR (1-525). Closed circles represent Ab1 or Ab2 (controls) and open circles represent the Ab1 variant antibodies. Circles indicate Group 1 and Group 2, summarizing data provided in FIG. 7

FIG. 6 provides a summary of the binding affinities of Ab1, Ab2, and the Ab1 variant antibodies to EGFR(1-525). The two circle outlines in FIG. 6 reflect the in vitro results described above (or results from similar tests) with respect to the ability of the antibody to inhibit EGFR phosphorylation (indicating inhibition of EGFR activity) in either H292 cells or SCC-15 cells. As described in FIG. 6, the Ab1 variant antibodies could be categorized into two groups (Groups 1 and 2): those that do not inhibit in vitro EGFR signaling in the tested tumor cell lines based on the results provided in FIG. 7 (including Ab1, AbA, AbB, AbD, AbE, and AbF; designated Group 1 in FIG. 6), and those that do inhibit EGFR signaling in vitro in the tested tumor cell lines (including AbG, AbH, AbL, AbK, AbJ, AbM, AbN, AbO, and AbP; designated Group 2 in FIG. 6) as described in FIG. 7. The comparison provided in FIG. 6 indicates that all of the Ab1 variant antibodies had higher affinity to EGFR(1-525) compared to Ab1, and that those with a $K_d$ of less than $1\times10^{-4}$ $s^{-1}$ (Group 2) were able to significantly inhibit EGFR-signaling in vitro as described in the results presented in FIG. 7. As described in FIG. 6, the maturation process of Ab1 resulted primarily in Ab1 variants having enhanced off-rates.

In Vitro Analysis of A431 Tumor Cell Line

The ability of Ab1 and the Ab1 variant antibodies to inhibit EGF-mediated phosphorylation of EGFR was also tested using A431 human epithelial carcinoma cells using a phospho-EGFR ELISA assay. A431 cells express wild type EGFR.

Cells were plated at 20,000 per well in collagen coated 96-well dishes in growth media. Twenty four hours later, cells were washed in serum free media and serum starved for four hours. Where appropriate, cells were pretreated with monoclonal antibody for one hour, and then stimulated with recombinant EGF for 10 minutes at 37° C. Following EGF stimulation, cells were washed twice with ice-cold PBS, and lysed with 100 pt/well of cell lysis buffer supplemented with protease inhibitors and flash-frozen at −80° C. for at least 20 minutes. Capture plates were generated by pre-coating wells with 50 µL of an anti-EGFR antibody (R&D systems, part number 841402, at 0.8 µg/mL), followed by blocking with PBS/1% BSA treatment for one hour, and washed three times in Tween-Tris buffered saline (TTBS). Cell lysates were added to capture plates and incubated at 4° C. overnight. Plates were washed five times in TTBS, and incubated with pTry-horse radish peroxidase (R&D Systems, DYC1095) for one hour. Plates were washed five times in TTBS and 100 µL of 3,3,5,5-tetramethylbenzidine (TMB) was added to each well and incubated at room temperature until color developed. Reactions were stopped by addition of 1N HCl, and OD was read at 450 nm.

Figure 8A:
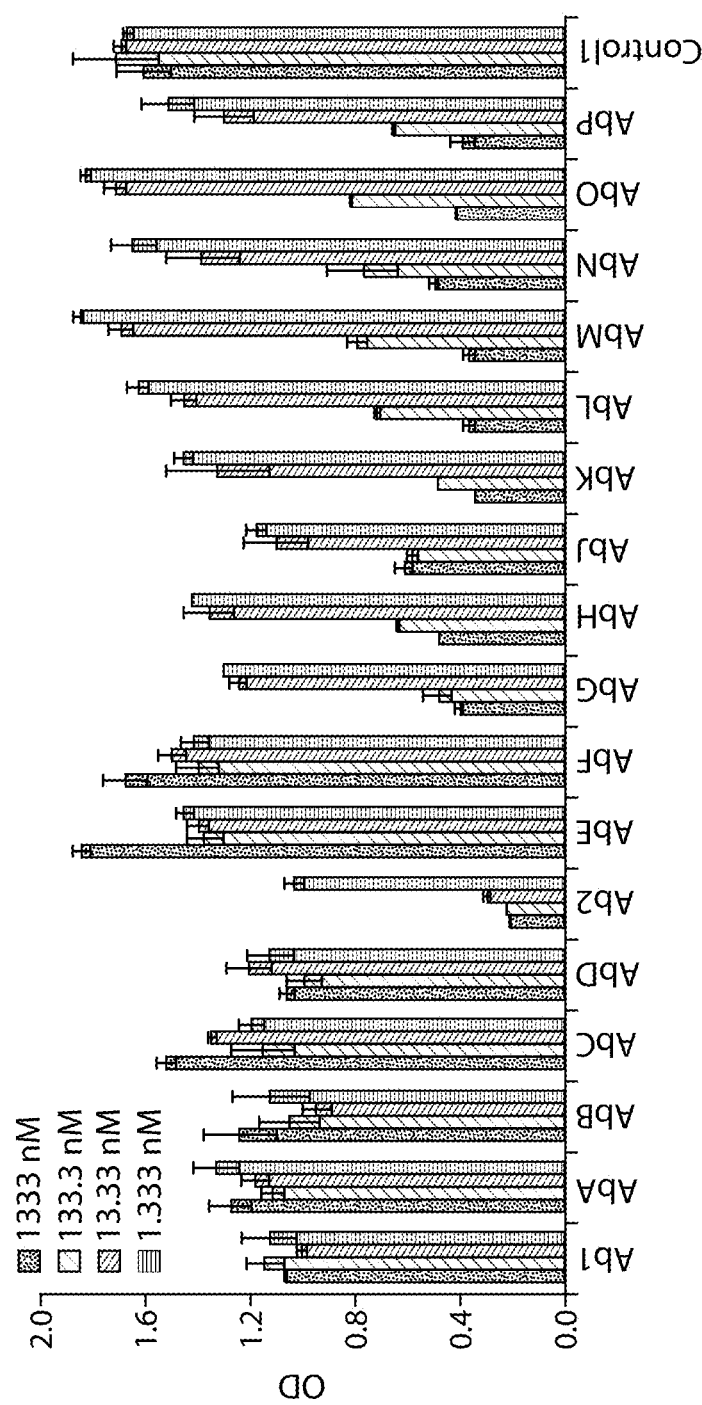
FIGS. 8A and 8B graphically depict results of pEGFR ELISA assays including Ab1, Ab2 and the Ab1 variants (FIG. 8A) and the level of inhibition of Ab1 in comparison to Ab2 and AbP (FIG. 8B) from the A431 inhibition study. The Y-axis of FIG. 8A is the optical density (OD) at 450 nm.
Figure 8B:
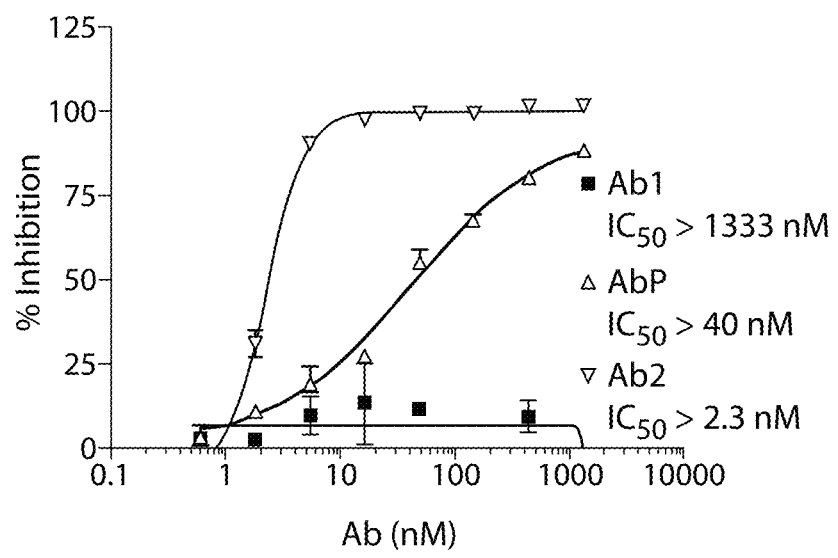

Results from the A431 inhibition study are described in FIGS. 8A and 8B and show that the Ab1 variant antibodies showed a range in their ability to inhibit EGFR activity in A431 cells. As shown in FIG. 8A, Ab1 and variants AbA, AbB, AbC, AbD, AbE, and AbF were ineffective at inhibiting EGFR signaling in A431 cells (determined by EGF-mediated phosphorylation of EGFR), even at concentrations of 1333 nM of antibody. In contrast Ab1variant antibodies AbG, AbH, AbJ, AbK, AbL, AbM, AbN, AbO, AbP, and AbQ were more effective at blocking EGFR phosphorylation than Ab1, albeit at a higher concentration than Ab2.

Control 1 antibody, which does not bind to EGFR, had no effect on EGFR inhibition of A431 cells.

FIG. 8B expands on the data provided in FIG. 8A for antibodies Ab1, AbP, and Ab2. As described in FIG. 8B, Ab1 showed low levels of inhibition, i.e., an average of 10% or less, in comparison to Ab2 or AbP. While Ab1 was determined to have an $IC_{50}$ value greater than 1333 nM at inhibiting EGFR signaling in A431 cells, AbP had an $IC_{50}$ value of greater than 40 nM, which was an improvement over Ab1. Ab2 had an $IC_{50}$ value of greater 2.3 nM.

Example 5: FACs Analysis of Anti-EGFR Antibodies in In Vitro Keratinocyte Binding Assay A keratinocyte FACs binding assay was performed to determine the binding affinity of the Ab1 variant antibodies to normal human epidermal keratinocyte (NHEK) cells. NHEK cells express wild type EGFR.

Cells were harvested when approximately 80% confluent using trypsin, neutralized and washed once in PBS/1% FBS (FACS buffer) then resuspended at $2.5\times10^6$ cells/mL in FACS buffer. 100 µL of cells/well were added to a round bottom 96-well plate. 10 µL of a 10× concentration of Ab (final concentrations are listed in the Figures) was added and plate was incubated at 4° C. for one hour. Wells were washed twice with FACS buffer then resuspended in 50 µL of secondary Ab (AlexaFluor 488) diluted in FACS buffer. The plate was incubated at 4° C. for one hour then washed twice with FACS buffer. Cells were then resuspended in 100 µL of PBS/1% formaldehyde and analyzed on a Becton Dickinson LSRII flow cytometer. Data was analyzed using WinList flow cytometry analysis software.

Figure 9:
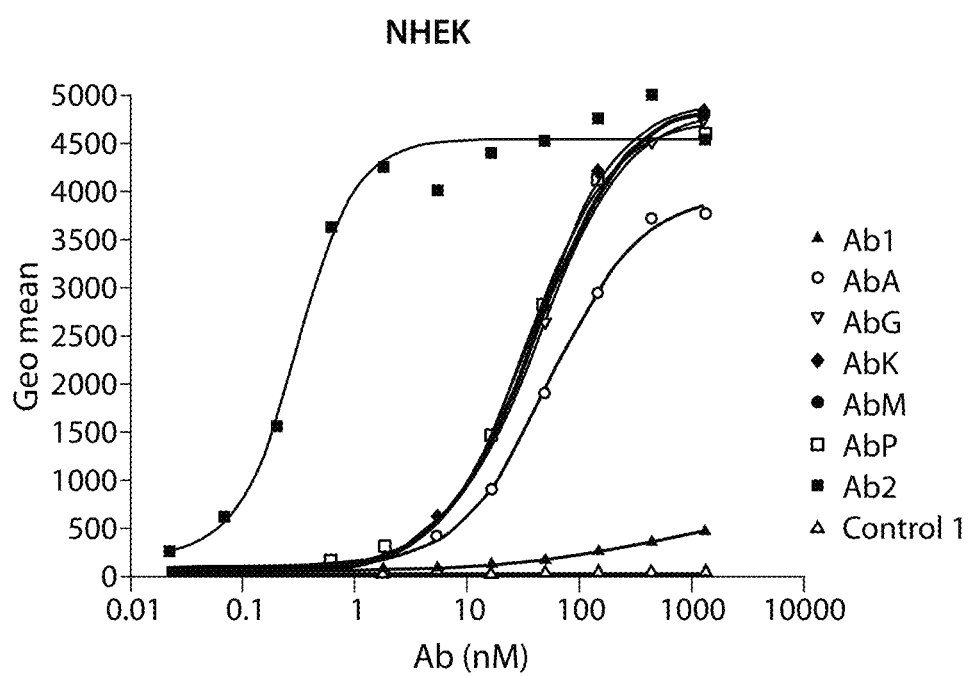
FIG. 9 graphically depicts binding of Ab1, Ab2, and the Ab1 variant antibodies to normal human epidermal keratinocytes expressing wild type EGFR using FACS binding assay.

The results from the in vitro keratinocyte binding assay are described in FIG. 9, which indicates that as the concentration of labeled AbA, AbG, AbK, AbM, and AbP antibody increased, the measured fluorescence increased due to binding of EGFR on the keratinocytes. Ab2 was used as a positive control and resulted in increased fluorescence with the addition of the antibody to the NHEK cells. Ab1 showed much lower levels of binding, even at high concentrations of antibody.

The results presented in FIG. 9 indicate that the tested Ab1 variant antibodies bind wild type EGFR on keratinocytes and have an affinity to normal human epidermal keratinocytes which is greater than Ab1 (and negative control, Control 1 antibody). The results in FIG. 9 also show that antibodies AbA, AbG, AbK, AbM, and AbP have lower binding to normal human epidermal keratinocytes as compared to Ab2. These results indicate that the Ab1 variant antibodies are able to bind wild type EGFR on keratinocytes better than Ab1.

Example 6: In Vivo Analysis of Anti-EGFR Antibodies on Tumors

The effect of the Ab1 variant antibodies on the growth of tumors in vivo was evaluated using a mouse xenograft assay.

SCID and athymic CD-1 nude mice were obtained from Charles River (Wilmington, Mass.). Ten mice were housed per cage. The body weight of the mice upon arrival was 18-20 g. All experiments were conducted in compliance with the National Institutes of Health Guide for Care and Use of Laboratory Animals guidelines in a facility accredited by the Association for the Assessment and Accreditation of Laboratory Animal Care. For each subcutaneous study, viable cells were inoculated subcutaneously into the right flank of the mice on Day 0. The injection volume was 0.2 mL composed of a 1:1 mixture of S-MEM and Matrigel (BD, Franklin Lakes, N.J.). Tumors were size matched at approximately 200-250 mm$^3$. Therapy began the day of, or 24 hours, after size matching the tumors. A human IgG mixture control was used as a negative control (purified human IgG analogous to human serum; Innovative Research). Mice weighed approximately 25 g at the onset of therapy. Tumor volume was estimated two to three times weekly. Measurements of the length (L) and width (W) of the tumor were taken via electronic caliper and the volume was calculated according to the following equation: V=(L× W$^2$)/2. Mice were euthanized when tumor volume reached 3,000 mm$^3$ or when skin ulcerations occurred. Appropriate amounts of the antibody stock were diluted in phosphate buffered saline prior to administration. Drugs were administered intraperitoneally as indicated in the figures. H292 (human non-small cell lung carcinoma (NSCLC)) cells were used in the xenograft study.

Figure 10:
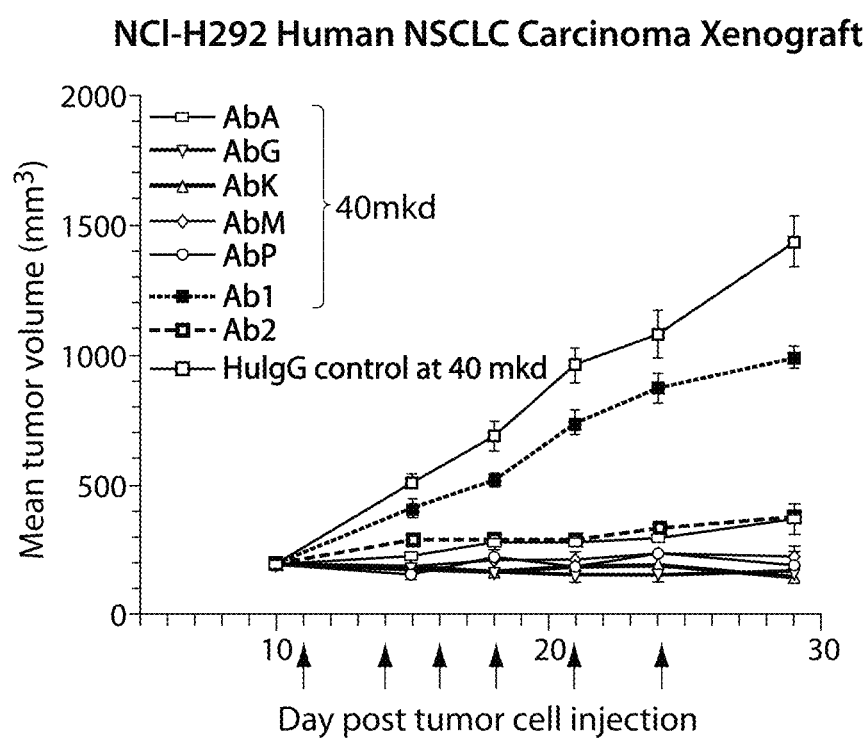
FIG. 10 graphically depicts the results of a mouse xenograft inhibition assay comparing the ability of AbA, AbG, AbK, AbM, and AbP to inhibit tumor growth in a human NSCLC carcinoma xenograft in comparison to Ab1, Ab2, and a human IgG (huIgG) control. Arrows indicate time points of administration of the various antibodies.

Results from the in vivo experiment show that Ab1 variant antibodies AbA, AbG, AbK, AbM, and AbP were able to significantly inhibit tumor growth relative to Ab1 (see FIG. 10). The Ab1 variant antibodies were also able to increase the durability of the duration of the response compared to Ab1, e.g., AbA maintained a tumor volume of less than 500 mm$^3$ for 29 days as versus Ab1 which maintained a tumor volume of less than 500 mm$^3$ for about 18 days post tumor cell injection (following the same dose and administration schedule). As shown in FIG. 10, at Day 20, mice injected with AbA showed an approximate tumor volume of 300 mm$^3$, whereas at Day 20 mice injected with Ab1 showed a tumor having an approximate volume of 700 mm$^3$. By Day 29, AbA injected mice showed a tumor having a similar volume as compared to the size at Day 20 (i.e., approximately 300 mm$^3$), whereas Ab1 injected mice had an increase in tumor volume to about 1000 mm$^3$.

The percent tumor growth inhibition (% TGI) was calculated in order to quantitate the results described in FIG. 10. The % TGI for the antibodies described in FIG. 10 are as follows:

AbA=74
AbG=88
AbK=90
AbM=84
AbP=86
Ab1=31
Ab2=73

The % TGI values are relative to the tumor volumes of mice treated with the human IgG control. As described above, Ab1 resulted in 31% TGI relative to the human IgG control, whereas AbA had a calculated 74% TGI. Notably, the Ab1 variant antibodies showed equal or greater % TGI relative to Ab2.

AbA was able to increase the durability of the response and decrease tumor volume in vivo in a H292 xenograft tumor model (as described in FIG. 10), yet failed to inhibit phosphorylation of EGFR in vitro in the same cell line, as described in Example 4 and FIG. 7. Antibody AbA activity in vivo was also comparable to antibodies AbG, AbK, AbM, and AbP despite having a lower binding affinity for EGFR (1-525) and EGFRvIII (see FIG. 3). Thus, despite the fact that AbA showed little to no cell signaling inhibition in vitro, AbA decreased or inhibited H292 tumor cell growth in vivo in a manner similar to other anti-EGFR variant antibodies having stronger affinity values, e.g., AbK, AbM, and AbP.

Example 7: In Vivo Tumor Growth Inhibition Assay Using AbA ADCs

The ability of an AbA-vcMMAE ADC to inhibit tumor growth was determined using an in vivo mouse xenograft assay. The AbA ADC used in this example was conjugated according to the method described in Example 8, but was not purified according to the batch purification method described therein. The average DAR for the AbA ADC composition used in this example was 3.7. Mouse xenograft assays (similar to those described in Example 6) were performed using two different NSCLC cells lines, NCI-H1703 and EBC1. Results from the two different cell lines are provided in FIG. 14.

Figure 14A:
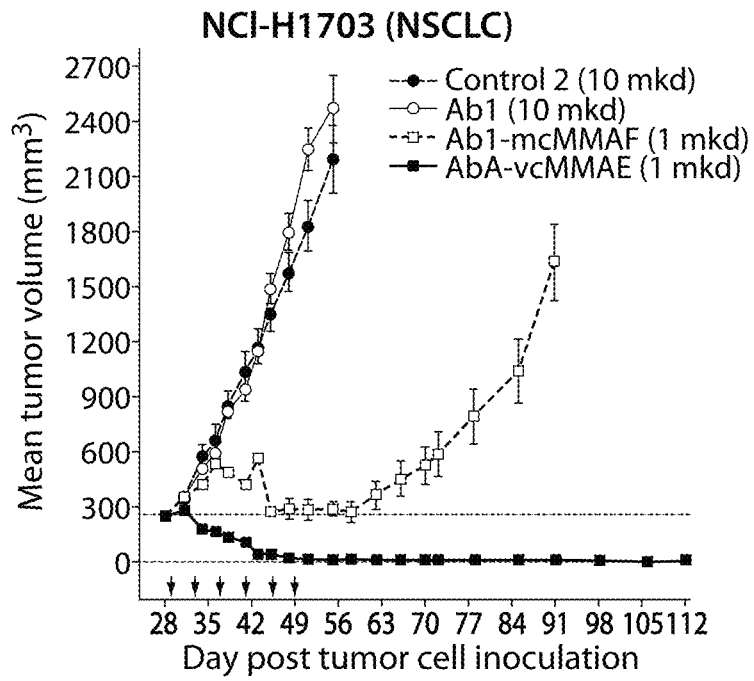
FIGS. 14A and 14B graphically depict results from two mouse xenograft inhibition assays using anti-EGFR ADCs.

As shown in FIG. 14A, AbA-vcMMAE (at a dose of 1 mg/kg body weight) was better at decreasing tumor volume and increasing the durability of the response in NCI-H1703 cells than Ab1 (at a dose of 10 mg/kg body weight) and compared to an Ab1 ADC containing Ab1 and MMAF with an mc linker. Ab1 alone (at a dose of 10 mg/kg) resulted in an overall lack of tumor volume inhibition similar to the negative control, antibody control 2 (an anti-tetanus toxin antibody) which did not inhibit tumor growth at a dose of 10 mg/kg.

Figure 14B:
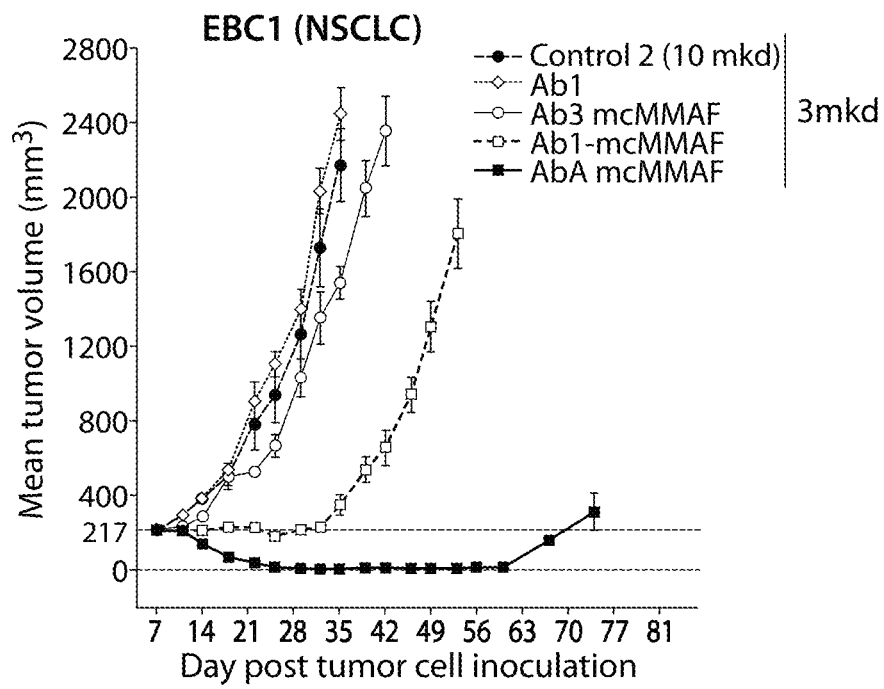

Efficacy of the AbA-vcMMAE ADC was also studied in a xenograft mouse model using EBC1 cells. The results from the study are shown in FIG. 14B and indicate that the AbA-mcMMAF ADC (at a dose of 3 mg/kg body weight) was more effective at decreasing tumor volume and increasing the durability of the response compared to Ab1 (at a dose of 3 mg/kg body weight) and compared to an Ab1 ADC containing Ab1 and MMAF with a mc linker (at a dose of 3 mg/kg body weight).

In sum, the results in FIG. 14 show that two different AbA auristatin ADCs (AbA-vcMMAE and AbA-mcMMAF) were effective at decreasing tumor volume and increasing the durability of the response in vivo relative to Ab1 alone or an Ab1-MMAF ADC.

Example 8: Purified Anti-EGFR Antibody Drug Conjugates (ADCs)

An antibody drug conjugate (ADC) was made comprising the AbA antibody linked to monomethyl auristatin E (MMAE) via a valine-citrulline (vc) linker. A diagram of this ADC, referred to as AbA-vcMMAE, is described in FIG. 11.

Conjugation of the AbA antibody with vcMMAE began with a partial reduction of AbA followed by reaction with Val-Cit-MMAE (vcMMAE). The AbA antibody (20 mg/mL) was partially reduced by addition of TCEP (molar equivalents of TCEP:mAb is 2.1) followed by incubation at 0° C. overnight. The reduction reaction was then warmed to 20° C. To conjugate all of the thiols, vcMMAE was added to a final vcMMAE:reduced Cys molar ratio of 1.15. The conjugation reaction was carried out in the presence of 10% v/v of DMSO and allowed to proceed at 20° C. for 60 minutes.

After the conjugation reaction, excess free N(acetyl)-Cysteine (2 equivalents vs. vcMMAE charge) was added to quench unreacted vcMMAE to produce the Cys-Val-Cit-MMAE adduct. The Cys quenching reaction was allowed to proceed at 20° C. for approximately 30 minutes. The Cys-quenched reaction mixture was purified as per below.

The above conjugation method can also be used to conjugate mcMMAF to an antibody.

Batch Purification

The AbA ADCs were purified using a batch purification method. The reaction mixture was treated with the appropriate amount of water washed Bu-HIC resin (ToyoPearl; Tosoh Biosciences), i.e., seven weights of resin was added to the mixture. The resin/reaction mixture was stirred for the appropriate time, and monitored by analytical hydrophobic interaction chromatography for removal of drug conjugate products, filtered through a coarse polypropylene filter, and washed by two bed volumes of a buffer (0.28 M sodium chloride, 7 mM potassium phosphate, pH 7). The combined filtrate and rinses were combined and analyzed for product profile by HIC HPLC. The combined filtrate and rinses were buffer exchanged by ultrafiltration/diafiltration (UF/DF) to 15 mM histidine, pH 6 with 10 diavolumes 15 nM histidine buffer.

Following conjugation and purification, analytical analysis of the resulting ADC mixture was performed. Samples were taken and analyzed using hydrophobic interaction chromatography-high-performance liquid chromatography (HIC-HPLC). The column used was a TSK gel Butyl-NPR column (4.6 mm ID×3.5 cm, 2.5 µm, 30° C.; Tosoh Bioscience LLC, Japan) and was used at a flow rate of 0.8 mL/min. The mobile phases included A: 25 mM $Na_2HPO_4$, pH7, 1.5 M$(NH_4)_2SO$ and B: 25 mM $Na_2HPO_4$, pH7 (75%) to IPA (25%). The gradient used was 0% phase B for 2 minutes, 0 to 100% B in 12 minutes, and hold for 1 minute.

The protein content was analyzed using UV analysis. HIC trace analysis showed that the resulting average Drug to Antibody Ratio (DAR) for AbA-vcMMAE was 3.1, as described below in Table 4 and FIG. 12. The average DAR was determined by summing up the 0, 1, 2, 3, 4, 5, 6, 7 and 8 ADC product, multiplying PA % (PA % is the peak area percent as determined by the area measured under the peak at $A_{280}$ by requisite drug load), and dividing by 100.

TABLE 4

Results of HIC Analysis (PA %) of AbA-vcMMAE using Batch Purification HIC pa % results @ 280 nm

| Rentention time min | DAR | Broad Distribution | Purified (Batch) |
|---|---|---|---|
| 6.7 | 0 | 4.27 | 6.15 |
| 7.6 | 1 | 0.67 | 1.43 |
| 8.6 | 2 | 24.74 | 34.27 |
| 9.6 | 3 | 1.95 | 3.94 |
| 10.4 | 4 | 35.28 | 45.88 |
| 11.5 | 5 | 4.67 | 5.37 |
| 11.9 | 6 | 13.90 | 2.09 |
| 12.4 | 7 | 6.40 | 0.88 |
| 12.9 | 8 | 8.12 | |
| Σ (>E6), pa % 280 nm = | | 28.4 | 3.0 |
| E4/E2 = | | 1.4 | 1.3 |
| DAR = | | 4.1 | 3.1 |

As can be seen from Table 4 and FIG. 12, batch purification of AbA-vcMMAE resulted in a DAR of between 2-4. The initial average DAR was 4.1, where the final average DAR following purification was 3.1.

Figures 1, 13:
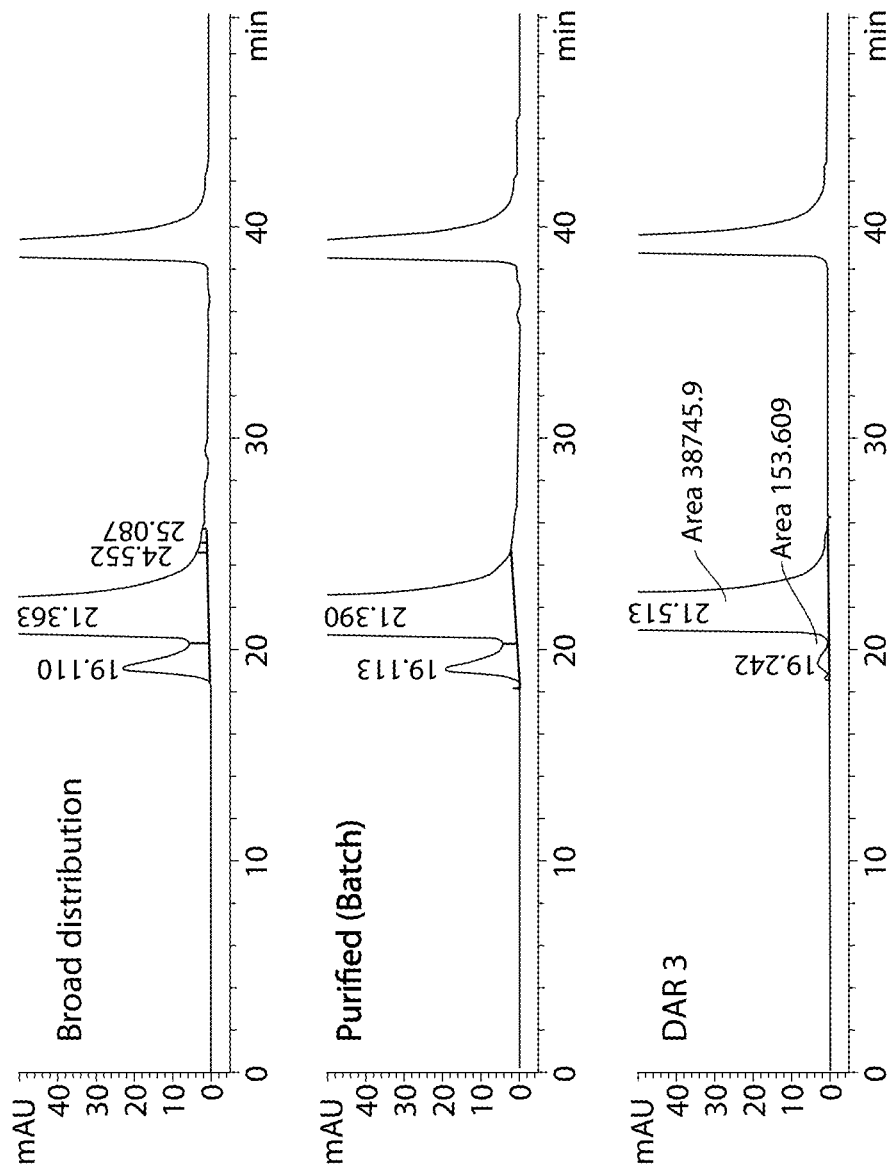
Figures 2, 13:
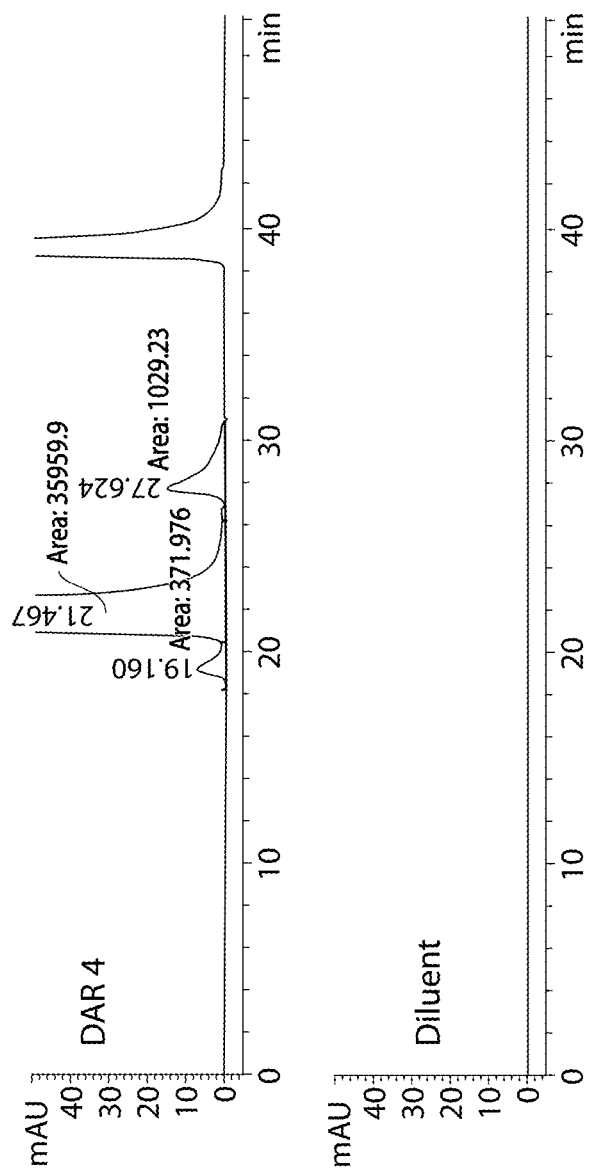

The AbA-vcMMAE ADC mixture was also analyzed by size-exclusion chromatography (SEC). SEC HPLC was performed using a Tosoh TSKgel GS3000SWXL column (7.58×30 cm, 5 µm. A flow rate of 0.3 mL/min was used. The mobile phases included 92.5% at 25 mM $Na_2PO_4$, pH 6.8, 350 mM NaCl and 7.5% isopropyl alcohol (IPA). The diluent was the mobile phase, and the analysis was performed at a UV at 214 nm. SEC pa % results @214 nm are provided below in Table 5. SEC results are shown in FIG. 13.

TABLE 5

SEC Results (PA %) of AbA-vcMMAE

| | High Molecular Weight | Monomer | Low Molecular Weight |
|---|---|---|---|
| Broad | 3.2 | 96.8 | |
| Purified | 2.2 | 97.8 | |
| DAR 2 | 0.4 | 99.6 | |
| DAR4 | 1.0 | 96.2 | 2.8 |
| mAb | | 95.9 | |
| AbA | | | |

SEC PA % results at 214 nm

Thus, batch purification of AbA-vcMMAE resulted in a DAR of the between 2-4, with an average of 3.1.

Example 9: In Vivo Tumor Growth Inhibition Assay Using AbA-MMAE ADCs

As described in Example 8, purified compositions of AbA-vcMMAE were prepared such that the average DAR of the ADCs within the composition was 3.1. The purified ADCs were subsequently tested to determine whether the purified AbA ADC composition was effective at inhibiting tumor growth in vivo using a lung cancer xenograft model. More specifically, xenograft tumor growth inhibition assays were performed to assess the effect of purified AbA-vcMMAE (Ab1-vcMMAEp) on NCI-H292 cells (a human NSCLC carcinoma cell line).

Figure 15A:
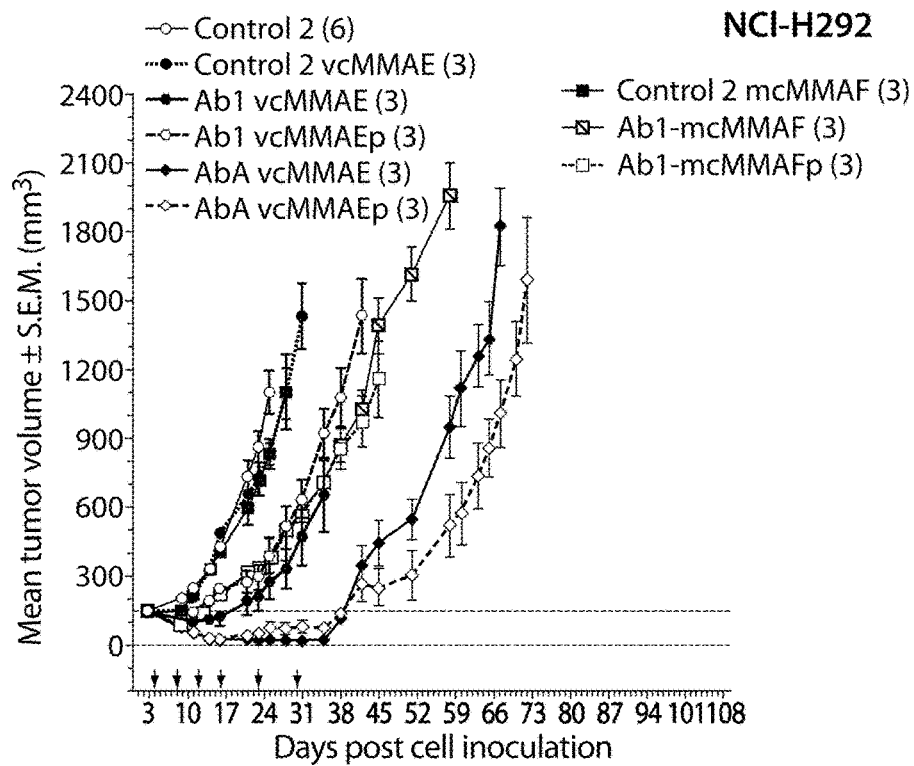
FIGS. 15A and 15B graphically depict results from mouse xenograft inhibition assays using anti-EGFR ADCs.
Figure 15B:
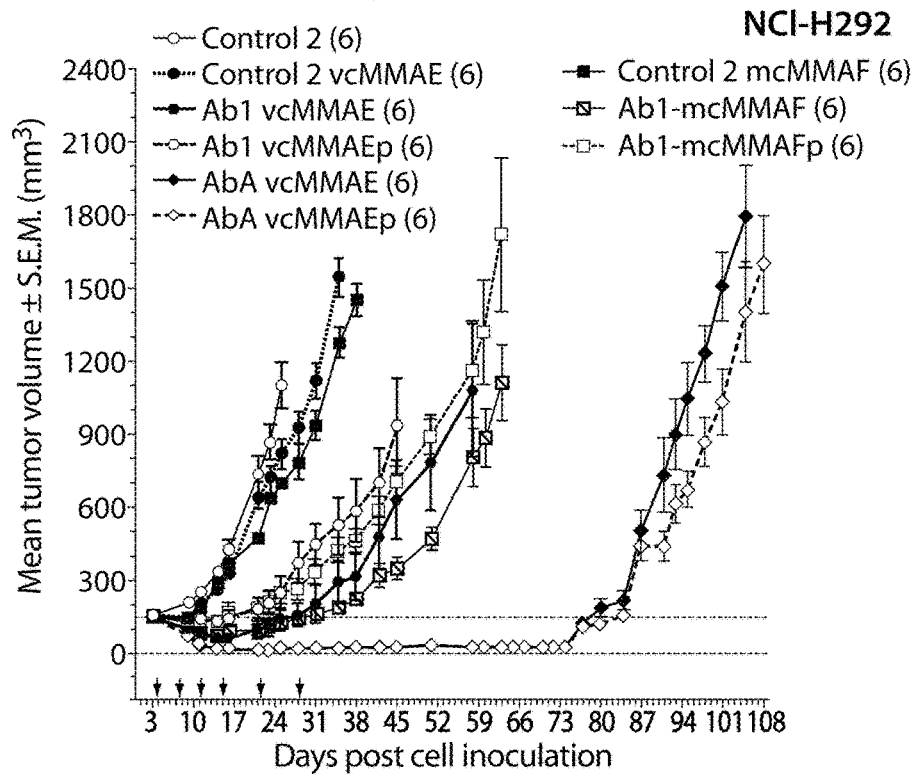

The results provided in FIG. 15A demonstrate that AbA-vcMMAEp (at a dose of 3 mg/kg body weight) was more effective at decreasing tumor volume and extending the duration of the response (increasing the durability of the response) in NCI-H292 cells when compared to the unpurified AbA-vcMMAE. Similarly, FIG. 15B demonstrates that the purified AbA-vcMMAEp (at a dose of 6 mg/kg body weight) was also more effective at inhibiting tumor growth when compared to the unpurified form of AbA-vcMMAE. As described in both FIGS. 15A and 15B, purified AbA-vcMMAE was also more effective at decreasing tumor volume and extending the duration of the response than the negative Control 2 antibody (alone or conjugated to MMAE), Ab1 conjugated to MMAE or MMAF in either the unpurified or purified form. The control 2 antibody is an anti-tetanus toxin antibody which does not bind to EGFR.

Figure 18:
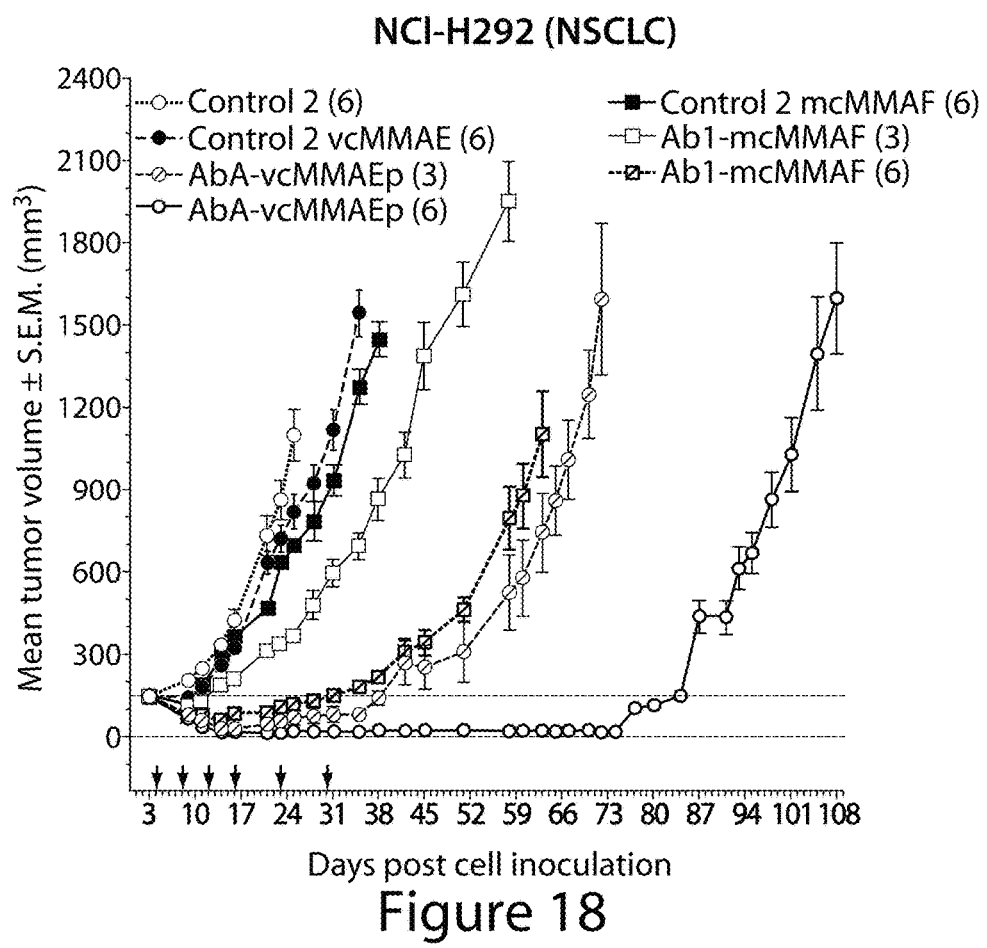
FIG. 18 graphically depicts results from mouse xenograft inhibition assays (using NCI-H292 (NSCLC) cells) using anti-EGFR ADCs. Doses of the molecules are indicated in parentheses, i.e., 3 mg/kg or 6 mg/kg. Arrows indicate time points of administration of the antibody or ADC.

In a further study assessing the effect of purified AbA-vcMMAE (Ab1-vcMMAEp) on NCI-H292 cells (lung carcinoma cell line; ATCC® CRL-1848™), purified AbA-vcMMAE was tested at a dose of 3 mg/kg and 6 mg/kg versus Ab1-mcMMAF at similar doses. The results of this second study in the NSCLC tumor model are provided in FIG. 18, and demonstrate that purified AbA-vcMMAEp was more effective at inhibiting tumor growth when compared to AbA-vcMMAE.

Example 10: Flow Through Process Purification of AbA-vcMMAE

Compositions comprising AbA-vcMMAE ADCs with reduced drug loads of vc-MMAE molecules per antibody were made using the flow through process. Preparation of the AbA-vcMMAE ADCs is described above in Example 7.

A flow through process for purifying a composition of AbA-vcMMAE having ADCs with a range of DARs (1-8) was performed according to the following. A 5 mL column of the Bu-HIC resin was first equilibrated with approximately 28 mM NaCl, 7 mM potassium phosphate, pH 7. The reaction mixture was subsequently diluted with ⅙ its volume using 1.95 M NaCl, 50 mM potassium phosphate, pH 7, and loaded into the resin at an approximate ratio of 100 mg of protein/mL of resin at a flow rate of 1 mL/min (approximately 5 min residence time or 36 cm/hr linear flow). A rinse consisting of 1 part isopropanol and 10 parts (by volume) of 28 mM NaCl, 7 mM potassium phosphate, pH 7, was applied as a rinse for about 12 column volumes. The product was collected beginning approximately after 1 column volume, until after the UV signal equilibrated (which may also be collected in fractions). The fractions were analyzed by HIC HPLC and the desired aliquots were pooled together and concentrated by TFF (tangential flow filtration) and exchanged to 15 mM histidine, pH 6 with 10 diavolumes of the histidine buffer. Table 6 below, provide purity results for the reaction mixture before and after purification.

TABLE 6

Results of HIC Analysis (PA %) of AbA-vcMMAE using Flow Through Purification HIC PA % results @ 280 nm

| Rt, min | DAR | Broad Distribution | Purified (Flow Through) |
|---|---|---|---|
| 6.4 | 0 | 3.89 | 5.25 |
| 7.2 | 1 | 0.67 | 0.99 |
| 8.4 | 2 | 22.36 | 30.21 |
| 9.4 | 3 | 2.95 | 4.04 |
| 10.2 | 4 | 39.82 | 52.76 |
| 11.3 | 5 | 5.41 | 4.67 |
| 11.8 | 6 | 12.52 | 1.42 |
| 12.3 | 7 | 5.31 | 0.67 |
| 12.9 | 8 | 7.07 | |
| Σ (>E6), pa % 280 nm = | | 24.9 | 2.1 |
| E4/E2 = | | 1.8 | 1.7 |
| DAR = | | 4.1 | 3.2 |

In comparison to the batch purification described in Example 8, loading of protein versus resin was comparable for each purification mode (batch purification and flow through purification). In the batch purification process, 2.26 weights of resin was used versus ADC on a potency adjusted basis. The density of the resin was approximately 0.23 g/ml. Thus, for example, if 10 g ADC was used, 98.2 ml resin was used. The loading used was (10 g×1000 ml/L)/98.2 ml=102 g/L loading. The flow through purification experiments target a loading of 100 g/L. In each case the load solution and rinse solutions were the same, except that the flow through purification rinse solution was 10% IPA v/v.

A comparison between a purified AbA-vcMMAE composition obtained using the batch purification method described in Example 8 and a purified AbA-vcMMAE composition obtained using the flow through process described above, is provided in Table 7.

TABLE 7

Results of HIC Analysis (PA %) of AbA-vcMMAE Batch Purification versus Flow Through Purification HIC PA % results @ 280 nm

| Rt, min | DAR | Purified (Batch) | Purified (Flow Through) |
|---|---|---|---|
| 6.4 | 0 | 4.99 | 5.25 |
| 7.2 | 1 | 1.02 | 0.99 |
| 8.4 | 2 | 30.99 | 30.21 |
| 9.4 | 3 | 4.61 | 4.04 |
| 10.2 | 4 | 50.75 | 52.76 |

TABLE 7-continued

Results of HIC Analysis (PA %) of AbA-vcMMAE Batch Purification versus Flow Through Purification HIC PA % results @ 280 nm

| Rt, min | DAR | Purified (Batch) | Purified (Flow Through) |
|---|---|---|---|
| 11.3 | 5 | 5.5 | 4.67 |
| 11.8 | 6 | 2.1 | 1.42 |
| 12.3 | 7 | — | 0.67 |
| Σ (>E6), pa % 280 nm = | | 2.1 | 2.1 |
| E4/E2 = | | 1.6 | 1.7 |
| DAR = | | 3.2 | 3.2 |

In sum, both the flow through and batch purification processes were successful in obtaining a composition comprising about 80% ADCs having a DAR of 2-4, where the amount of ADCs having a DAR of 0-1 or 5-8 was limited to less than about 20% of the overall ADC population in the composition, as shown, e.g., in Table 7.

Example 11: In Vivo Tumor Growth Inhibition Assay Using AbA MMAE ADCs

Figure 19:
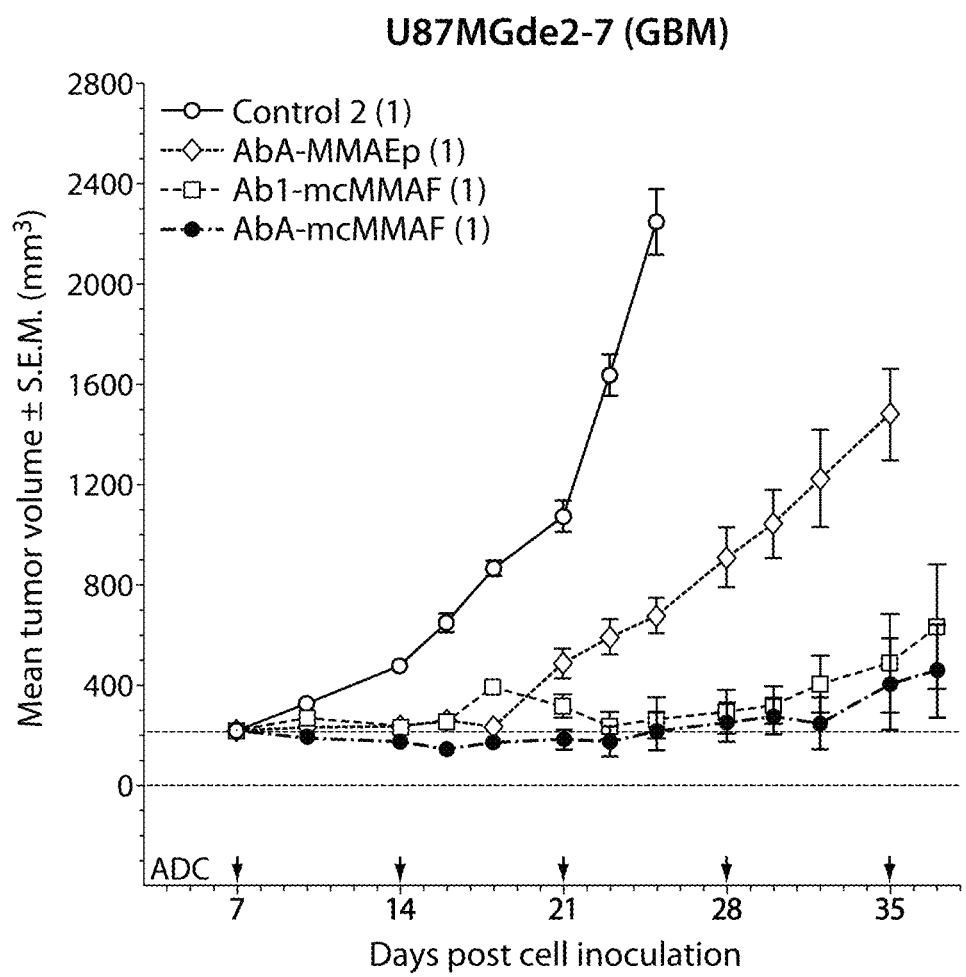
FIG. 19 graphically depicts results from a mouse glioblastoma xenograft inhibition assay using anti-EGFR MMAE and MMAF ADCs. Doses of the molecules in FIG. 19 are indicated in parentheses, i.e., 1 mg/kg. Arrows indicate time points of administration of the antibody or ADC. Control 2 in FIG. 19 represents a negative control which is an anti-tetanus toxin antibody which does not bind to EGFR.

The ability of an AbA-vcMMAE ADC to inhibit glioblastoma tumor growth was determined using an in vivo mouse xenograft assay. Mouse xenograft assays (similar to those performed in Example 6) were performed using U87MGde2-7 cells (which express EGFRvIII). U87 cells are derived from a human maliganant gliomas (ATCC No. HTB-14™). For the study, tumor cells were mixed with 50% Matrigel (BD BioSciences, Franklin Lakes, N.J.) and $3 \times 10^6$ cells were inoculated subcutaneously into the flank of 6-8 week old Nu/Nu female mice at Day 0 (Nu/Nu female mice were obtained from Charles River (Wilmington, Mass.)). Measurements of the length (L) and width (W) of the tumor were taken via electronic caliper and the volume was calculated according to the following equation: $V=(L \times W^2)/2$. Mice were euthanized when tumor volume reached 3,000 $mm^3$ or when skin ulcerations occurred. The results provided in FIG. 19 demonstrate that AbA-vcMMAEp was more effective than the negative control (Control 2 antibody; anti-tetanus antibody) in inhibiting glioblastoma cell growth.

SEQUENCE SUMMARY

| SEQ ID NO: | Description |
|---|---|
| 1 | Ab1 VH amino acid sequence |
| 2 | Ab1, AbC, AbD, and AbE VH CDR1 amino acid sequence |
| 3 | Ab1, AbC, AbD, AbE, AbF, AbJ, and AbN VH CDR2 amino acid sequence |
| 4 | Ab1, AbC, AbD, and AbE VH CDR3 amino acid sequence |
| 5 | Ab1 and AbA VL amino acid sequence |
| 6 | Ab1, AbA, AbB, AbC, and AbF VL CDR1 amino acid sequence |
| 7 | Ab1, AbA, AbB, and AbC, and AbF VL CDR2 amino acid sequence |
| 8 | Ab1, AbA, AbB, and AbF VL CDR3 amino acid sequence |
| 9 | AbA VH amino acid sequence |
| 10 | AbA, AbF, and AbK VH CDR1 amino acid sequence |
| 11 | AbA, AbH, AbK, AbL, AbM, AbO, and AbQ VH CDR2 amino acid sequence |
| 12 | AbA, AbF, AbM, AbN, and AbO VH CDR3 amino acid sequence |
| 13 | Ab1 and AbA light chain amino acid sequence |
| 14 | Ab1 heavy chain amino acid sequence |

| SEQ ID NO: | Description |
|---|---|
| 15 | AbA heavy chain amino acid sequence |
| 16 | AbB and AbG VH CDR1 amino acid sequence |
| 17 | AbB and AbG VH CDR2 amino acid sequence |
| 18 | AbG, AbH, AbJ, and AbL VH CDR3 amino acid sequence |
| 19 | AbB and AbK VH CDR3 amino acid sequence |
| 20 | AbM and AbN VH CDR1 amino acid sequence |
| 21 | AbP VH CDR1 amino acid sequence |
| 22 | AbP and AbQ VH CDR3 amino acid sequence |
| 23 | AbG, AbH, and AbJ VL CDR1 amino acid sequence |
| 24 | AbG, AbH, and AbJ VL CDR2 amino acid sequence |
| 25 | AbG, AbH, and AbJ VL CDR3 amino acid sequence |
| 26 | AbK, AbL, AbM, AbN, and AbO VL CDR1 amino acid sequence |
| 27 | AbE, AbK, AbL, AbM, AbN, and AbO VL CDR2 amino acid sequence |
| 28 | AbK, AbL, AbM, AbN, and AbO VL CDR3 amino acid sequence |
| 29 | AbP and AbQ VL CDR1 amino acid sequence |
| 30 | AbP and AbQ VL CDR2 amino acid sequence |
| 31 | AbD, AbP, and AbQ VL CDR3 amino acid sequence |
| 32 | Human EGFR amino acid sequence (with signal sequence) |
| 33 | Human Epidermal Growth Factor Receptor variant III (hEGFRvIII) amino acid sequence |
| 34 | Human EGFR extracellular domain (ECD) amino acid sequence |
| 35 | VH CDR1 consensus sequence of AbA, AbG, AbK, AbM, and AbP |
| 36 | VH CDR2 consensus sequence of AbA, AbG, AbK, AbM, and AbP |
| 37 | VH CDR3 consensus sequence of AbA, AbG, AbK, AbM, and AbP |
| 38 | VL CDR1 consensus sequence of AbA, AbG, AbK, AbM, and AbP |
| 39 | VL CDR2 consensus sequence of AbA, AbG, AbK, AbM, and AbP |
| 40 | VL CDR3 consensus sequence of AbA, AbG, AbK, AbM, and AbP |
| 41 | Ig gamma-1 constant region |
| 42 | Ig gamma-1 constant region mutant |
| 43 | Ig kappa constant region |
| 44 | Ig lambda constant region |
| 45 | Epitope of EGFR |
| 46 | ECD of EGFRvIII amino acid sequence |
| 47 | EGFR 1-525 amino acid sequence |
| 48 | Heavy chain amino acid sequence Ab2 |
| 49 | Light chain amino acid sequence Ab2 |
| 50 | VH amino acid sequence AbE |
| 51 | VL amino acid sequence AbE |
| 52 | VH amino acid sequence AbF |
| 53 | VL amino acid sequence AbF |
| 54 | VH amino acid sequence AbH |
| 55 | VL amino acid sequence AbH |
| 56 | VH amino acid sequence AbJ |
| 57 | VL amino acid sequence AbJ |
| 58 | VH amino acid sequence AbL |
| 59 | VL amino acid sequence AbL |
| 60 | VH amino acid sequence AbN |
| 61 | VL amino acid sequence AbN |
| 62 | VH amino acid sequence AbO |
| 63 | VL amino acid sequence AbO |
| 64 | VH amino acid sequence AbB |
| 65 | VL amino acid sequence AbB |
| 66 | VH amino acid sequence AbC |
| 67 | VL amino acid sequence AbC |
| 68 | VH amino acid sequence AbD |
| 69 | VL amino acid sequence AbD |
| 70 | VH amino acid sequence AbQ |
| 71 | VL amino acid sequence AbQ |
| 72 | VH amino acid sequence AbG |
| 73 | VL amino acid sequence AbG |
| 74 | VH amino acid sequence AbK |
| 75 | VL amino acid sequence AbK |
| 76 | VH amino acid sequence AbM |
| 77 | VL amino acid sequence AbM |
| 78 | VH amino acid sequence AbP |
| 79 | VL amino acid sequence AbP |
| 80 | AbH, AbJ, AbL, and AbO VH CDR1 amino acid sequence |
| 81 | AbQ VH CDR1 amino acid sequence |
| 82 | AbD and AbE VL CDR1 amino acid sequence |
| 83 | AbD VL CDR2 amino acid sequence |
| 84 | AbC VL CDR3 amino acid sequence |
| 85 | AbE VL CDR3 amino acid sequence |
| 86 | AbA heavy chain nucleic acid sequence |
| 87 | AbA light chain nucleic acid sequence |
| 88 | Heavy chain amino acid leader sequence |
| 89 | Light chain amino acid leader sequence |

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-human epidermal growth factor receptor (anti-hEGFR) antibody comprising
   a heavy chain CDR3 domain comprising the amino acid sequence set forth in SEQ ID NO: 12, a heavy chain CDR2 domain comprising the amino acid sequence set forth in SEQ ID NO: 11, and a heavy chain CDR1 domain comprising the amino acid sequence set forth in SEQ ID NO: 20; and
   a light chain CDR3 domain comprising the amino acid sequence set forth in SEQ ID NO: 28, a light chain CDR2 domain comprising the amino acid sequence set forth in SEQ ID NO: 27, and a light chain CDR1 domain comprising the amino acid sequence set forth in SEQ ID NO: 26,
   wherein the antibody is an IgG isotype.

2. The antibody of claim 1, wherein the antibody comprises a heavy chain variable region comprising the amino acid sequence set forth in SEQ ID NO: 76, and a light chain variable region comprising the amino acid sequence set forth in SEQ ID NO: 77.

3. The antibody of claim 1, which is conjugated to at least one drug.

4. The antibody of claim 3, wherein the at least one drug is selected from the group consisting of a dolastatin, a maytansinoid, and a plant alkaloid.

5. The antibody of claim 3, wherein the at least one drug is an auristatin.

6. An isolated nucleic acid encoding the antibody of claim 1.

7. An antibody drug conjugate (ADC) comprising an anti-human epidermal growth factor receptor (anti-hEGFR) antibody conjugated to at least one auristatin, wherein the anti-hEGFR antibody is an IgG isotype and comprises
   a heavy chain variable region comprising a CDR3 domain comprising the amino acid sequence set forth in SEQ ID NO: 12, a CDR2 domain comprising the amino acid sequence set forth in SEQ ID NO: 11, and a CDR1 domain comprising the amino acid sequence set forth in SEQ ID NO: 20; and
   a light chain variable region comprising a CDR3 domain comprising the amino acid sequence set forth in SEQ ID NO: 28, a CDR2 domain comprising the amino acid sequence set forth in SEQ ID NO: 27, and a CDR1 domain comprising the amino acid sequence set forth in SEQ ID NO: 26.

8. The ADC of claim 7, wherein the heavy chain variable region comprises the amino acid sequence set forth in SEQ ID NO: 76, and wherein the light chain variable region comprises the amino acid sequence set forth in SEQ ID NO: 77.

9. The ADC of claim 8, wherein the antibody is an IgG1 isotype.

10. The ADC of claim 9, wherein the auristatin is monomethylauristatin E (MMAE).

11. The ADC of claim 10, wherein the antibody is conjugated to MMAE via a maleimidocaproyl, valine-citrulline linker.

12. A pharmaceutical composition comprising an ADC mixture comprising a plurality of the ADC of claim 11, and a pharmaceutically acceptable carrier.

13. The pharmaceutical composition of claim 12, wherein the ADC mixture has an average drug to antibody ratio (DAR) of 1 to 4.

* * * * *

SEQUENCE LISTING

<160> NUMBER OF SEQ ID NOS: 94

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg Gln Pro Pro Gly Lys Gly Leu Glu Trp

```
                35                  40                  45
Met Gly Tyr Ile Ser Tyr Ser Gly Asn Thr Arg Tyr Gln Pro Ser Leu
         50                  55                  60

Lys Ser Arg Ile Thr Ile Ser Arg Asp Thr Ser Lys Asn Gln Phe Phe
 65                  70                  75                  80

Leu Lys Leu Asn Ser Val Thr Ala Ala Asp Thr Ala Thr Tyr Tyr Cys
                 85                  90                  95

Val Thr Ala Gly Arg Gly Phe Pro Tyr Trp Gly Gln Gly Thr Leu Val
            100                 105                 110

Thr Val Ser Ser
        115

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Ser Ile Ser Ser Asp Phe Ala Trp Asn
 1               5                  10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Ser Tyr Ser Gly Asn Thr Arg Tyr Gln Pro Ser Leu Lys Ser
 1               5                  10                  15

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Gly Arg Gly Phe Pro Tyr
 1               5

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Met Ser Val Ser Val Gly
 1               5                  10                  15

Asp Arg Val Thr Ile Thr Cys His Ser Ser Gln Asp Ile Asn Ser Asn
             20                  25                  30

Ile Gly Trp Leu Gln Gln Lys Pro Gly Lys Ser Phe Lys Gly Leu Ile
         35                  40                  45
```

```
Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys
                100                 105
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
His Ser Ser Gln Asp Ile Asn Ser Asn Ile Gly
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
His Gly Thr Asn Leu Asp Asp
1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Val Gln Tyr Ala Gln Phe Pro Trp Thr
1               5
```

<210> SEQ ID NO 9
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Arg Asp
                20                  25                  30

Phe Ala Trp Asn Trp Ile Arg Gln Pro Pro Gly Lys Gly Leu Glu Trp
            35                  40                  45

Met Gly Tyr Ile Ser Tyr Asn Gly Asn Thr Tyr Gln Pro Ser Leu
    50                  55                  60

Lys Ser Arg Ile Thr Ile Ser Arg Asp Thr Ser Lys Asn Gln Phe Phe
65                  70                  75                  80
```

```
Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
            100                 105                 110

Thr Val Ser Ser
        115

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Tyr Ser Ile Ser Arg Asp Phe Ala Trp Asn
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Ser Tyr Asn Gly Asn Thr Arg Tyr Gln Pro Ser Leu Lys Ser
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ser Arg Gly Phe Pro Tyr
1               5

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
```

```
                    85                  90                  95
Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 14
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
                20                  25                  30

Phe Ala Trp Asn Trp Ile Arg Gln Pro Pro Gly Lys Gly Leu Glu Trp
            35                  40                  45

Met Gly Tyr Ile Ser Tyr Ser Gly Asn Thr Arg Tyr Gln Pro Ser Leu
50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
    435                 440                 445

<210> SEQ ID NO 15
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Arg Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
            85                  90                  95

Val Thr Ala Ser Arg Gly Phe Pro Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Tyr Ser Ile Ser Asn Asp Phe Ala Trp Asn
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 17

Tyr Ile Ser Tyr Lys Gly Asn Thr Arg Tyr Gln Pro Ser Leu Lys Ser
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ser Arg Gly Leu Pro Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ser Arg Gly Phe Pro Trp
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Ser Ile Gly Arg Asp Phe Ala Trp Asn
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Ser Ile His Ser Asp Phe Ala Trp Asn
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ser Trp Gly Leu Pro Trp
1               5

<210> SEQ ID NO 23

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His Ser Ser Gln Asp Ile Thr Tyr Asn Ile Gly
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

His Gly Ala Asn Leu Asp Asp
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Gln Tyr Asp Glu Phe Pro Trp Thr
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Ser Ser Gln Asp Ile Thr Tyr Asn Val Gly
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Gly Ser Asn Leu Asp His
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Val Gln Tyr Asp Asp Phe Pro Trp Thr
1               5
```

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
His Ser Ser Gln Asp Ile Asn Met Asn Val Gly
1               5                   10
```

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
His Gly Ala Ile Leu Asp Asp
1               5
```

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Val Gln Tyr Ala Glu Phe Pro Trp Thr
1               5
```

<210> SEQ ID NO 32
<211> LENGTH: 1210
<212> TYPE: PRT
<213> ORGANISM: Homo sapiens

<400> SEQUENCE: 32

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140
```

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

```
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
```

```
                  980             985              990
Thr Asp Ser Asn Phe Tyr Arg Ala  Leu Met Asp Glu Glu  Asp Met Asp
                995              1000             1005

Asp Val Val Asp Ala Asp Glu  Tyr Leu Ile Pro Gln Gln  Gly Phe
1010            1015                 1020

Phe Ser Ser Pro Ser Thr Ser  Arg Thr Pro Leu Leu Ser  Ser Leu
1025            1030                 1035

Ser Ala Thr Ser Asn Asn Ser  Thr Val Ala Cys Ile Asp  Arg Asn
1040            1045                 1050

Gly Leu Gln Ser Cys Pro Ile  Lys Glu Asp Ser Phe Leu  Gln Arg
1055            1060                 1065

Tyr Ser Ser Asp Pro Thr Gly  Ala Leu Thr Glu Asp Ser  Ile Asp
1070            1075                 1080

Asp Thr Phe Leu Pro Val Pro  Glu Tyr Ile Asn Gln Ser  Val Pro
1085            1090                 1095

Lys Arg Pro Ala Gly Ser Val  Gln Asn Pro Val Tyr His  Asn Gln
1100            1105                 1110

Pro Leu Asn Pro Ala Pro Ser  Arg Asp Pro His Tyr Gln  Asp Pro
1115            1120                 1125

His Ser Thr Ala Val Gly Asn  Pro Glu Tyr Leu Asn Thr  Val Gln
1130            1135                 1140

Pro Thr Cys Val Asn Ser Thr  Phe Asp Ser Pro Ala His  Trp Ala
1145            1150                 1155

Gln Lys Gly Ser His Gln Ile  Ser Leu Asp Asn Pro Asp  Tyr Gln
1160            1165                 1170

Gln Asp Phe Phe Pro Lys Glu  Ala Lys Pro Asn Gly Ile  Phe Lys
1175            1180                 1185

Gly Ser Thr Ala Glu Asn Ala  Glu Tyr Leu Arg Val Ala  Pro Gln
1190            1195                 1200

Ser Ser Glu Phe Ile Gly Ala
1205            1210

<210> SEQ ID NO 33
<211> LENGTH: 943
<212> TYPE: PRT
<213> ORGANISM: Homo sapiens

<400> SEQUENCE: 33

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
            35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
    115                 120                 125
```

```
Lys Thr Val Lys Glu Ile Thr Gly Phe Leu Leu Ile Gln Ala Trp Pro
            130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
            195                 200                 205

Asn Trp Lys Lys Leu Phe Gly Thr Ser Gln Lys Thr Lys Ile Ile
210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
            275                 280                 285

Ile Gln Cys His Pro Glu Cys Leu Pro Gln Ala Met Asn Ile Thr Cys
            290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
            355                 360                 365

Cys Pro Thr Asn Gly Pro Lys Ile Pro Ser Ile Ala Thr Gly Met Val
            370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
            435                 440                 445

Lys Val Leu Gly Ser Gly Ala Phe Gly Thr Val Tyr Lys Gly Leu Trp
450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
            515                 520                 525

Gly Cys Leu Leu Asp Tyr Val Arg Glu His Lys Asp Asn Ile Gly Ser
530                 535                 540

Gln Tyr Leu Leu Asn Trp Cys Val Gln Ile Ala Lys Gly Met Asn Tyr
```

```
                545                 550                 555                 560
Leu Glu Asp Arg Arg Leu Val His Arg Asp Leu Ala Ala Arg Asn Val
                    565                 570                 575
Leu Val Lys Thr Pro Gln His Val Lys Ile Thr Asp Phe Gly Leu Ala
                580                 585                 590
Lys Leu Leu Gly Ala Glu Glu Lys Glu Tyr His Ala Glu Gly Gly Lys
            595                 600                 605
Val Pro Ile Lys Trp Met Ala Leu Glu Ser Ile Leu His Arg Ile Tyr
        610                 615                 620
Thr His Gln Ser Asp Val Trp Ser Tyr Gly Val Thr Val Trp Glu Leu
625                 630                 635                 640
Met Thr Phe Gly Ser Lys Pro Tyr Asp Gly Ile Pro Ala Ser Glu Ile
                    645                 650                 655
Ser Ser Ile Leu Glu Lys Gly Glu Arg Leu Pro Gln Pro Pro Ile Cys
                660                 665                 670
Thr Ile Asp Val Tyr Met Ile Met Val Lys Cys Trp Met Ile Asp Ala
            675                 680                 685
Asp Ser Arg Pro Lys Phe Arg Glu Leu Ile Ile Glu Phe Ser Lys Met
        690                 695                 700
Ala Arg Asp Pro Gln Arg Tyr Leu Val Ile Gln Gly Asp Glu Arg Met
705                 710                 715                 720
His Leu Pro Ser Pro Thr Asp Ser Asn Phe Tyr Arg Ala Leu Met Asp
                    725                 730                 735
Glu Glu Asp Met Asp Asp Val Val Asp Ala Asp Glu Tyr Leu Ile Pro
                740                 745                 750
Gln Gln Gly Phe Phe Ser Ser Pro Ser Thr Ser Arg Thr Pro Leu Leu
            755                 760                 765
Ser Ser Leu Ser Ala Thr Ser Asn Asn Ser Thr Val Ala Cys Ile Asp
        770                 775                 780
Arg Asn Gly Leu Gln Ser Cys Pro Ile Lys Glu Asp Ser Phe Leu Gln
785                 790                 795                 800
Arg Tyr Ser Ser Asp Pro Thr Gly Ala Leu Thr Glu Asp Ser Ile Asp
                    805                 810                 815
Asp Thr Phe Leu Pro Val Pro Glu Tyr Ile Asn Gln Ser Val Pro Lys
                820                 825                 830
Arg Pro Ala Gly Ser Val Gln Asn Pro Val Tyr His Asn Gln Pro Leu
            835                 840                 845
Asn Pro Ala Pro Ser Arg Asp Pro His Tyr Gln Asp Pro His Ser Thr
        850                 855                 860
Ala Val Gly Asn Pro Glu Tyr Leu Asn Thr Val Gln Pro Thr Cys Val
865                 870                 875                 880
Asn Ser Thr Phe Asp Ser Pro Ala His Trp Ala Gln Lys Gly Ser His
                    885                 890                 895
Gln Ile Ser Leu Asp Asn Pro Asp Tyr Gln Gln Asp Phe Phe Pro Lys
                900                 905                 910
Glu Ala Lys Pro Asn Gly Ile Phe Lys Gly Ser Thr Ala Glu Asn Ala
            915                 920                 925
Glu Tyr Leu Arg Val Ala Pro Gln Ser Ser Glu Phe Ile Gly Ala
        930                 935                 940

<210> SEQ ID NO 34
<211> LENGTH: 645
<212> TYPE: PRT
<213> ORGANISM: Homo sapiens
```

<400> SEQUENCE: 34

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
```

-continued

```
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser
                645

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Gly or His
<220> FEATURE:
<221> NAME/KEY: MOD_RES
<222> LOCATION: (6)..(6)
<223> OTHER INFORMATION: Ser, Arg or Asn

<400> SEQUENCE: 35

Gly Tyr Ser Ile Xaa Xaa Asp Phe Ala Trp Asn
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: Ser, Asn or Lys

<400> SEQUENCE: 36

Tyr Ile Ser Tyr Xaa Gly Asn Thr Arg Tyr Gln Pro Ser Leu Lys Ser
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Arg or Trp
<220> FEATURE:
<221> NAME/KEY: MOD_RES
<222> LOCATION: (5)..(5)
<223> OTHER INFORMATION: Phe or Leu
<220> FEATURE:
<221> NAME/KEY: MOD_RES
<222> LOCATION: (7)..(7)
<223> OTHER INFORMATION: Tyr or Trp

<400> SEQUENCE: 37

Ala Ser Xaa Gly Xaa Pro Xaa
1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Asn or Thr
<220> FEATURE:
<221> NAME/KEY: MOD_RES
<222> LOCATION: (8)..(8)
<223> OTHER INFORMATION: Tyr, Met or Ser
<220> FEATURE:
<221> NAME/KEY: MOD_RES
<222> LOCATION: (10)..(10)
<223> OTHER INFORMATION: Ile or Val

<400> SEQUENCE: 38

His Ser Ser Gln Asp Ile Xaa Xaa Asn Xaa Gly
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr, Ala or Ser
<220> FEATURE:
<221> NAME/KEY: MOD_RES
<222> LOCATION: (4)..(4)
<223> OTHER INFORMATION: Asn or Ile
<220> FEATURE:
<221> NAME/KEY: MOD_RES
<222> LOCATION: (7)..(7)
```

```
<223> OTHER INFORMATION: Asp or His

<400> SEQUENCE: 39

His Gly Xaa Xaa Leu Asp Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala or Asp
<220> FEATURE:
<221> NAME/KEY: MOD_RES
<222> LOCATION: (5)..(5)
<223> OTHER INFORMATION: Gln, Glu or Asp

<400> SEQUENCE: 40

Val Gln Tyr Xaa Xaa Phe Pro Trp Thr
1               5

<210> SEQ ID NO 41
<211> LENGTH: 330
<212> TYPE: PRT
<213> ORGANISM: Homo sapiens

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 42
<211> LENGTH: 330
<212> TYPE: PRT
<213> ORGANISM: Homo sapiens

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 43
<211> LENGTH: 107
<212> TYPE: PRT
<213> ORGANISM: Homo sapiens

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 44
<211> LENGTH: 105
<212> TYPE: PRT
<213> ORGANISM: Homo sapiens

<400> SEQUENCE: 44

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 45
<211> LENGTH: 16
<212> TYPE: PRT
<213> ORGANISM: Homo sapiens

<400> SEQUENCE: 45
```

```
Cys Gly Ala Asp Ser Tyr Glu Met Glu Asp Gly Val Arg Lys Cys
 1               5                  10                  15

<210> SEQ ID NO 46
<211> LENGTH: 350
<212> TYPE: PRT
<213> ORGANISM: Homo sapiens

<400> SEQUENCE: 46

Leu Glu Glu Lys Lys Gly Asn Tyr Val Val Thr Asp His Gly Ser Cys
 1               5                  10                  15

Val Arg Ala Cys Gly Ala Asp Ser Tyr Glu Met Glu Asp Gly Val
                 20                  25                  30

Arg Lys Cys Lys Lys Cys Glu Gly Pro Cys Arg Lys Val Cys Asn Gly
             35                  40                  45

Ile Gly Ile Gly Glu Phe Lys Asp Ser Leu Ser Ile Asn Ala Thr Asn
 50                  55                  60

Ile Lys His Phe Lys Asn Cys Thr Ser Ile Ser Gly Asp Leu His Ile
 65                  70                  75                  80

Leu Pro Val Ala Phe Arg Gly Asp Ser Phe Thr His Thr Pro Pro Leu
                 85                  90                  95

Asp Pro Gln Glu Leu Asp Ile Leu Lys Thr Val Lys Glu Ile Thr Gly
                100                 105                 110

Phe Leu Leu Ile Gln Ala Trp Pro Glu Asn Arg Thr Asp Leu His Ala
            115                 120                 125

Phe Glu Asn Leu Glu Ile Ile Arg Gly Arg Thr Lys Gln His Gly Gln
            130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
                165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
        195                 200                 205

Lys Ala Thr Gly Gln Val Cys His Ala Leu Cys Ser Pro Glu Gly Cys
    210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
                245                 250                 255

Glu Phe Val Glu Asn Ser Glu Cys Ile Gln Cys His Pro Glu Cys Leu
            260                 265                 270

Pro Gln Ala Met Asn Ile Thr Cys Thr Gly Arg Gly Pro Asp Asn Cys
        275                 280                 285

Ile Gln Cys Ala His Tyr Ile Asp Gly Pro His Cys Val Lys Thr Cys
    290                 295                 300

Pro Ala Gly Val Met Gly Glu Asn Asn Thr Leu Val Trp Lys Tyr Ala
305                 310                 315                 320

Asp Ala Gly His Val Cys His Leu Cys His Pro Asn Cys Thr Tyr Gly
                325                 330                 335

Cys Thr Gly Pro Gly Leu Glu Gly Cys Pro Thr Asn Gly Pro
            340                 345                 350

<210> SEQ ID NO 47
```

-continued

```
<211> LENGTH: 525
<212> TYPE: PRT
<213> ORGANISM: Homo sapiens

<400> SEQUENCE: 47

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
```

```
                385                 390                 395                 400
Ile Thr Gly Phe Leu Leu Ile Gln Ala Trp Pro Glu Asn Arg Thr Asp
                    405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser
                515                 520                 525

<210> SEQ ID NO 48
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Pro Lys Ser
    210                 215                 220
```

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
            450

<210> SEQ ID NO 49
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Ala
    210

<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser
        115

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Leu Gly Trp Leu Gln Gln Lys Pro Gly Lys Ser Phe Lys Gly Leu Ile
        35                  40                  45

Tyr His Gly Ser Asn Leu Asp His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Val Gln Tyr Asp Gln Phe Pro Trp
                85                  90                  95

Thr Phe Gly Gly Gly Thr Lys Leu Glu Ile Lys
            100                 105

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Arg Asp
                20                  25                  30

Phe Ala Trp Asn Trp Ile Arg Gln Pro Pro Gly Lys Gly Leu Glu Trp
            35                  40                  45

Met Gly Tyr Ile Ser Tyr Ser Gly Asn Thr Arg Tyr Gln Pro Ser Leu
50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
            100                 105                 110

Thr Val Ser Ser
        115

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
                20                  25                  30

Ile Gly Trp Leu Gln Gln Lys Pro Gly Lys Ser Phe Lys Gly Leu Ile
            35                  40                  45

Tyr His Gly Thr Asn Leu Asp Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 54
<211> LENGTH: 116
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 54

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Gly Lys Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Leu Pro Tyr Trp Gly Gln Gly Thr Leu Val
            100                 105                 110

Thr Val Ser Ser
        115

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Ile Gly Trp Leu Gln Gln Lys Pro Gly Lys Ser Phe Lys Gly Leu Ile
        35                  40                  45

Tyr His Gly Ala Asn Leu Asp Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Glu Phe Pro Trp
                85                  90                  95

Thr Phe Gly Gly Gly Thr Lys Leu Glu Ile Lys
            100                 105

<210> SEQ ID NO 56
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Gly Lys Asp
            20                  25                  30
```

```
Phe Ala Trp Asn Trp Ile Arg Gln Pro Pro Gly Lys Gly Leu Glu Trp
            35                  40                  45

Met Gly Tyr Ile Ser Tyr Ser Gly Asn Thr Arg Tyr Gln Pro Ser Leu
 50                  55                  60

Lys Ser Arg Ile Thr Ile Ser Arg Asp Thr Ser Lys Asn Gln Phe Phe
 65                  70                  75                  80

Leu Lys Leu Asn Ser Val Thr Ala Ala Asp Thr Ala Thr Tyr Tyr Cys
                 85                  90                  95

Val Thr Ala Ser Arg Gly Leu Pro Tyr Trp Gly Gln Gly Thr Leu Val
                100                 105                 110

Thr Val Ser Ser
            115

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Met Ser Val Ser Val Gly
 1               5                  10                  15

Asp Arg Val Thr Ile Thr Cys His Ser Ser Gln Asp Ile Thr Tyr Asn
                 20                  25                  30

Ile Gly Trp Leu Gln Gln Lys Pro Gly Lys Ser Phe Lys Gly Leu Ile
            35                  40                  45

Tyr His Gly Ala Asn Leu Asp Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Val Gln Tyr Asp Glu Phe Pro Trp
                 85                  90                  95

Thr Phe Gly Gly Gly Thr Lys Leu Glu Ile Lys
            100                 105

<210> SEQ ID NO 58
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Gly Lys Asp
                 20                  25                  30

Phe Ala Trp Asn Trp Ile Arg Gln Pro Pro Gly Lys Gly Leu Glu Trp
            35                  40                  45

Met Gly Tyr Ile Ser Tyr Asn Gly Asn Thr Arg Tyr Gln Pro Ser Leu
 50                  55                  60

Lys Ser Arg Ile Thr Ile Ser Arg Asp Thr Ser Lys Asn Gln Phe Phe
 65                  70                  75                  80

Leu Lys Leu Asn Ser Val Thr Ala Ala Asp Thr Ala Thr Tyr Tyr Cys
                 85                  90                  95
```

```
Val Thr Ala Ser Arg Gly Leu Pro Tyr Trp Gly Gln Gly Thr Leu Val
                100                 105                 110

Thr Val Ser Ser
        115

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Val Gly Trp Leu Gln Gln Lys Pro Gly Lys Ser Phe Lys Gly Leu Ile
        35                  40                  45

Tyr His Gly Ser Asn Leu Asp His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Asp Phe Pro Trp
                85                  90                  95

Thr Phe Gly Gly Gly Thr Lys Leu Glu Ile Lys
                100                 105

<210> SEQ ID NO 60
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Gly Arg Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
                100                 105                 110

Thr Val Ser Ser
        115

<210> SEQ ID NO 61
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 61

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Val Gly Trp Leu Gln Gln Lys Pro Gly Lys Ser Phe Lys Gly Leu Ile
        35                  40                  45

Tyr His Gly Ser Asn Leu Asp His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Asp Phe Pro Trp
                85                  90                  95

Thr Phe Gly Gly Gly Thr Lys Leu Glu Ile Lys
            100                 105

<210> SEQ ID NO 62
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Gly Lys Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
            100                 105                 110

Thr Val Ser Ser
        115

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Val Gly Trp Leu Gln Gln Lys Pro Gly Lys Ser Phe Lys Gly Leu Ile

```
                35                  40                  45
Tyr His Gly Ser Asn Leu Asp His Gly Val Pro Ser Arg Phe Ser Gly
        50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Val Gln Tyr Asp Asp Phe Pro Trp
                85                  90                  95
Thr Phe Gly Gly Gly Thr Lys Leu Glu Ile Lys
                100                 105
```

<210> SEQ ID NO 64
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Glu Val Gln Leu Gln Glu Ser Gly Pro Gly Leu Val Lys Pro Ser Gln
1               5                   10                  15
Thr Leu Ser Leu Thr Cys Thr Val Ser Gly Tyr Ser Ile Ser Asn Asp
                20                  25                  30
Phe Ala Trp Asn Trp Ile Arg Gln Pro Pro Gly Lys Gly Leu Glu Trp
                35                  40                  45
Met Gly Tyr Ile Ser Tyr Lys Gly Asn Thr Arg Tyr Gln Pro Ser Leu
        50                  55                  60
Lys Ser Arg Ile Thr Ile Ser Arg Asp Thr Ser Lys Asn Gln Phe Phe
65                  70                  75                  80
Leu Lys Leu Asn Ser Val Thr Ala Ala Asp Thr Ala Thr Tyr Tyr Cys
                85                  90                  95
Val Thr Ala Ser Arg Gly Phe Pro Trp Trp Gly Gln Gly Thr Leu Val
                100                 105                 110
Thr Val Ser Ser
        115
```

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Asp Ile Gln Met Thr Gln Ser Pro Ser Ser Met Ser Val Ser Val Gly
1               5                   10                  15
Asp Arg Val Thr Ile Thr Cys His Ser Ser Gln Asp Ile Asn Ser Asn
                20                  25                  30
Ile Gly Trp Leu Gln Gln Lys Pro Gly Lys Ser Phe Lys Gly Leu Ile
                35                  40                  45
Tyr His Gly Thr Asn Leu Asp Asp Gly Val Pro Ser Arg Phe Ser Gly
        50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Val Gln Tyr Ala Gln Phe Pro Trp
                85                  90                  95
Thr Phe Gly Gly Gly Thr Lys Leu Glu Ile Lys
```

<210> SEQ ID NO 66
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser
        115

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Glu Gln Phe Pro Trp
                85                  90                  95

Thr Phe Gly Gly Gly Thr Lys Leu Glu Ile Lys
            100                 105

<210> SEQ ID NO 68
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser
            115

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Leu Gly Trp Leu Gln Gln Lys Pro Gly Lys Ser Phe Lys Gly Leu Ile
        35                  40                  45

Tyr His Gly Ala Asn Leu His Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Glu Phe Pro Trp
                85                  90                  95

Thr Phe Gly Gly Gly Thr Lys Leu Glu Ile Lys
            100                 105

<210> SEQ ID NO 70
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser His Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
    50                  55                  60
```

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Trp Gly Leu Pro Trp Trp Gly Gln Gly Thr Leu Val
            100                 105                 110

Thr Val Ser Ser
        115

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Met Asn
            20                  25                  30

Val Gly Trp Leu Gln Gln Lys Pro Gly Lys Ser Phe Lys Gly Leu Ile
        35                  40                  45

Tyr His Gly Ala Ile Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Glu Phe Pro Trp
                85                  90                  95

Thr Phe Gly Gly Gly Thr Lys Leu Glu Ile Lys
            100                 105

<210> SEQ ID NO 72
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Asn Asp
            20                  25                  30

Phe Ala Trp Asn Trp Ile Arg Gln Leu Pro Gly Lys Gly Leu Glu Trp
        35                  40                  45

Met Gly Tyr Ile Ser Tyr Lys Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Leu Pro Tyr Trp Gly Gln Gly Thr Leu Val
            100                 105                 110

Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Ile Gly Trp Leu Gln Gln Lys Pro Gly Lys Ser Phe Lys Gly Leu Ile
        35                  40                  45

Tyr His Gly Ala Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Glu Phe Pro Trp
                85                  90                  95

Thr Phe Gly Gly Gly Thr Lys Leu Glu Ile Lys
            100                 105

<210> SEQ ID NO 74
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Arg Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Trp Trp Gly Gln Gly Thr Leu Val
            100                 105                 110

Thr Val Ser Ser
        115

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Val Gly Trp Leu Gln Gln Lys Pro Gly Lys Ser Phe Lys Gly Leu Ile
            35                  40                  45

Tyr His Gly Ser Asn Leu Asp His Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Asp Phe Pro Trp
                85                  90                  95

Thr Phe Gly Gly Gly Thr Lys Leu Glu Ile Lys
            100                 105
```

<210> SEQ ID NO 76
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Gly Arg Asp
            20                  25                  30

Phe Ala Trp Asn Trp Ile Arg Gln Pro Pro Gly Lys Gly Leu Glu Trp
            35                  40                  45

Met Gly Tyr Ile Ser Tyr Asn Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
            100                 105                 110

Thr Val Ser Ser
        115
```

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Thr Tyr Asn
            20                  25                  30

Val Gly Trp Leu Gln Gln Lys Pro Gly Lys Ser Phe Lys Gly Leu Ile
            35                  40                  45

Tyr His Gly Ser Asn Leu Asp His Gly Val Pro Ser Arg Phe Ser Gly
    50                  55                  60
```

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Asp Asp Phe Pro Trp
                85                  90                  95

Thr Phe Gly Gly Gly Thr Lys Leu Glu Ile Lys
            100                 105

<210> SEQ ID NO 78
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser His Asp
                20                  25                  30

Phe Ala Trp Asn Trp Ile Arg Gln Pro Pro Gly Lys Gly Leu Glu Trp
            35                  40                  45

Met Gly Tyr Ile Ser Tyr Ser Gly Asn Thr Arg Tyr Gln Pro Ser Leu
        50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Trp Gly Leu Pro Trp Trp Gly Gln Gly Thr Leu Val
            100                 105                 110

Thr Val Ser Ser
        115

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Met Asn
                20                  25                  30

Val Gly Trp Leu Gln Gln Lys Pro Gly Lys Ser Phe Lys Gly Leu Ile
            35                  40                  45

Tyr His Gly Ala Ile Leu Asp Asp Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Glu Phe Pro Trp
                85                  90                  95

Thr Phe Gly Gly Gly Thr Lys Leu Glu Ile Lys
            100                 105

<210> SEQ ID NO 80
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Tyr Ser Ile Gly Lys Asp Phe Ala Trp Asn
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Tyr Ser Ile Ser His Asp Phe Ala Trp Asn
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

His Ser Ser Gln Asp Ile Asn Ser Asn Leu Gly
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Gly Ala Asn Leu His Asp
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Gln Tyr Glu Gln Phe Pro Trp Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Gln Tyr Asp Gln Phe Pro Trp Thr
```

<210> SEQ ID NO 86
<211> LENGTH: 1338
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
gaggtgcaac tccaagagag cgggcccggc ctcgtgaagc cctctcagac tctgtccctg      60
acttgcactg tgagcgggta ttccatcagc agagacttcg catggaactg gatccgccag     120
cctcccggta agggactgga gtggatgggg tacatcagct acaacggtaa tacacgctat     180
cagccctccc tgaagtctcg cattaccatt agtcgcgata cctccaagaa ccagttcttt     240
ctgaaactca acagcgtgac agccgctgac accgccacct actactgcgt gaccgccagc     300
aggggggttcc cttactgggg ccagggcact ctggtcaccg tttcttctgc gtcgaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggaccsctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gcgaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct cctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 87
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
gacatccaga tgacccagtc cccctccagt atgtctgtgt ctgtgggcga ccgtgtgacc      60
attacctgcc actcctccca ggacatcaat agcaatatcg gttggttgca acagaagcca     120
ggcaagtcct tcaagggct gatttaccat ggtaccaacc tggacgacgg ggttcctagt     180
cgtttcagcg gctccgggtc cggaaccgat tacactctga ccatcagcag tttgcagcct     240
gaggactttg ctacctatta ttgtgtgcag tacgctcagt cccatggac tttcggcggg     300
```

```
ggcaccaaac tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Met Glu Phe Gly Leu Ser Trp Leu Phe Leu Val Ala Ile Leu Lys Gly
1               5                   10                  15

Val Gln Cys
```

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Met Arg Val Pro Ala Gln Leu Leu Gly Leu Leu Leu Leu Trp Phe Pro
1               5                   10                  15

Gly Ser Arg Cys
            20
```

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Leu Glu Ser Arg Gly Pro Phe
1               5
```

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Asn Met His Thr Gly His His His His His His
1               5                   10
```

<210> SEQ ID NO 92
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 92

Ser Arg Gly Pro Phe
1               5

<210> SEQ ID NO 93
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Thr Gly Glu Ile Tyr His Ser Gly Ser Thr Asn Tyr Asn Pro Ser Leu
    50                  55                  60

Lys Ser Arg Ile Thr Ile Ser Val Asp Lys Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Arg

<210> SEQ ID NO 94
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Met Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Glu Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95
```